United States Patent
Weiss et al.

(10) Patent No.: US 10,723,695 B2
(45) Date of Patent: Jul. 28, 2020

(54) MICROBIOCIDAL PHENYLAMIDINE DERIVATIVES

(71) Applicant: SYNGENTA PARTICIPATIONS AG, Basel (CH)

(72) Inventors: Matthias Weiss, Stein (CH); Julien Daniel Gagnepain, Stein (CH); Thomas James Hoffman, Stein (CH); Sarah Sulzer-Mosse, Stein (CH); Clemens Lamberth, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/782,008

(22) PCT Filed: Dec. 12, 2016

(86) PCT No.: PCT/EP2016/080616
§ 371 (c)(1),
(2) Date: Jun. 6, 2018

(87) PCT Pub. No.: WO2017/102635
PCT Pub. Date: Jun. 22, 2017

(65) Prior Publication Data
US 2018/0362451 A1    Dec. 20, 2018

(30) Foreign Application Priority Data

Dec. 15, 2015 (EP) .................... 15200221
Sep. 6, 2016 (EP) .................... 16187387

(51) Int. Cl.
| | |
|---|---|
| *C07C 257/12* | (2006.01) |
| *A01N 37/52* | (2006.01) |
| *A01N 43/40* | (2006.01) |
| *C07D 249/08* | (2006.01) |
| *C07D 333/58* | (2006.01) |
| *C07D 295/125* | (2006.01) |
| *C07D 333/20* | (2006.01) |
| *C07C 317/32* | (2006.01) |
| *C07D 231/56* | (2006.01) |
| *C07D 231/12* | (2006.01) |

(Continued)

(52) U.S. Cl.
CPC ............ *C07C 257/12* (2013.01); *A01N 37/52* (2013.01); *A01N 43/10* (2013.01); *A01N 43/12* (2013.01); *A01N 43/36* (2013.01); *A01N 43/38* (2013.01); *A01N 43/40* (2013.01); *A01N 43/52* (2013.01); *A01N 43/54* (2013.01); *A01N 43/56* (2013.01); *A01N 43/653* (2013.01); *C07C 317/32* (2013.01); *C07C 321/28* (2013.01); *C07D 213/61* (2013.01); *C07D 213/64* (2013.01); *C07D 231/12* (2013.01); *C07D 231/16* (2013.01); *C07D 231/56* (2013.01); *C07D 235/06* (2013.01); *C07D 235/08* (2013.01); *C07D 239/26* (2013.01); *C07D 239/34* (2013.01); *C07D 249/08* (2013.01); *C07D 295/125* (2013.01); *C07D 333/20* (2013.01); *C07D 333/24* (2013.01); *C07D 333/58* (2013.01); *C07D 333/60* (2013.01); *C07C 2601/02* (2017.05); *C07C 2601/04* (2017.05); *C07C 2601/08* (2017.05); *C07C 2601/10* (2017.05); *C07C 2601/14* (2017.05); *C07C 2601/16* (2017.05)

(58) Field of Classification Search
CPC ... C07C 257/12; C07C 317/32; C07C 321/28; A01N 37/52
See application file for complete search history.

(56) References Cited

U.S. PATENT DOCUMENTS

| | | | |
|---|---|---|---|
| 2009/0197918 A1 | 8/2009 | Kunz et al. | |
| 2014/0206020 A1 | 7/2014 | Valdez et al. | |

FOREIGN PATENT DOCUMENTS

| | | |
|---|---|---|
| CA | 2447640 A1 | 12/2002 |
| EP | 0002679 A1 | 7/1979 |

(Continued)

OTHER PUBLICATIONS

Webster's New World Dictionary, 2nd college ed., The World Publishing Co., New York, 1972, p. 1127.*

(Continued)

*Primary Examiner* — John Pak
(74) *Attorney, Agent, or Firm* — Baker & Hostetler, LLP; Toni-Junell Herbert

(57) ABSTRACT

Compounds of the formula (I) wherein $R^1$, $R^2$, $R^3$, $R^4$, $R^5$, $R^6$, $R^7$, $R^8$ and X are as defined in claim 1. Furthermore, the present invention relates to agrochemical compositions which comprise compounds of formula (I), to preparation of these compositions, and to the use of the compounds or compositions in agriculture or horticulture for combating, preventing or controlling infestation of plants, harvested food crops, seeds or non-living materials by phytopathogenic microorganisms, in particular fungi.

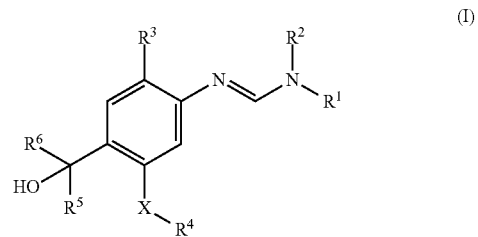

(I)

17 Claims, No Drawings

(51) Int. Cl.

| | |
|---|---|
| *C07D 235/08* | (2006.01) |
| *C07D 239/34* | (2006.01) |
| *C07C 321/28* | (2006.01) |
| *C07D 213/61* | (2006.01) |
| *A01N 43/54* | (2006.01) |
| *A01N 43/38* | (2006.01) |
| *A01N 43/653* | (2006.01) |
| *A01N 43/36* | (2006.01) |
| *A01N 43/10* | (2006.01) |
| *A01N 43/56* | (2006.01) |
| *C07D 333/24* | (2006.01) |
| *A01N 43/52* | (2006.01) |
| *C07D 333/60* | (2006.01) |
| *C07D 213/64* | (2006.01) |
| *C07D 239/26* | (2006.01) |
| *C07D 235/06* | (2006.01) |
| *C07D 231/16* | (2006.01) |
| *A01N 43/12* | (2006.01) |

(56) References Cited

FOREIGN PATENT DOCUMENTS

| | | |
|---|---|---|
| EP | 0884311 A2 | 12/1998 |
| WO | 2000/46184 A1 | 8/2000 |
| WO | 2012/146125 A1 | 11/2012 |
| WO | 2015/121802 A1 | 8/2015 |

OTHER PUBLICATIONS

International Search Report and Written Opinion dated Mar. 14, 2017 in International Application No. PCT/EP2016/080616, 10 pages.

Nadim, et al., "Synthesis and Antimicrobial Properties of Fluorinated 1,2-Aminopropanethiols", Russian Journal of Applied Chemistry, vol. 75, No. 8, pp. 1280-1282, 2002.

IPRP for PCT/EP2016/080616, dated Jun. 28, 2018.

\* cited by examiner

MICROBIOCIDAL PHENYLAMIDINE DERIVATIVES

CROSS-REFERENCE TO RELATED APPLICATIONS

This application is a 371 National Stage application of International Application No. PCT/EP2016/080616, filed Dec. 12, 2016, which claims priority to European Patent Application No. 15200221.8, filed Dec. 15, 2015 and European Patent Application No. 16187387.2, filed Sep. 6, 2016, the entire contents of which applications are hereby incorporated by reference.

The present invention relates to novel phenylamidine derivatives, which have microbiocidal activity, e.g. as active ingredients, in particular fungicidal activity. The invention also relates to preparation of these phenylamidine derivatives, to intermediates useful in the preparation of these phenylamidine derivatives, to the preparation of these intermediates, to agrochemical compositions which comprise at least one of the phenylamidine derivatives, to preparation of these compositions and to the use of the phenylamidine derivatives or compositions in agriculture or horticulture for controlling or preventing infestation of plants, harvested food crops, seeds or non-living materials by phytopathogenic microorganisms, in particular fungi.

Certain fungicidal phenylamidine compounds are described in WO 00/46184.

It has now surprisingly been found that certain novel phenylamidine derivatives have favourable fungicidal properties.

The present invention therefore provides compounds of formula (I)

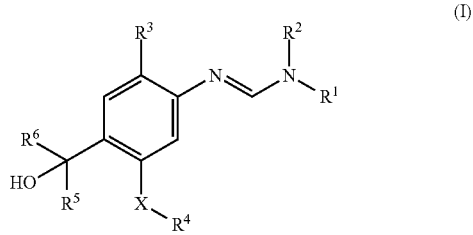

wherein, $R^1$ and $R^2$ are each independently selected from $C_1$-$C_4$ alkyl and $C_3$-$C_8$ cycloalkyl; or $R^1$ and $R^2$ together with the nitrogen atom to which they are attached form a three to six-membered saturated cyclic group which may optionally contain one oxygen or one sulphur atom;

$R^3$ is hydrogen, halogen or $C_1$-$C_4$ alkyl;

$R^4$ is $C_1$-$C_4$ alkyl or $C_1$-$C_4$ haloalkyl;

$R^5$ and $R^6$ are each independently selected from $C_1$-$C_6$alkyl, $C_1$-$C_6$ haloalkyl, $C_3$-$C_8$ cycloalkyl, $C_2$-$C_6$ alkenyl, $C_2$-$C_6$ haloalkenyl, $C_2$-$C_8$ alkynyl, aryl (optionally substituted with one to three $R^7$ groups), aryl($C_1$-$C_4$)alkyl wherein the aryl is optionally substituted with one to three $R^7$ groups, heteroaryl($C_1$-$C_4$)alkyl wherein the heteroaryl is optionally substituted with one to three $R^7$ groups and heteroaryl (optionally substituted with one to three $R^7$ groups);

X is $NR^8$, O or S;

Each $R^7$ is independently selected from halogen, cyano, hydroxyl, amino, nitro, $C_1$-$C_4$alkyl, $C_1$-$C_4$haloalkyl, $C_3$-$C_6$cycloalkyl, $C_3$-$C_6$halocycloalkyl, $C_1$-$C_4$alkoxy, $C_1$-$C_4$haloalkoxy, $C_3$-$C_6$cycloalkoxy, $C_1$-$C_4$alkylthio, $C_1$-$C_4$haloalkylthio, $C_3$-$C_6$cycloalkylthio, $C_1$-$C_4$alkylsulfinyl, $C_1$-$C_4$haloalkylsulfinyl, $C_1$-$C_4$alkylsulfonyl, $C_1$-$C_4$haloalkylsulfonyl, $C_1$-$C_4$alkylcarbonyl, $C_2$-$C_6$alkenyl, $C_2$-$C_6$haloalkenyl, $C_2$-$C_6$alkenyloxy, $C_2$-$C_6$haloalkenyloxy, $C_2$-$C_6$alkynyl, $C_3$-$C_6$cycloalkyl$C_2$-$C_6$alkynyl, $C_2$-$C_6$alkynyloxy, aryl, aryl ($C_1$-$C_4$)alkyl, aryloxy, heteroaryl, heteroaryl($C_1$-$C_4$)alkyl and heteroaryloxy; and $R^8$ is selected from hydrogen, $C_1$-$C_4$ alkyl, $C_1$-$C_4$ alkoxy and $C_3$-$C_8$cycloalkyl; or a salt or an N-oxide thereof.

In a second aspect the present invention provides an agrochemical composition comprising a compound of formula (I).

Compounds of formula (I) may be used to control phytopathogenic microorganisms. Thus, in order to control a phytopathogen a compound of formula (I), or a composition comprising a compound of formula (I), according to the invention may be applied directly to the phytopathogen, or to the locus of a phytopathogen, in particular to a plant susceptible to attack by phytopathogens.

Thus, in a third aspect the present invention provides the use of a compound of formula (I), or a composition comprising a compound of formula (I), as described herein to control a phytopathogen.

In a further aspect the present invention provides a method of controlling phytopathogens, comprising applying a compound of formula (I), or a composition comprising a compound of formula (I), as described herein to said phytopathogen, or to the locus of said phytopathogen, in particular to a plant susceptible to attack by a phytopathogen.

Compounds of formula (I) are particularly effective in the control of phytopathogenic fungi.

Thus, in a yet further aspect the present invention provides the use of a compound of formula (I), or a composition comprising a compound of formula (I), as described herein to control phytopathogenic fungi.

In a further aspect the present invention provides a method of controlling phytopathogenic fungi, comprising applying a compound of formula (I), or a composition comprising a compound of formula (I), as described herein to said phytopathogenic fungi, or to the locus of said phytopathogenic fungi, in particular to a plant susceptible to attack by phytopathogenic fungi.

Where substituents are indicated as being optionally substituted, this means that they may or may not carry one or more identical or different substituents, e.g. one to three substituents. Normally not more than three such optional substituents are present at the same time. Where a group is indicated as being substituted, e.g. alkyl, this includes those groups that are part of other groups, e.g. the alkyl in alkylthio.

The term "halogen" refers to fluorine, chlorine, bromine or iodine, preferably fluorine, chlorine or bromine.

Alkyl substituents may be straight-chained or branched. Alkyl on its own or as part of another substituent is, depending upon the number of carbon atoms mentioned, for example, methyl, ethyl, n-propyl, n-butyl, n-pentyl, n-hexyl and the isomers thereof, for example, isopropyl, iso-butyl, sec-butyl, tert-butyl or iso-amyl.

Alkenyl substituents (either alone or as part of a larger group, eg. alkenyloxy) can be in the form of straight or branched chains, and the alkenyl moieties, where appropriate, can be of either the (E)- or (Z)-configuration. Examples are vinyl and allyl. The alkenyl groups are preferably $C_2$-$C_6$, more preferably $C_2$-$C_4$ and most preferably $C_2$-$C_3$ alkenyl groups.

Alkynyl substituents (either alone or as part of a larger group, eg. alkynyloxy) can be in the form of straight or branched chains. Examples are ethynyl and propargyl. The alkynyl groups are preferably $C_2$-$C_6$, more preferably $C_2$-$C_4$ and most preferably $C_2$-$C_3$ alkynyl groups.

Haloalkyl groups (either alone or as part of a larger group, eg. haloalkyloxy) may contain one or more identical or different halogen atoms and, for example, may stand for $CH_2Cl$, $CHCl_2$, $CCl_3$, $CH_2F$, $CHF_2$, $CF_3$, $CF_2Cl$, $CF_3CH_2$, $CH_3CF_2$, $CF_3CF_2$ or $CCl_3CCl_2$.

Haloalkenyl groups (either alone or as part of a larger group, eg. haloalkenyloxy) are alkenyl groups, respectively, which are substituted with one or more of the same or different halogen atoms and are, for example, 2,2-difluoro-vinyl or 1,2-dichloro-2-fluoro-vinyl.

Alkoxy means a radical —OR, where R is alkyl, e.g. as defined above. Alkoxy groups include, but are not limited to, methoxy, ethoxy, 1-methylethoxy, propoxy, butoxy, 1-methylpropoxy and 2-methylpropoxy.

Cyano means a —CN group.
Nitro means a —$NO_2$ group.
Amino means an —$NH_2$ group.
Hydroxyl or hydroxy stands for a —OH group.
Cycloalkyl may be saturated or partially unsaturated, preferably fully saturated, and is, for example, cyclopropyl, cyclobutyl, cyclopentyl, cyclohexyl, or cyclohexenyl.

Aryl groups (either alone or as part of a larger group, such as e.g. aryloxy, aryl-alkyl) are aromatic ring systems which can be in mono-, bi- or tricyclic form. Examples of such rings include phenyl, naphthyl, anthracenyl, indenyl or phenanthrenyl. Preferred aryl groups are phenyl and naphthyl, phenyl being most preferred. Where an aryl moiety is said to be substituted, the aryl moiety is preferably substituted by one to four substituents, most preferably by one to three substituents.

Heteroaryl groups (either alone or as part of a larger group, such as e.g. heteroaryloxy, heteroaryl-alkyl) are aromatic ring systems containing at least one heteroatom and consisting either of a single ring or of two or more fused rings. Preferably, single rings will contain up to three heteroatoms and bicyclic systems up to four heteroatoms which will preferably be chosen from nitrogen, oxygen and sulfur. Examples of monocyclic groups include pyridyl, pyridazinyl, pyrimidinyl, pyrazinyl, pyrrolyl, pyrazolyl, imidazolyl, triazolyl (e.g. [1,2,4] triazolyl), furanyl, thiophenyl, oxazolyl, isoxazolyl, oxadiazolyl, thiazolyl, isothiazolyl and thiadiazolyl. Examples of bicyclic groups include purinyl, quinolinyl, cinnolinyl, quinoxalinyl, indolyl, indazolyl, benzimidazolyl, benzothiophenyl and benzothiazolyl. Monocyclic heteroaryl groups are preferred, pyridyl being most preferred. Where a heteroaryl moiety is said to be substituted, the heteroaryl moiety is preferably substituted by one to four substituents, most preferably by one to three substituents.

Heterocyclyl groups or heterocyclic rings (either alone or as part of a larger group, such as heterocyclyl-alkyl) are non-aromatic ring structures containing up to 10 atoms including one or more (preferably one, two or three) heteroatoms selected from O, S and N. Examples of monocyclic groups include, oxetanyl, 4,5-dihydro-isoxazolyl, thietanyl, pyrrolidinyl, tetrahydrofuranyl, [1,3]dioxolanyl, piperidinyl, piperazinyl, [1,4]dioxanyl, imidazolidinyl, [1,3,5]oxadiazinanyl, hexahydro-pyrimidinyl, [1,3,5]triazinanyl and morpholinyl or their oxidised versions such as 1-oxo-thietanyl and 1,1-dioxo-thietanyl. Examples of bicyclic groups include 2,3-dihydro-benzofuranyl, benzo[1,4]dioxolanyl, benzo[1,3]dioxolanyl, chromenyl, and 2,3-dihydro-benzo[1,4]dioxinyl. Where a heterocyclyl moiety is said to be substituted, the heterocyclyl moiety is preferably substituted by one to four substituents, most preferably by one to three substituents.

The presence of one or more possible asymmetric carbon atoms in a compound of formula (I) means that the compounds may occur in optically isomeric forms, i.e. enantiomeric or diastereomeric forms. Also atropisomers may occur as a result of restricted rotation about a single bond. Formula (I) is intended to include all those possible isomeric forms and mixtures thereof. The present invention includes all those possible isomeric forms and mixtures thereof for a compound of formula (I). Likewise, formula (I) is intended to include all possible tautomers. The present invention includes all possible tautomeric forms fora compound of formula (I).

In each case, the compounds of formula (I) according to the invention are in free form, in oxidized form as a N-oxide or in salt form, e.g. an agronomically usable salt form.

N-oxides are oxidized forms of tertiary amines or oxidized forms of nitrogen containing heteroaromatic compounds. They are described for instance in the book "Heterocyclic N-oxides" by A. Albini and S. Pietra, CRC Press, Boca Raton 1991.

Preferred values of $R^1$, $R^2$, $R^3$, $R^4$, $R^5$, $R^6$, $R^7$, $R^8$ and X are, in any combination thereof, as set out below:

Preferably $R^1$ and $R^2$ are each independently $C_1$-$C_4$ alkyl.
More preferably $R^1$ and $R^2$ are each independently selected from methyl, ethyl, propyl and isopropyl.
Even more preferably $R^1$ and $R^2$ are each independently selected from methyl, ethyl and isopropyl.
Most preferably $R^1$ is methyl and $R^2$ is ethyl or isopropyl.
Preferably $R^3$ is hydrogen, fluoro, chloro, or $C_1$-$C_4$ alkyl.
More preferably $R^3$ is hydrogen or $C_1$-$C_3$alkyl.
Even more preferably $R^3$ is hydrogen or $C_1$-$C_2$alkyl.
Most preferably $R^3$ is hydrogen or methyl.
Preferably $R^4$ is $C_1$-$C_3$ alkyl or $C_1$-$C_3$haloalkyl.
More preferably $R^4$ is $C_1$-$C_2$ alkyl or $C_1$-$C_2$ haloalkyl.
Even more preferably $R^4$ is methyl or ethyl.
Most preferably $R^4$ is methyl.
It is especially preferred if $R^3$ is hydrogen and $R^4$ is methyl or $R^3$ is methyl and $R^4$ is methyl.
It is most preferred if both of $R^3$ and $R^4$ are methyl.
Preferably $R^5$ and $R^6$ are each independently selected from $C_1$-$C_6$ alkyl, $C_1$-$C_6$ haloalkyl, $C_3$-$C_8$cycloalkyl, $C_2$-$C_6$ alkenyl, phenyl (optionally substituted with one to three $R^7$ groups), phenyl($C_1$-$C_4$)alkyl wherein the phenyl is optionally substituted with one to three $R^7$ groups, pyrazolyl($C_1$-$C_4$)alkyl wherein the pyrazole is optionally substituted with one to three $R^7$ groups and pyridyl (optionally substituted with one to three $R^7$ groups).
More preferably $R^5$ and $R^6$ are each independently selected from $C_1$-$C_6$ alkyl, $C_1$-$C_6$ haloalkyl, $C_3$-$C_5$ cycloalkyl, phenyl (optionally substituted with one or two $R^7$ groups) and pyridyl (optionally substituted with one or two $R^7$ groups).
Even more preferably $R^5$ and $R^6$ are each independently selected from $C_1$-$C_2$ haloalkyl, phenyl (optionally substituted with one or two $R^7$ groups), ethyl, n-propyl, i-propyl, n-butyl, iso-butyl, neo-pentyl, cyclopropyl, cyclobutyl or cyclopentyl.
Most preferably $R^5$ is $CF_3$, $CClF_2$ or $CF_2CF_3$ and $R^6$ is phenyl (optionally substituted by one methyl group and/or one or two halogen atoms, preferably fluoro or chloro), n-propyl, i-propyl, n-butyl, iso-butyl or neo-pentyl.

Preferably X is $NR^3$ or O.

More preferably X is N—$C_1$-$C_4$alkyl or O.

Even more preferably X is N-methyl or O.

Most preferably X is O.

Preferably each $R^7$ is independently selected from halogen, cyano, $C_1$-$C_4$alkyl, $C_1$-$C_4$haloalkyl, $C_3$-$C_6$cycloalkyl, $C_1$-$C_4$alkoxy, $C_1$-$C_4$haloalkoxy, $C_3$-$C_6$cycloalkoxy, $C_1$-$C_4$alkylthio, $C_1$-$C_4$alkylsulfonyl, $C_1$-$C_4$haloalkylsulfonyl, $C_1$-$C_4$alkylcarbonyl, $C_2$-$C_6$alkenyl, $C_2$-$C_6$haloalkenyl, $C_2$-$C_6$alkynyl, phenyl, benzyl, phenoxy, pyridyl, pyridylmethyl and pyridyloxy.

More preferably each $R^7$ is independently selected from halogen, cyano, $C_1$-$C_4$alkyl, $C_1$-$C_4$haloalkyl, $C_3$-$C_6$cycloalkyl, $C_1$-$C_4$alkoxy, $C_1$-$C_4$haloalkoxy, $C_1$-$C_4$alkylthio, $C_1$-$C_4$alkylsulfonyl, $C_1$-$C_4$alkylcarbonyl, $C_2$-$C_6$alkynyl, phenyl, phenoxy and pyridyl.

Even more preferably each $R^7$ is independently selected from halogen, cyano, $C_1$-$C_4$alkyl, $C_1$-$C_4$haloalkyl, $C_1$-$C_4$alkoxy, $C_1$-$C_4$haloalkoxy, $C_2$-$C_6$alkynyl and phenyl.

Most preferably each $R^7$ is independently selected from halogen, cyano, $C_1$-$C_2$alkyl, $C_1$-$C_2$haloalkyl and $C_1$-$C_2$haloalkoxy.

Preferably $R^3$ is hydrogen, $C_1$-$C_4$alkyl or $C_1$-$C_4$alkoxy.

More preferably $R^3$ is hydrogen or $C_1$-$C_4$alkyl.

Even more preferably $R^3$ is hydrogen or methyl.

Most preferably $R^3$ is methyl.

In the compounds of formula (I) embodiments according to the invention are provided as set out below.

Embodiment 1 provides compounds of formula (I), and a salt or N-oxide thereof, as defined above.

Embodiment 2 provides compounds according to embodiment 1 wherein $R^1$ and $R^2$ are each independently $C_1$-$C_4$ alkyl.

Embodiment 3 provides compounds according to embodiment 1 or 2 wherein $R^3$ is hydrogen, fluoro, chloro, or $C_1$-$C_4$alkyl.

Embodiment 4 provides compounds according to any one of embodiments 1, 2 or 3 wherein $R^4$ is $C_1$-$C_3$alkyl or $C_1$-$C_3$haloalkyl.

Embodiment 5 provides compounds according to any one of embodiments 1, 2, 3 or 4 wherein $R^5$ and $R^6$ are each independently selected from $C_1$-$C_6$ alkyl, $C_1$-$C_6$haloalkyl, $C_3$-$C_8$ cycloalkyl, $C_2$-$C_6$alkenyl, phenyl (optionally substituted with one to three $R^7$ groups), phenyl($C_1$-$C_4$)alkyl wherein the phenyl is optionally substituted with one to three $R^7$ groups, pyrazolyl($C_1$-$C_4$)alkyl wherein the pyrazole is optionally substituted with one to three $R^7$ groups and pyridyl (optionally substituted with one to three $R^7$ groups), wherein each $R^7$ is independently selected from halogen, cyano, $C_1$-$C_4$alkyl, $C_1$-$C_4$haloalkyl, $C_3$-$C_6$cycloalkyl, $C_1$-$C_4$alkoxy, $C_1$-$C_4$haloalkoxy, $C_3$-$C_6$cycloalkoxy, $C_1$-$C_4$alkylthio, $C_1$-$C_4$alkylsulfonyl, $C_1$-$C_4$haloalkylsulfonyl, $C_1$-$C_4$alkylcarbonyl, $C_2$-$C_6$alkenyl, $C_2$-$C_6$haloalkenyl, $C_2$-$C_6$alkynyl, phenyl, benzyl, phenoxy, pyridyl, pyridylmethyl and pyridyloxy.

Embodiment 6 provides compounds according to any one of embodiments 1, 2, 3, 4, or 5 wherein X is $NR^8$ or O, wherein $R^8$ is hydrogen, $C_1$-$C_4$alkyl or $C_1$-$C_4$alkoxy.

Embodiment 7 provides compounds according to any one of embodiments 1, 2, 3, 4, 5, or 6 wherein $R^1$ and $R^2$ are each independently selected from methyl, ethyl, propyl and isopropyl.

Embodiment 8 provides compounds according to any one of embodiments 1, 2, 3, 4, 5, 6, or 7 wherein $R^3$ is hydrogen or $C_1$-$C_3$alkyl.

Embodiment 9 provides compounds according to any one of embodiments 1, 2, 3, 4, 5, 6, 7, or 8 wherein $R^4$ is $C_1$-$C_2$ alkyl or $C_1$-$C_2$ haloalkyl.

Embodiment 10 provides compounds according to any one of embodiments 1, 2, 3, 4, 5, 6, 7, 8, or 9 wherein $R^5$ and $R^6$ are each independently selected from $C_1$-$C_6$ alkyl, $C_1$-$C_6$ haloalkyl, $C_3$-$C_5$ cycloalkyl, phenyl (optionally substituted with one or two $R^7$ groups) and pyridyl (optionally substituted with one or two $R^7$ groups), wherein each $R^7$ is independently selected from halogen, cyano, $C_1$-$C_4$alkyl, $C_1$-$C_4$haloalkyl, $C_3$-$C_6$cycloalkyl, $C_1$-$C_4$alkoxy, $C_1$-$C_4$haloalkoxy, $C_1$-$C_4$alkylthio, $C_1$-$C_4$alkylsulfonyl, $C_1$-$C_4$alkylcarbonyl, $C_2$-$C_6$alkynyl, phenyl, phenoxy and pyridyl.

Embodiment 11 provides compounds according to any one of embodiments 1, 2, 3, 4, 5, 6, 7, 8, 9 or 10 wherein X is N—$C_1$-$C_4$alkyl or 0.

Embodiment 12 provides compounds according to any one of embodiments 1, 2, 3, 4, 5, 6, 7, 8, 9, 10 or 11 wherein $R^1$ and $R^2$ are each independently selected from methyl, ethyl and isopropyl.

Embodiment 13 provides compounds according to any one of embodiments 1, 2, 3, 4, 5, 6, 7, 8, 9, 10, 11 or 12 wherein $R^3$ is hydrogen or $C_1$-$C_2$alkyl.

Embodiment 14 provides compounds according to any one of embodiments 1, 2, 3, 4, 5, 6, 7, 8, 9, 10, 11, 12 or 13 wherein $R^4$ is methyl or ethyl.

Embodiment 15 provides compounds according to any one of embodiments 1, 2, 3, 4, 5, 6, 7, 8, 9, 10, 11, 12, 13 or 14 wherein $R^5$ and $R^6$ are each independently selected from $C_1$-$C_2$ haloalkyl, phenyl (optionally substituted with one or two $R^7$ groups), ethyl, n-propyl, i-propyl, n-butyl, iso-butyl, neo-pentyl, cyclopropyl, cyclobutyl or cyclopentyl, wherein each $R^7$ is independently selected from halogen, cyano, $C_1$-$C_4$alkyl, $C_1$-$C_4$haloalkyl, $C_1$-$C_4$alkoxy, $C_1$-$C_4$haloalkoxy, $C_2$-$C_6$alkynyl and phenyl.

Embodiment 16 provides compounds according to any one of embodiments 1, 2, 3, 4, 5, 6, 7, 8, 9, 10, 11, 12, 13, 14 or 15 wherein $R^1$ is methyl and $R^2$ is ethyl or isopropyl.

Embodiment 17 provides compounds according to any one of embodiments 1, 2, 3, 4, 5, 6, 7, 8, 9, 10, 11, 12, 13, 14, 15 or 16 wherein $R^3$ is hydrogen or methyl.

Embodiment 18 provides compounds according to any one of embodiments 1, 2, 3, 4, 5, 6, 7, 8, 9, 10, 11, 12, 13, 14, 15, 16 or 17 wherein $R^4$ is methyl.

Embodiment 19 provides compounds according to any one of embodiments 1, 2, 3, 4, 5, 6, 7, 8, 9, 10, 11, 12, 13, 14, 15, 16, 17 or 18 wherein $R^5$ is $CF_3$, $CClF_2$ or $CF_2CF_3$.

Embodiment 20 provides compounds according to any one of embodiments 1, 2, 3, 4, 5, 6, 7, 8, 9, 10, 11, 12, 13, 14, 15, 16, 17, 18 or 19 wherein $R^6$ is phenyl (optionally substituted by one methyl group and/or one or two halogen atoms, preferably fluoro or chloro), n-propyl, i-propyl, n-butyl, iso-butyl or neo-pentyl.

Embodiment 21 provides compounds according to any one of embodiments 1, 2, 3, 4, 5, 6, 7, 8, 9, 10, 11, 12, 13, 14, 15, 16, 17, 18, 19 or 20 wherein X is N-methyl or O.

Embodiment 22 provides compounds according to any one of embodiments 1, 2, 3, 4, 5, 6, 7, 8, 9, 10, 11, 12, 13, 14, 15, 16, 17, 18, 19, 20 or 21 wherein $R^3$ is hydrogen and $R^4$ is methyl or $R^3$ is methyl and $R^4$ is methyl.

Embodiment 23 provides compounds according to any one of embodiments 1, 2, 3, 4, 5, 6, 7, 8, 9, 10, 11, 12, 13, 14, 15, 16, 17, 18, 19, 20, 21 or 22 wherein both of $R^3$ and $R^4$ are methyl.

Embodiment 24 provides compounds according to any one of embodiments 1, 2, 3, 4, 5, 6, 7, 8, 9, 10, 11, 12, 13, 14, 15, 16, 17, 18, 19, 20, 21, 22 or 23 wherein X is O.

A preferred group of compounds according to the invention are those of formula (I-1) which are compounds of formula (I) wherein $R^1$ and $R^2$ are each independently $C_1$-$C_4$ alkyl; $R^3$ is hydrogen, fluoro, chloro, or $C_1$-$C_4$ alkyl; $R^4$ is $C_1$-$C_3$ alkyl or $C_1$-$C_3$ haloalkyl; $R^5$ and $R^6$ are each independently selected from $C_1$-$C_6$ alkyl, $C_1$-$C_6$ haloalkyl, $C_3$-$C_5$cycloalkyl, $C_2$-$C_6$ alkenyl, phenyl (optionally substituted with one to three $R^7$ groups), phenyl($C_1$-$C_4$)alkyl wherein the phenyl is optionally substituted with one to three $R^7$ groups, pyrazolyl($C_1$-$C_4$)alkyl wherein the pyrazole is optionally substituted with one to three $R^7$ groups and pyridyl (optionally substituted with one to three $R^7$ groups); X is $NR^8$ or O; each $R^7$ is independently selected from halogen, cyano, $C_1$-$C_4$alkyl, $C_1$-$C_4$haloalkyl, $C_3$-$C_6$cycloalkyl, $C_1$-$C_4$alkoxy, $C_1$-$C_1$-$C_4$haloalkoxy, $C_3$-$C_6$cycloalkoxy, $C_1$-$C_4$alkylthio, $C_1$-$C_4$alkylsulfonyl, $C_1$-$C_4$haloalkylsulfonyl, $C_1$-$C_4$alkylcarbonyl, $C_2$-$C_6$alkenyl, $C_2$-$C_6$haloalkenyl, $C_2$-$C_6$alkynyl, phenyl, benzyl, phenoxy, pyridyl, pyridylmethyl and pyridyloxy; and $R^3$ is hydrogen, $C_1$-$C_4$ alkyl or $C_1$-$C_4$alkoxy; or a salt or N-oxide thereof.

A further preferred group of compounds according to the invention are those of formula (I-2) which are compounds of formula (I) wherein $R^1$ and $R^2$ are each independently selected from methyl, ethyl, propyl and isopropyl; $R^3$ is hydrogen or $C_1$-$C_3$alkyl; $R^4$ is $C_1$-$C_2$ alkyl or $C_1$-$C_2$ haloalkyl; $R^5$ and $R^6$ are each independently selected from $C_1$-$C_8$ alkyl, $C_1$-$C_6$ haloalkyl, $C_3$-$C_5$ cycloalkyl, phenyl (optionally substituted with one or two $R^7$ groups) and pyridyl (optionally substituted with one or two $R^7$ groups); X is N—$C_1$-$C_4$alkyl or O; and each $R^7$ is independently selected from halogen, cyano, $C_1$-$C_4$alkyl, $C_1$-$C_4$haloalkyl, $C_3$-$C_6$cycloalkyl, $C_1$-$C_4$alkoxy, $C_1$-$C_4$haloalkoxy, $C_1$-$C_4$alkylthio, $C_1$-$C_4$alkylsulfonyl, $C_1$-$C_4$alkylcarbonyl, $C_2$-$C_6$alkynyl, phenyl, phenoxy and pyridyl; or a salt or N-oxide thereof.

A further preferred group of compounds according to the invention are those of formula (I-3) which are compounds of formula (I) wherein $R^1$ and $R^2$ are each independently selected from methyl, ethyl and isopropyl; $R^3$ is hydrogen or $C_1$-$C_2$ alkyl; $R^4$ is methyl or ethyl; $R^5$ and $R^6$ are each independently selected from $C_1$-$C_2$haloalkyl, phenyl (optionally substituted with one or two $R^7$ groups), ethyl, n-propyl, i-propyl, n-butyl, iso-butyl, neo-pentyl, cyclopropyl, cyclobutyl or cyclopentyl; X is N-methyl or O; and each $R^7$ is independently selected from halogen, cyano, $C_1$-$C_4$alkyl, $C_1$-$C_4$haloalkyl, $C_1$-$C_4$alkoxy, $C_1$-$C_4$haloalkoxy, $C_2$-$C_6$alkynyl and phenyl; or a salt or N-oxide thereof.

A further preferred group of compounds according to the invention are those of formula (I-4) which are compounds of formula (I) wherein $R^1$ is methyl and $R^2$ is ethyl or isopropyl; $R^3$ is hydrogen or methyl; $R^4$ is methyl; $R^5$ is $CF_3$, $CClF_2$ or $CF_2CF_3$; $R^6$ is phenyl (optionally substituted by one methyl group and/or one or two halogen atoms, preferably fluoro or chloro), n-propyl, i-propyl, n-butyl, iso-butyl or neo-pentyl; and X is O; or a salt or N-oxide thereof.

Another group of compounds according to the invention are those of formula (IK) which are compounds of formula (I)

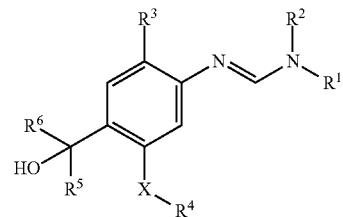

(IK)

wherein
$R^1$ and $R^2$ are each independently selected from $C_1$-$C_4$alkyl and $C_3$-$C_8$cycloalkyl; or
$R^1$ and $R^2$ together with the nitrogen atom to which they are attached form a three to six-membered saturated cyclic group which may optionally contain one oxygen or one sulphur atom;
$R^3$ is hydrogen, halogen or $C_1$-$C_4$alkyl;
$R^4$ is $C_1$-$C_4$alkyl or $C_1$-$C_4$haloalkyl;
$R^5$ and $R^6$ are each independently selected from $C_1$-$C_4$alkyl, $C_1$-$C_4$haloalkyl, $C_3$-$C_8$cycloalkyl, $C_2$-$C_6$alkenyl, $C_2$-$C_6$haloalkenyl, $C_2$-$C_6$alkynyl, aryl (optionally substituted with one to three $R^7$ groups) and heteroaryl (optionally substituted with one to three $R^7$ groups);
X is $NR^3$, O or S;
Each $R^7$ is independently selected from halogen, cyano, hydroxyl, amino, nitro, $C_1$-$C_4$alkyl, $C_1$-$C_4$haloalkyl, $C_3$-$C_6$cycloalkyl, $C_3$-$C_6$halocycloalkyl, $C_1$-$C_4$alkoxy, $C_1$-$C_4$haloalkoxy, $C_3$-$C_6$cycloalkoxy, $C_1$-$C_4$alkylthio, $C_1$-$C_4$haloalkylthio, $C_3$-$C_6$cycloalkylthio, $C_1$-$C_4$alkylsulfinyl, $C_1$-$C_4$haloalkylsulfinyl, $C_1$-$C_4$alkylsulfonyl, $C_1$-$C_4$haloalkylsulfonyl, $C_1$-$C_4$alkylcarbonyl, $C_2$-$C_6$alkenyl, $C_2$-$C_6$haloalkenyl, $C_2$-$C_6$alkenyloxy, $C_2$-$C_6$haloalkenyloxy, $C_2$-$C_6$alkynyl, $C_3$-$C_6$cycloalkyl$C_2$-$C_6$alkynyl, $C_2$-$C_6$alkynyloxy, aryl, aryl($C_1$-$C_4$)alkyl, aryloxy, heteroaryl, heteroaryl($C_1$-$C_4$)alkyl and heteroaryloxy; and
$R^3$ is selected from hydrogen, $C_1$-$C_4$alkyl, $C_1$-$C_4$alkoxy and $C_3$-$C_8$cycloalkyl; or a salt or an N-oxide thereof.

In the compounds of formula (IK) preferred values of $R^1$, $R^2$, $R^3$, $R^4$, $R^5$, $R^6$, $R^7$, $R^8$ and X are, in any combination thereof, as set out below:
Preferably $R^1$ and $R^2$ are each independently $C_1$-$C_4$alkyl.
More preferably $R^1$ and $R^2$ are each independently selected from methyl, ethyl and isopropyl.
Even more preferably $R^1$ and $R^2$ are each independently selected from methyl and ethyl.
Most preferably $R^1$ is methyl and $R^2$ is ethyl.
Preferably $R^3$ is hydrogen or $C_1$-$C_4$alkyl.
More preferably $R^3$ is hydrogen or $C_1$-$C_3$alkyl.
Even more preferably $R^3$ is hydrogen or $C_1$-$C_2$alkyl.
Most preferably $R^3$ is hydrogen or methyl.
Preferably $R^4$ is $C_1$-$C_3$alkyl or $C_1$-$C_3$haloalkyl.
More preferably $R^4$ is $C_1$-$C_2$alkyl or $C_1$-$C_2$haloalkyl.
Even more preferably $R^4$ is methyl or ethyl.
Most preferably $R^4$ is methyl.
It is especially preferred if $R^3$ is hydrogen and $R^4$ is methyl or $R^3$ is methyl and $R^4$ is methyl.
It is most preferred if both of $R^3$ and $R^4$ are methyl.
Preferably $R^5$ and $R^6$ are each independently selected from $C_1$-$C_4$alkyl, $C_1$-$C_4$haloalkyl, $C_3$-$C_8$cycloalkyl, $C_2$-$C_6$alkynyl, phenyl (optionally substituted with one to three $R^7$ groups) and pyridyl (optionally substituted with one to three $R^7$ groups);

More preferably $R^5$ and $R^6$ are each independently selected from $C_1$-$C_4$alkyl, $C_1$-$C_4$haloalkyl, phenyl (optionally substituted with one or two $R^7$ groups) and pyridyl (optionally substituted with one or two $R^7$ groups);

Even more preferably $R^5$ and $R^6$ are each independently selected from $C_1$-$C_4$haloalkyl, phenyl (optionally substituted with one or two $R^7$ groups), n-propyl, n-butyl or pyridyl (optionally substituted with one or two $R^7$ groups);

Most preferably $R^5$ is $C_1$-$C_2$haloalkyl (especially $C_1$-$C_2$fluoroalkyl) and $R^6$ is phenyl (optionally substituted by one or two halogen atoms, preferably fluoro), n-butyl or $C_1$-$C_2$fluoroalkyl.

Preferably X is $NR^3$ or O.

More preferably X is N—$C_1$-$C_4$alkyl or O.

Even more preferably X is N-methyl or O.

Most preferably X is O.

Preferably each $R^7$ is independently selected from halogen, cyano, $C_1$-$C_4$alkyl, $C_1$-$C_4$haloalkyl, $C_3$-$C_6$cycloalkyl, $C_1$-$C_4$alkoxy, $C_1$-$C_4$haloalkoxy, $C_3$-$C_6$cycloalkoxy, $C_1$-$C_4$alkylthio, $C_1$-$C_4$alkylsulfonyl, $C_1$-$C_4$haloalkylsulfonyl, $C_1$-$C_4$alkylcarbonyl, $C_2$-$C_6$alkenyl, $C_2$-$C_6$haloalkenyl, $C_2$-$C_6$alkynyl, phenyl, benzyl, phenoxy, pyridyl, pyridylmethyl and pyridyloxy.

More preferably each $R^7$ is independently selected from halogen, cyano, $C_1$-$C_4$alkyl, $C_1$-$C_4$haloalkyl, $C_3$-$C_6$cycloalkyl, $C_1$-$C_4$alkoxy, $C_1$-$C_4$haloalkoxy, $C_1$-$C_4$alkylthio, $C_1$-$C_4$alkylsulfonyl, $C_1$-$C_4$alkylcarbonyl, $C_2$-$C_6$alkynyl, phenyl, phenoxy and pyridyl.

Even more preferably each $R^7$ is independently selected from halogen, cyano, $C_1$-$C_4$alkyl, $C_1$-$C_4$haloalkyl, $C_1$-$C_4$alkoxy, $C_1$-$C_4$haloalkoxy, $C_2$-$C_6$alkynyl and phenyl.

Most preferably each $R^7$ is independently selected from halogen, cyano, $C_1$-$C_4$haloalkyl and $C_1$-$C_4$haloalkoxy.

Preferably $R^8$ is hydrogen, $C_1$-$C_4$alkyl or $C_1$-$C_4$alkoxy.

More preferably $R^3$ is hydrogen or $C_1$-$C_4$alkyl.

Even more preferably $R^3$ is hydrogen or methyl.

Most preferably $R^3$ is methyl.

In the compounds of formula (IK) embodiments according to the invention are provided as set out below.

Embodiment IK1 provides compounds of formula I, and a salt or N-oxide thereof, as defined above.

Embodiment IK2 provides compounds according to embodiment IK1 wherein $R^1$ and $R^2$ are each independently $C_1$-$C_4$alkyl.

Embodiment IK3 provides compounds according to embodiment IK1 or IK2 wherein $R^3$ is hydrogen or $C_1$-$C_4$alkyl.

Embodiment IK4 provides compounds according to any one of embodiments IK1, IK2 or IK3 wherein $R^4$ is $C_1$-$C_3$alkyl or $C_1$-$C_3$haloalkyl.

Embodiment IK5 provides compounds according to any one of embodiments IK1, IK2, IK3 or IK4 wherein $R^5$ and $R^6$ are each independently selected from $C_1$-$C_4$alkyl, $C_1$-$C_4$haloalkyl, $C_3$-$C_8$cycloalkyl, $C_2$-$C_6$alkynyl, phenyl (optionally substituted with one to three $R^7$ groups) and pyridyl (optionally substituted with one to three $R^7$ groups) and each $R^7$ is independently selected from halogen, cyano, $C_1$-$C_4$alkyl, $C_1$-$C_4$haloalkyl, $C_3$-$C_6$cycloalkyl, $C_1$-$C_4$alkoxy, $C_1$-$C_4$haloalkoxy, $C_3$-$C_6$cycloalkoxy, $C_1$-$C_4$alkylthio, $C_1$-$C_4$alkylsulfonyl, $C_1$-$C_4$haloalkylsulfonyl, $C_1$-$C_4$alkylcarbonyl, $C_2$-$C_6$alkenyl, $C_2$-$C_6$haloalkenyl, $C_2$-$C_6$alkynyl, phenyl, benzyl, phenoxy, pyridyl, pyridylmethyl and pyridyloxy.

Embodiment IK6 provides compounds according to any one of embodiments IK1, IK2, IK3, IK4 or IK5 wherein X is $NR^8$ or O and $R^8$ is hydrogen, $C_1$-$C_4$alkyl or $C_1$-$C_4$alkoxy.

Embodiment IK7 provides compounds according to any one of embodiments IK1, IK2, IK3, IK4, IK5 or IK6 wherein $R^1$ and $R^2$ are each independently selected from methyl, ethyl and isopropyl.

Embodiment IK8 provides compounds according to any one of embodiments IK1, IK2, IK3, IK4, IK5, IK6 or IK7 wherein $R^3$ is hydrogen or $C_1$-$C_3$alkyl.

Embodiment IK9 provides compounds according to any one of embodiments IK1, IK2, IK3, IK4, IK5, IK6, IK7 or IK8 wherein $R^4$ is $C_1$-$C_2$alkyl or $C_1$-$C_2$haloalkyl.

Embodiment IK10 provides compounds according to any one of embodiments IK1, IK2, IK3, IK4, IK5, IK6, IK7, IK8 or IK9 wherein $R^5$ and $R^6$ are each independently selected from $C_1$-$C_4$alkyl, $C_1$-$C_4$haloalkyl, phenyl (optionally substituted with one or two $R^7$ groups) and pyridyl (optionally substituted with one or two $R^7$ groups) and each $R^7$ is independently selected from halogen, cyano, $C_1$-$C_4$alkyl, $C_1$-$C_4$haloalkyl, $C_3$-$C_6$cycloalkyl, $C_1$-$C_4$alkoxy, $C_1$-$C_4$haloalkoxy, $C_1$-$C_4$alkylthio, $C_1$-$C_4$alkylsulfonyl, $C_1$-$C_4$alkylcarbonyl, $C_2$-$C_6$alkynyl, aryl, aryloxy and heteroaryl.

Embodiment IK11 provides compounds according to any one of embodiments IK1, IK2, IK3, IK4, IK5, IK6, IK7, IK8, IK9 or IK10 wherein X is N—$C_1$-$C_4$alkyl or O.

Embodiment IK12 provides compounds according to any one of embodiments IK1, IK2, IK3, IK4, IK5, IK6, IK7, IK8, IK9, IK10 or IK11 wherein $R^1$ and $R^2$ are each independently selected from methyl and ethyl.

Embodiment IK13 provides compounds according to any one of embodiments IK1, IK2, IK3, IK4, IK5, IK6, IK7, IK8, IK9, IK10, IK11 or IK12 wherein $R^3$ is hydrogen or $C_1$-$C_2$ alkyl.

Embodiment IK14 provides compounds according to any one of embodiments IK1, IK2, IK3, IK4, IK5, IK6, IK7, IK8, IK9, IK10, IK11, IK12 or IK13 wherein $R^4$ is methyl or ethyl.

Embodiment IK15 provides compounds according to any one of embodiments IK1, IK2, IK3, IK4, IK5, IK6, IK7, IK8, IK9, IK10, IK11, IK12, IK13 or IK14 wherein $R^5$ and $R^6$ are each independently selected from $C_1$-$C_4$haloalkyl, phenyl (optionally substituted with one or two $R^7$ groups), n-propyl, n-butyl or pyridyl (optionally substituted with one or two $R^7$ groups) and each $R^7$ is independently selected from halogen, cyano, $C_1$-$C_4$alkyl, $C_1$-$C_4$haloalkyl, $C_1$-$C_4$alkoxy, $C_1$-$C_4$haloalkoxy, $C_2$-$C_6$alkynyl and phenyl.

Embodiment IK16 provides compounds according to any one of embodiments IK1, IK2, IK3, IK4, IK5, IK6, IK7, IK8, IK9, IK10, IK11, IK12, IK13, IK14 or IK15 wherein X is N-methyl or O.

Embodiment IK17 provides compounds according to any one of embodiments IK1, IK2, IK3, IK4, IK5, IK6, IK7, IK8, IK9, IK10, IK11, IK12, IK13, IK14, IK15 or IK16 wherein $R^1$ is methyl and $R^2$ is ethyl.

Embodiment IK18 provides compounds according to any one of embodiments IK1, IK2, IK3, IK4, IK5, IK6, IK7, IK8, IK9, IK10, IK11, IK12, IK13, IK14, IK15, IK16 or IK17 wherein $R^3$ is hydrogen or methyl.

Embodiment IK19 provides compounds according to any one of embodiments IK1, IK2, IK3, IK4, IK5, IK6, IK7, IK8, IK9, IK10, IK11, IK12, IK13, IK14, IK15, IK16, IK17 or IK18 wherein $R^4$ is methyl.

Embodiment IK20 provides compounds according to any one of embodiments IK1, IK2, IK3, IK4, IK5, IK6, IK7, IK8, IK9, IK10, IK11, IK12, IK13, IK14, IK15, IK16, IK17, IK18 or IK19 wherein $R^5$ is $C_1$-$C_2$haloalkyl (especially $C_1$-$C_2$fluoroalkyl) and $R^6$ is phenyl (optionally substituted by one or two halogen atoms, preferably fluoro), n-butyl or $C_1$-$C_2$fluoroalkyl.

Embodiment IK21 provides compounds according to any one of embodiments IK1, IK2, IK3, IK4, IK5, IK6, IK7, IK8, IK9, IK10, IK11, IK12, IK13, IK14, IK15, IK16, IK17, IK18, IK19 or IK20 wherein $R^3$ is hydrogen and $R^4$ is methyl or $R^3$ is methyl and $R^4$ is methyl.

Embodiment IK22 provides compounds according to any one of embodiments IK1, IK2, IK3, IK4, IK5, IK6, IK7, IK8, IK9, IK10, IK11, IK12, IK13, IK14, IK15, IK16, IK17, IK18, IK19, IK20 or IK21 wherein both of $R^3$ and $R^4$ are methyl.

A preferred group of compounds of formula (IK) are those of formula (IK-1) which are compounds of formula (IK) wherein $R^1$ and $R^2$ are each independently $C_1$-$C_4$alkyl; $R^3$ is hydrogen or $C_1$-$C_4$alkyl; $R^4$ is $C_1$-$C_3$alkyl or $C_1$-$C_3$haloalkyl; $R^5$ and $R^6$ are each independently selected from $C_1$-$C_4$alkyl, $C_1$-$C_4$haloalkyl, $C_3$-$C_8$cycloalkyl, $C_2$-$C_6$alkynyl, phenyl (optionally substituted with one to three $R^7$ groups) and pyridyl (optionally substituted with one to three $R^7$ groups); X is $NR^8$ or O; each $R^7$ is independently selected from halogen, cyano, $C_1$-$C_4$alkyl, $C_1$-$C_4$haloalkyl, $C_3$-$C_6$cycloalkyl, $C_1$-$C_4$alkoxy, $C_1$-$C_4$haloalkoxy, $C_3$-$C_6$cycloalkoxy, $C_1$-$C_4$alkylthio, $C_1$-$C_4$alkylsulfonyl, $C_1$-$C_4$haloalkylsulfonyl, $C_1$-$C_4$alkylcarbonyl, $C_2$-$C_6$alkenyl, $C_2$-$C_6$haloalkenyl, $C_2$-$C_6$alkynyl, phenyl, benzyl, phenoxy, pyridyl, pyridylmethyl and pyridyloxy; and $R^8$ is hydrogen, $C_1$-$C_4$ alkyl or $C_1$-$C_4$ alkoxy; or a salt or N-oxide thereof.

A further preferred group of compounds of formula (IK) are those of formula (IK-2) which are compounds of formula (IK) wherein $R^1$ and $R^2$ are each independently selected from methyl, ethyl and isopropyl; $R^3$ is hydrogen or $C_1$-$C_3$alkyl; $R^4$ is $C_1$-$C_2$alkyl or $C_1$-$C_2$haloalkyl; $R^5$ and $R^6$ are each independently $C_1$-$C_4$alkyl, $C_1$-$C_4$haloalkyl, phenyl (optionally substituted with one or two $R^7$ groups) or pyridyl (optionally substituted with one or two $R^7$ groups); X is N—$C_1$-$C_4$alkyl or O; and each $R^7$ is independently selected from halogen, cyano, $C_1$-$C_4$alkyl, $C_1$-$C_4$haloalkyl, $C_3$-$C_6$cycloalkyl, $C_1$-$C_4$alkoxy, $C_1$-$C_4$haloalkoxy, $C_1$-$C_4$alkylthio, $C_1$-$C_4$alkylsulfonyl, $C_1$-$C_4$alkylcarbonyl, $C_2$-$C_6$alkynyl, aryl, aryloxy and heteroaryl; or a salt or N-oxide thereof.

A further preferred group of compounds of formula (IK) are those of formula (IK-3) which are compounds of formula (IK) wherein $R^1$ is methyl and $R^2$ is ethyl or isopropyl; or, alternatively, $R^1$ and $R^2$ are both ethyl; $R^3$ is hydrogen or methyl (preferably methyl); $R^4$ is methyl; $R^5$ is $CF_3$, $CClF_2$ or $CF_2CF_3$ (preferably $CF_3$); $R^6$ is phenyl (optionally substituted by one methyl group and/or one or two halogen atoms, preferably fluoro or chloro), n-propyl, i-propyl, n-butyl, iso-butyl or neo-pentyl; or, alternatively, $R^6$ is cyclopropyl; and X is O; or a salt or N-oxide thereof.

A further preferred group of compounds of formula (IK) are those of formula (IK-4) which are compounds of formula (IK) wherein $R^1$ and $R^2$ are each independently methyl or ethyl; $R^3$ is hydrogen or $C_1$-$C_2$ alkyl; $R^4$ is methyl or ethyl; $R^5$ and $R^6$ are each independently selected from $C_1$-$C_4$haloalkyl, phenyl (optionally substituted with one or two $R^7$ groups), n-propyl, n-butyl and pyridyl (optionally substituted with one or two $R^7$ groups); X is N-methyl or O; and each $R^7$ is independently selected from halogen, cyano, $C_1$-$C_4$alkyl, $C_1$-$C_4$haloalkyl, $C_1$-$C_4$alkoxy, $C_1$-$C_4$haloalkoxy, $C_2$-$C_6$alkynyl and phenyl; or a salt or N-oxide thereof.

Compounds according to the invention may possess any number of benefits including, inter alia, advantageous levels of biological activity for protecting plants against diseases that are caused by fungi or superior properties for use as agrochemical active ingredients (for example, greater biological activity, an advantageous spectrum of activity, an increased safety profile, improved physico-chemical properties, or increased biodegradability).

Specific examples of compounds of formula (I) are illustrated in the Tables 1 to 33 below.

Each of Tables 1 to 33, which follow the Table P below, make available 98 compounds of the formula (IA)

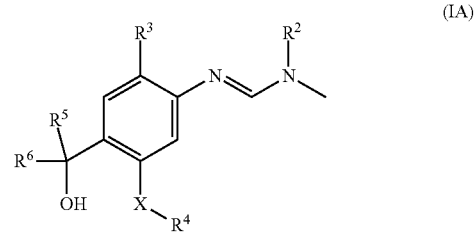

wherein $R^2$, $R^3$, $R^4$, $R^5$ and X are as defined in Table P and $R^6$ is as defined in Tables 1 to 33, respectively.

Thus Table 1 individualises 98 compounds of formula (IA) wherein for each row of Table P, $R^6$ is as defined in Table 1; similarly, Table 2 individualises 98 compounds of formula (IA) wherein for each row of Table P, $R^6$ is as defined in Table 2; and so on for Tables 3 to 33

TABLE P

| Compound No | $R^2$ | $R^3$ | X | $R^4$ | $R^5$ |
|---|---|---|---|---|---|
| P.001 | Me | Me | O | Me | Me |
| P.002 | Me | Me | O | Me | Et |
| P.003 | Me | Me | O | Me | $CClF_2$ |
| P.004 | Me | Me | O | Me | $CF_3$ |
| P.005 | Me | Me | O | Me | $CF_2CF_3$ |
| P.006 | Me | Me | O | Et | Me |
| P.007 | Me | Me | O | Et | Et |
| P.008 | Me | Me | O | Et | $CClF_2$ |
| P.009 | Me | Me | O | Et | $CF_3$ |
| P.010 | Me | Me | O | Et | $CF_2CF_3$ |
| P.011 | Me | Me | O | $CHF_2$ | Me |
| P.012 | Me | Me | O | $CHF_2$ | Et |
| P.013 | Me | Me | O | $CHF_2$ | $CClF_2$ |
| P.014 | Me | Me | O | $CHF_2$ | $CF_3$ |
| P.015 | Me | Me | O | $CHF_2$ | $CF_2CF_3$ |
| P.016 | Et | Cl | O | Me | $CClF_2$ |
| P.017 | Et | Cl | O | Me | $CF_3$ |
| P.018 | Et | Me | O | Me | Me |
| P.019 | Et | Me | O | Me | Et |
| P.020 | Et | Me | O | Me | $CClF_2$ |
| P.021 | Et | Me | O | Me | $CF_3$ |
| P.022 | Et | Me | O | Me | $CF_2CF_3$ |
| P.023 | Et | Me | O | Et | Me |
| P.024 | Et | Me | O | Et | Et |
| P.025 | Et | Me | O | Et | $CClF_2$ |
| P.026 | Et | Me | O | Et | $CF_3$ |
| P.027 | Et | Me | O | Et | $CF_2CF_3$ |
| P.028 | Et | Me | O | $CHF_2$ | Me |
| P.029 | Et | Me | O | $CHF_2$ | Et |
| P.030 | Et | Me | O | $CHF_2$ | $CClF_2$ |
| P.031 | Et | Me | O | $CHF_2$ | $CF_3$ |
| P.032 | Et | Me | O | $CHF_2$ | $CF_2CF_3$ |
| P.033 | Et | F | O | Me | $CF_3$ |
| P.034 | Et | F | O | Me | $CClF_2$ |
| P.035 | Et | F | O | Me | $CF_2CF_3$ |
| P.036 | Et | H | O | Me | $CF_3$ |
| P.037 | Et | H | O | Me | $CClF_2$ |
| P.038 | Et | H | O | Me | $CF_2CF_3$ |
| P.039 | Et | Me | O | Et | $CClF_2$ |

TABLE P-continued

| Compound No | R² | R³ | X | R⁴ | R⁵ |
|---|---|---|---|---|---|
| P.040 | Et | Me | O | Et | CF₃ |
| P.041 | Et | Me | O | Et | CF₂CF₃ |
| P.042 | Et | Me | O | Me | CClF₂ |
| P.043 | Et | Me | O | Me | CF₃ |
| P.044 | Et | Me | O | Me | CF₂CF₃ |
| P.045 | i-Pr | Me | O | Me | Me |
| P.046 | i-Pr | Me | O | Me | Et |
| P.047 | i-Pr | Me | O | Me | CClF₂ |
| P.048 | i-Pr | Me | O | Me | CF₃ |
| P.049 | i-Pr | Me | O | Me | CF₂CF₃ |
| P.050 | i-Pr | Me | O | Et | Me |
| P.051 | i-Pr | Me | O | Et | Et |
| P.052 | i-Pr | Me | O | Et | CClF₂ |
| P.053 | i-Pr | Me | O | Et | CF₃ |
| P.054 | i-Pr | Me | O | Et | CF₂CF₃ |
| P.055 | i-Pr | Me | O | CHF₂ | Me |
| P.056 | i-Pr | Me | O | CHF₂ | Et |
| P.057 | i-Pr | Me | O | CHF₂ | CClF₂ |
| P.058 | i-Pr | Me | O | CHF₂ | CF₃ |
| P.059 | i-Pr | Me | O | CHF₂ | CF₂CF₃ |
| P.060 | i-Pr | Me | S | Me | Me |
| P.061 | i-Pr | Me | S | Me | Et |
| P.062 | i-Pr | Me | S | Me | CClF₂ |
| P.063 | i-Pr | Me | S | Me | CF₃ |
| P.064 | i-Pr | Me | S | Me | CF₂CF₃ |
| P.065 | i-Pr | F | O | Me | CF₃ |
| P.066 | i-Pr | F | O | Me | CClF₂ |
| P.067 | i-Pr | F | O | Me | CF₂CF₃ |
| P.068 | i-Pr | H | O | Me | CF₃ |
| P.069 | i-Pr | H | O | Me | CClF₂ |
| P.070 | i-Pr | H | O | Me | CF₂CF₃ |
| P.071 | i-Pr | Cl | O | Me | CClF₂ |
| P.072 | i-Pr | Cl | O | Me | CF₃ |
| P.073 | n-Pr | Me | O | Me | CClF₂ |
| P.074 | n-Pr | Me | O | Me | CF₃ |
| P.075 | n-Pr | Me | O | Me | CF₂CF₃ |
| P.076 | n-Pr | H | O | Me | CClF₂ |
| P.077 | n-Pr | H | O | Me | CF₃ |
| P.078 | n-Pr | F | O | Me | CF₃ |
| P.079 | cyclopropyl | Me | O | Me | Me |
| P.080 | cyclopropyl | Me | O | Me | Et |
| P.081 | cyclopropyl | Me | O | Me | CClF₂ |
| P.082 | cyclopropyl | Me | O | Me | CF₃ |
| P.083 | cyclopropyl | Me | O | Me | CF₂CF₃ |
| P.084 | cyclopropyl | Me | O | Et | Me |
| P.085 | cyclopropyl | Me | O | Et | Et |
| P.086 | cyclopropyl | Me | O | Et | CClF₂ |
| P.087 | cyclopropyl | Me | O | Et | CF₃ |
| P.088 | cyclopropyl | Me | O | Et | CF₂CF₃ |
| P.089 | cyclopropyl | Me | O | CHF₂ | Me |
| P.090 | cyclopropyl | Me | O | CHF₂ | Et |
| P.091 | cyclopropyl | Me | O | CHF₂ | CClF₂ |
| P.092 | cyclopropyl | Me | O | CHF₂ | CF₃ |
| P.093 | cyclopropyl | Me | O | CHF₂ | CF₂CF₃ |
| P.094 | cyclopropyl | Me | S | Me | Me |
| P.095 | cyclopropyl | Me | S | Me | Et |
| P.096 | cyclopropyl | Me | S | Me | CClF₂ |
| P.097 | cyclopropyl | Me | S | Me | CF₃ |
| P.098 | cyclopropyl | Me | S | Me | CF₂CF₃ |

Table 1: This table discloses 98 compounds 1.001 to 1.098 of the formula IA wherein $R^6$ is

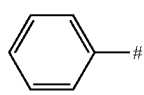

Wherein the hash mark indicates the point of attachment of $R^6$ to the rest of the molecule, and in which the variables $R^2$, $R^3$, $R^4$, $R^5$ and X have the specific meaning given in the corresponding line of Table P. For example, compound 1.001 has the following structure:

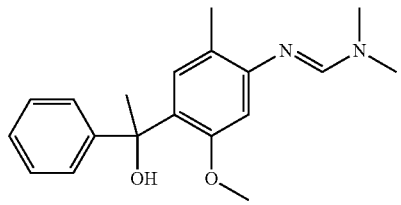

Table 2: This table discloses 98 compounds 2.001 to 2.098 of the formula IA wherein $R^6$ is

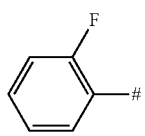

Wherein the hash mark indicates the point of attachment of $R^6$ to the rest of the molecule, and in which the variables $R^2$, $R^3$, $R^4$, $R^5$ and X have the specific meaning given in the corresponding line of Table P.

Table 3: This table discloses 98 compounds 3.001 to 3.098 of the formula IA wherein $R^6$ is

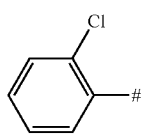

Wherein the hash mark indicates the point of attachment of $R^6$ to the rest of the molecule, and in which the variables $R^2$, $R^3$, $R^4$, $R^5$ and X have the specific meaning given in the corresponding line of Table P.

Table 4: This table discloses 98 compounds 4.001 to 4.098 of the formula IA wherein $R^6$ is

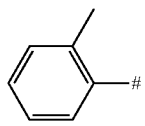

Wherein the hash mark indicates the point of attachment of $R^6$ to the rest of the molecule, and in which the variables $R^2$, $R^3$, $R^4$, $R^5$ and X have the specific meaning given in the corresponding line of Table P.

Table 5: This table discloses 98 compounds 5.001 to 5.098 of the formula IA wherein $R^6$ is

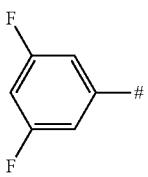

Wherein the hash mark indicates the point of attachment of $R^6$ to the rest of the molecule, and in which the variables $R^2$, $R^3$, $R^4$, $R^5$ and X have the specific meaning given in the corresponding line of Table P.

Table 6: This table discloses 98 compounds 6.001 to 6.098 of the formula IA wherein $R^6$ is

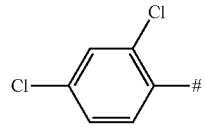

Wherein the hash mark indicates the point of attachment of $R^6$ to the rest of the molecule, and in which the variables $R^2$, $R^3$, $R^4$, $R^5$ and X have the specific meaning given in the corresponding line of Table P.

Table 7: This table discloses 98 compounds 7.001 to 7.098 of the formula IA wherein $R^6$ is

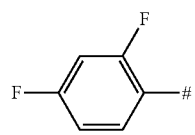

Wherein the hash mark indicates the point of attachment of $R^6$ to the rest of the molecule, and in which the variables $R^2$, $R^3$, $R^4$, $R^5$ and X have the specific meaning given in the corresponding line of Table P.

Table 8: This table discloses 98 compounds 8.001 to 8.098 of the formula IA wherein $R^6$ is

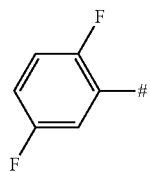

Wherein the hash mark indicates the point of attachment of $R^6$ to the rest of the molecule, and in which the variables $R^2$, $R^3$, $R^4$, $R^5$ and X have the specific meaning given in the corresponding line of Table P.

Table 9: This table discloses 98 compounds 9.001 to 9.098 of the formula IA wherein $R^6$ is

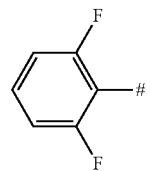

Wherein the hash mark indicates the point of attachment of $R^6$ to the rest of the molecule, and in which the variables $R^2$, $R^3$, $R^4$, $R^5$ and X have the specific meaning given in the corresponding line of Table P.

Table 10: This table discloses 98 compounds 10.001 to 10.098 of the formula IA wherein $R^6$ is

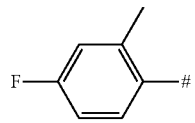

Wherein the hash mark indicates the point of attachment of $R^6$ to the rest of the molecule, and in which the variables $R^2$, $R^3$, $R^4$, $R^5$ and X have the specific meaning given in the corresponding line of Table P.

Table 11: This table discloses 98 compounds 11.001 to 11.098 of the formula IA wherein $R^6$ is

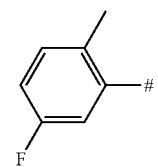

Wherein the hash mark indicates the point of attachment of $R^6$ to the rest of the molecule, and in which the variables $R^2$, $R^3$, $R^4$, $R^5$ and X have the specific meaning given in the corresponding line of Table P.

Table 12: This table discloses 98 compounds 12.001 to 11.098 of the formula IA wherein $R^6$ is

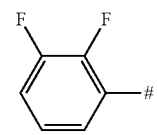

Wherein the hash mark indicates the point of attachment of $R^6$ to the rest of the molecule, and in which the variables $R^2$, $R^3$, $R^4$, $R^5$ and X have the specific meaning given in the corresponding line of Table P.

Table 13: This table discloses 98 compounds 13.001 to 13.098 of the formula IA wherein $R^6$ is

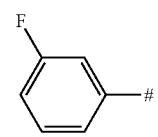

Wherein the hash mark indicates the point of attachment of $R^6$ to the rest of the molecule, and in which the variables $R^2$, $R^3$, $R^4$, $R^5$ and X have the specific meaning given in the corresponding line of Table P.

Table 14: This table discloses 98 compounds 14.001 to 14.098 of the formula IA wherein $R^6$ is

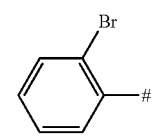

Wherein the hash mark indicates the point of attachment of $R^6$ to the rest of the molecule, and in which the variables $R^2$, $R^3$, $R^4$, $R^5$ and X have the specific meaning given in the corresponding line of Table P.

Table 15: This table discloses 98 compounds 15.001 to 15.098 of the formula IA wherein $R^6$ is

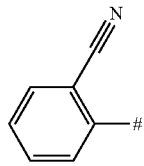

Wherein the hash mark indicates the point of attachment of $R^6$ to the rest of the molecule, and in which the variables $R^2$, $R^3$, $R^4$, $R^5$ and X have the specific meaning given in the corresponding line of Table P.

Table 16: This table discloses 98 compounds 16.001 to 16.098 of the formula IA wherein $R^6$ is

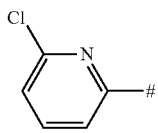

Wherein the hash mark indicates the point of attachment of $R^6$ to the rest of the molecule, and in which the variables $R^2$, $R^3$, $R^4$, $R^5$ and X have the specific meaning given in the corresponding line of Table P.

Table 17: This table discloses 98 compounds 17.001 to 17.098 of the formula IA wherein $R^6$ is

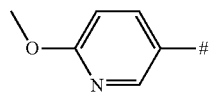

Wherein the hash mark indicates the point of attachment of $R^6$ to the rest of the molecule, and in which the variables $R^2$, $R^3$, $R^4$, $R^5$ and X have the specific meaning given in the corresponding line of Table P.

Table 18: This table discloses 98 compounds 18.001 to 18.098 of the formula IA wherein $R^6$ is

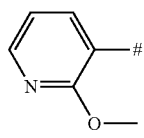

Wherein the hash mark indicates the point of attachment of $R^6$ to the rest of the molecule, and in which the variables $R^2$, $R^3$, $R^4$, $R^5$ and X have the specific meaning given in the corresponding line of Table P.

Table 19: This table discloses 98 compounds 19.001 to 19.098 of the formula IA wherein $R^6$ is

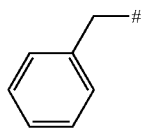

Wherein the hash mark indicates the point of attachment of $R^6$ to the rest of the molecule, and in which the variables $R^2$, $R^3$, $R^4$, $R^5$ and X have the specific meaning given in the corresponding line of Table P.

Table 20: This table discloses 98 compounds 20.001 to 20.098 of the formula IA wherein $R^6$ is

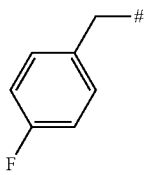

Wherein the hash mark indicates the point of attachment of $R^6$ to the rest of the molecule, and in which the variables $R^2$, $R^3$, $R^4$, $R^5$ and X have the specific meaning given in the corresponding line of Table P.

Table 21: This table discloses 98 compounds 21.001 to 21.098 of the formula IA wherein $R^6$ is

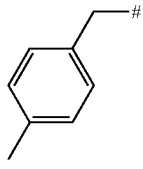

Wherein the hash mark indicates the point of attachment of $R^6$ to the rest of the molecule, and in which the variables $R^2$, $R^3$, $R^4$, $R^5$ and X have the specific meaning given in the corresponding line of Table P.

Table 22: This table discloses 98 compounds 22.001 to 22.098 of the formula IA wherein $R^6$ is

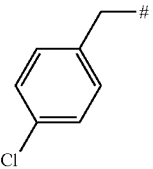

Wherein the hash mark indicates the point of attachment of $R^6$ to the rest of the molecule, and in which the variables $R^2$, $R^3$, $R^4$, $R^5$ and X have the specific meaning given in the corresponding line of Table P.

Table 23: This table discloses 98 compounds 23.001 to 23.098 of the formula IA wherein $R^6$ is

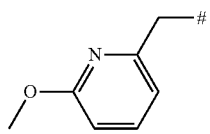

Wherein the hash mark indicates the point of attachment of $R^6$ to the rest of the molecule, and in which the variables $R^2$, $R^3$, $R^4$, $R^5$ and X have the specific meaning given in the corresponding line of Table P.

Table 24: This table discloses 98 compounds 24.001 to 24.098 of the formula IA wherein $R^6$ is ethyl, and in which the variables $R^2$, $R^3$, $R^4$, $R^5$ and X have the specific meaning given in the corresponding line of Table P. For example, compound 24.021 has the following structure:

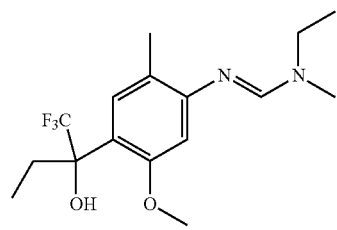 [SMILES: CCN(C)/C=N/c1cc(OC)c(C(O)(CC)C(F)(F)F)cc1C]

Table 25: This table discloses 98 compounds 25.001 to 25.098 of the formula IA wherein $R^6$ is propyl, and in which the variables $R^2$, $R^3$, $R^4$, $R^5$ and X have the specific meaning given in the corresponding line of Table P. For example, compound 25.021 has the following structure:

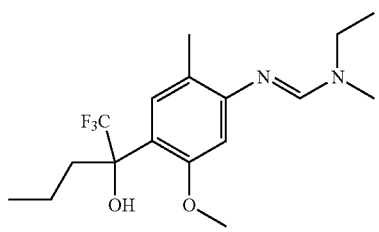 [SMILES: CCCC(O)(c1cc(C)c(/N=C/N(C)CC)cc1OC)C(F)(F)F]

Table 26: This table discloses 98 compounds 26.001 to 26.098 of the formula IA wherein $R^6$ is butyl, and in which the variables $R^2$, $R^3$, $R^4$, $R^5$ and X have the specific meaning given in the corresponding line of Table P. For example, compound 26.021 has the following structure:

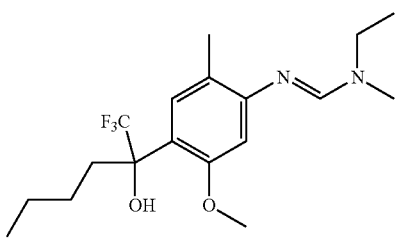 [SMILES: CCCCC(O)(c1cc(C)c(/N=C/N(C)CC)cc1OC)C(F)(F)F]

Table 27: This table discloses 98 compounds 27.001 to 27.098 of the formula IA wherein $R^6$ is —CH$_2$CH(CH$_3$)$_2$, and in which the variables $R^2$, $R^3$, $R^4$, $R^5$ and X have the specific meaning given in the corresponding line of Table P. For example, compound 27.021 has the following structure:

Table 28: This table discloses 98 compounds 28.001 to 28.098 of the formula IA wherein $R^6$ is cyclohexyl, and in which the variables $R^2$, $R^3$, $R^4$, $R^5$ and X have the specific meaning given in the corresponding line of Table P. For example, compound 28.021 has the following structure:

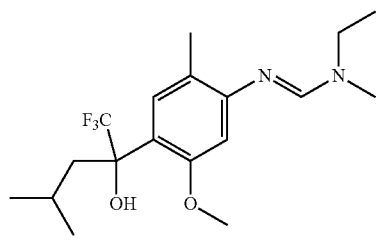 [SMILES: CCN(C)/C=N/c1cc(OC)c(C(O)(CC(C)C)C(F)(F)F)cc1C]

Table 29: This table discloses 98 compounds 29.001 to 29.098 of the formula IA wherein $R^6$ is isopropyl, and in which the variables $R^2$, $R^3$, $R^4$, $R^5$ and X have the specific meaning given in the corresponding line of Table P. For example, compound 29.021 has the following structure:

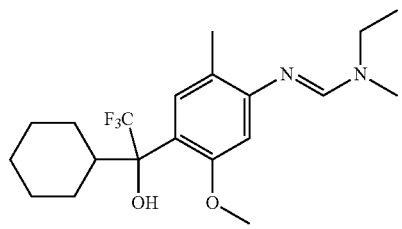 [SMILES: CCN(C)/C=N/c1cc(OC)c(C(O)(C2CCCCC2)C(F)(F)F)cc1C]

Table 30: This table discloses 98 compounds 30.001 to 30.098 of the formula IA wherein $R^6$ is cyclopentyl, and in which the variables $R^2$, $R^3$, $R^4$, $R^5$ and X have the specific meaning given in the corresponding line of Table P. For example, compound 30.021 has the following structure:

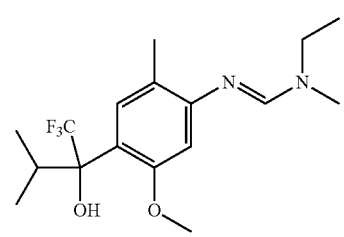 [SMILES: CCN(C)/C=N/c1cc(OC)c(C(O)(C(C)C)C(F)(F)F)cc1C]

Table 31: This table discloses 98 compounds 31.001 to 31.098 of the formula IA wherein $R^6$ is cyclopropyl, and in which the variables $R^2$, $R^3$, $R^4$, $R^5$ and X have the specific meaning given in the corresponding line of Table P. For example, compound 31.021 has the following structure:

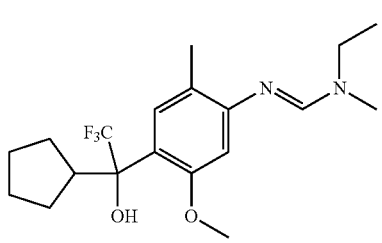 [SMILES: CCN(C)/C=N/c1cc(OC)c(C(O)(C2CCCC2)C(F)(F)F)cc1C]

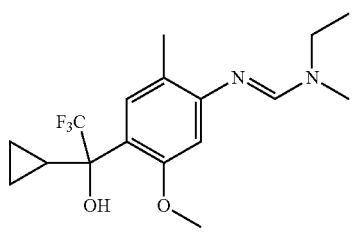 [SMILES: CCN(C)/C=N/c1cc(OC)c(C(O)(C2CC2)C(F)(F)F)cc1C]

Table 32: This table discloses 98 compounds 32.001 to 32.098 of the formula IA wherein $R^6$ is —$(CH_2)C(CH_3)_3$, and in which the variables $R^2$, $R^3$, $R^4$, $R^5$ and X have the specific meaning given in the corresponding line of Table P. For example, compound 32.021 has the following structure:

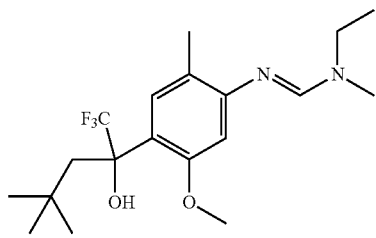 [SMILES: CCN(C)/C=N/c1cc(OC)c(C(O)(CC(C)(C)C)C(F)(F)F)cc1C]

Table 33: This table discloses 98 compounds 33.001 to 33.098 of the formula IA wherein $R^6$ is allyl, and in which the variables $R^2$, $R^3$, $R^4$, $R^5$ and X have the specific meaning given in the corresponding line of Table P. For example, compound 33.021 has the following structure:

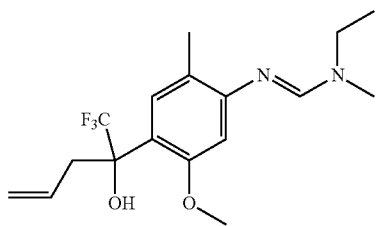

Compounds of the present invention can be made as shown in the following schemes, in which, unless otherwise stated, the definition of each variable is as defined above for a compound of formula (I).

The compounds of formula (I), wherein $R^1$, $R^2$, $R^3$, $R^4$, $R^5$, $R^6$ and X are as defined for formula (I), can be obtained by transformation of a compound of formula (II), wherein $R^1$, $R^2$, $R^3$, $R^4$ and X are as defined for formula (I) and Hal is halogen, preferably bromo or iodo, with a compound of formula (III), wherein $R^5$ and $R^6$ are as defined for formula (I), and a strong base such as n-butyl lithium or tert-butyl lithium. This is shown in Scheme 1 below.

Scheme 1

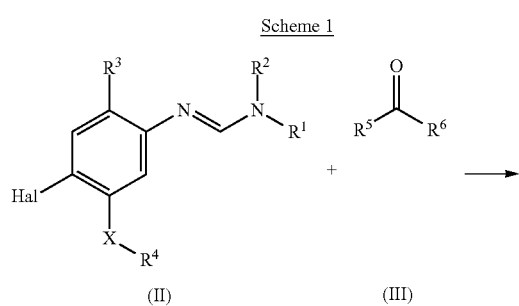

The compounds of formula (II), wherein $R^1$, $R^2$, $R^3$, $R^4$ and X are as defined for formula (I)) and Hal is halogen, preferably bromo or iodo, can be obtained by transformation of a compound of formula (IV), wherein $R^3$, $R^4$ and X are as defined for formula (I)) and Hal is halogen, preferably bromo or iodo, with a compound of formula (V), wherein W and $R^2$ are as defined for formula (I) and $R^9$ is $C_1$-$C_4$alkyl. This is shown in Scheme 2 below.

Scheme 2

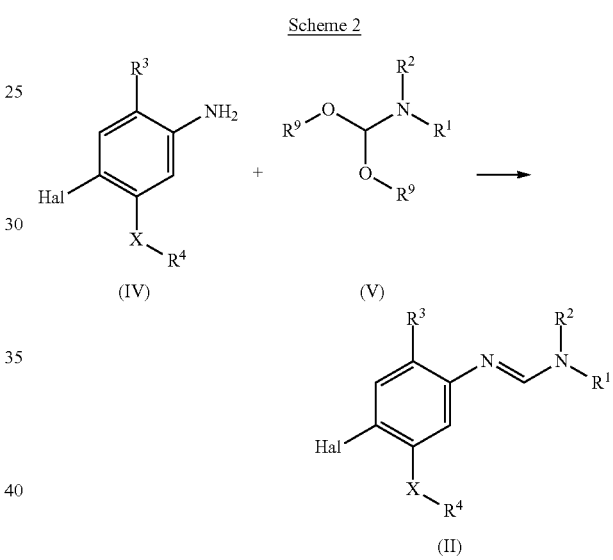

The compounds of formula (IV), wherein $R^3$, $R^4$ and X are as defined for formula (I) and Hal is halogen, preferably bromo or iodo, can be obtained by transformation of a compound of formula (VI), wherein $R^3$, $R^4$ and X are as defined for formula (I) with a halogenation agent, such as bromine, N-bromosuccinimide or N-iodosuccinimide. This is shown in Scheme 3 below.

Scheme 3

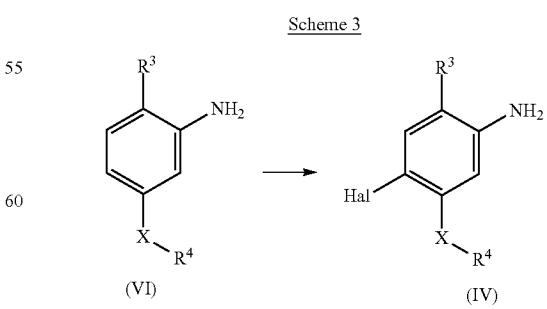

The compounds of formula (VI), wherein $R^3$, $R^4$ and X are as defined for formula (I), can be obtained by transformation of a compound of formula (VII), wherein $R^3$, $R^4$ and X are as defined for formula (I), under reductive conditions, e.g. by catalytic hydrogenation or under conditions of the Bechamp reaction. This is shown in Scheme 4 below.

Scheme 4

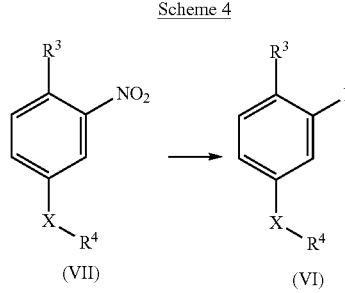

The compounds of formula (VII-A), wherein $R^3$ and $R^4$ are as defined for formula (I), can be obtained by transformation of a compound of formula (VIII), wherein $R^3$ is as defined for formula (I), with a compound of formula (IX), wherein $R^4$ is as defined for formula (I) and $R^{10}$ is halogen, preferably chloro or bromo, or a sulfonate, preferably a mesylate, and with a base such as sodium hydride or potassium carbonate. This is shown in Scheme 5 below.

Scheme 5

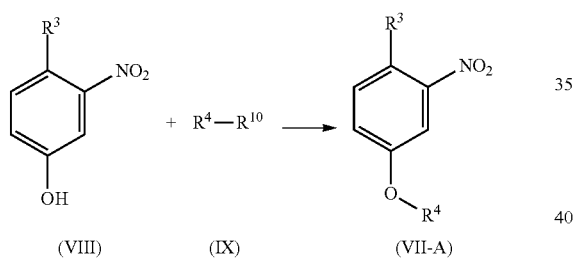

The compounds of formula (VII-B), wherein W and $R^4$ are as defined for formula (I), can be obtained by transformation of a compound of formula (X), wherein $R^3$ is as defined for formula (I), with a compound of formula (IX), wherein $R^4$ is as defined for formula (I), and $R^{10}$ is halogen, preferably chloro or bromo, or a sulfonate, preferably a mesylate, and with a base such as sodium hydride or potassium carbonate This is shown in Scheme 6 below.

Scheme 6

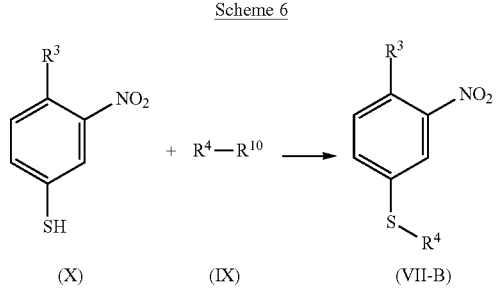

Alternatively the compounds of formula (I), wherein $R^1$, $R^2$, $R^3$, $R^4$, $R^5$, $R^6$ and X are as defined for formula (I), can be obtained by transformation of a compound of formula (XI), wherein $R^3$, $R^4$, $R^5$, $R^6$ and X are as defined for formula (I), with a compound of formula (V), wherein $R^1$ and $R^2$ are as defined for formula (I) and $R^9$ is $C_1$-$C_4$alkyl. This is shown in Scheme 7 below.

Scheme 7

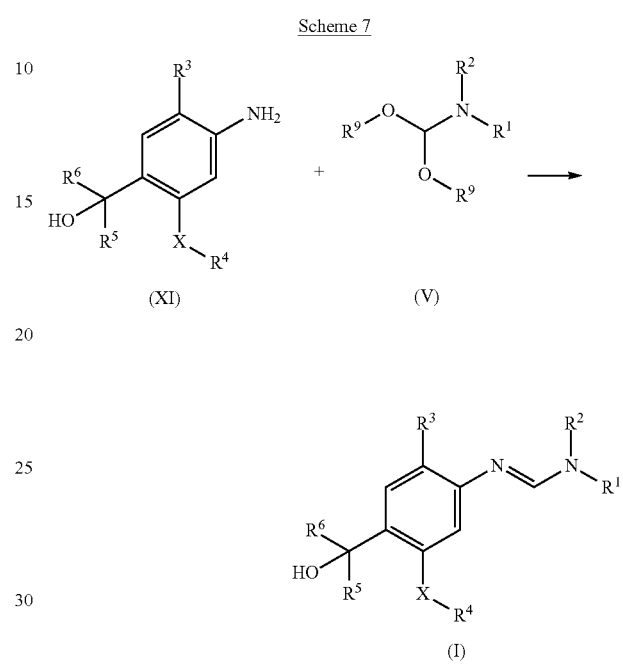

The compounds of formula (XI), wherein $R^3$, $R^4$, $R^5$, $R^6$ and X are as defined for formula (I) can be obtained by transformation of a compound of formula (XII), wherein $R^3$, $R^4$, $R^5$, $R^6$ and X are as defined for formula (I) under reductive conditions, e.g. by catalytic hydrogenation or under conditions of the Bechamp reaction. This is shown in Scheme 8 below.

Scheme 8

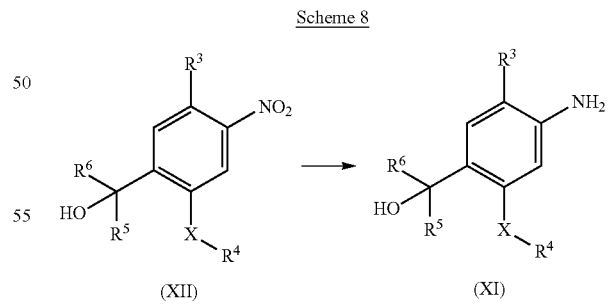

The compounds of formula (XII), wherein $R^3$, $R^4$, $R^5$, $R^6$ and X are as defined for formula (I) can be obtained by transformation of a compound of formula (XIII), wherein $R^3$, $R^4$, $R^5$ and X are as defined for formula (I), with a compound of formula (XIV), wherein $R^6$ is as defined for formula (I) and $R^{11}$ is Li, MgCl or MgBr. This is shown in Scheme 9 below.

Scheme 9

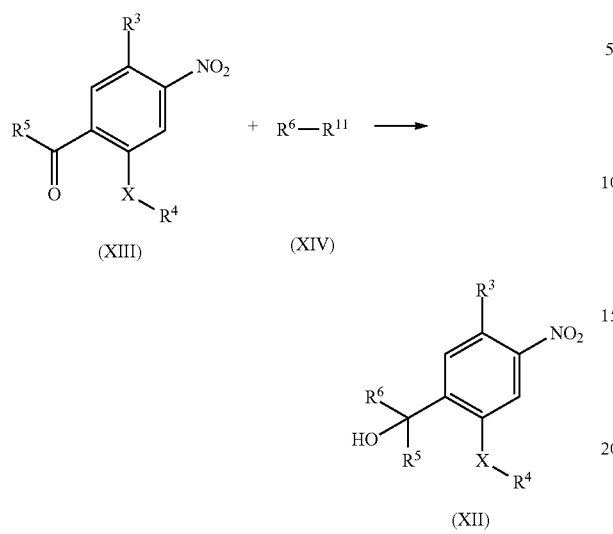

The compounds of formula (XIII-A), wherein $R^3$, $R^4$ and $R^5$ are as defined for formula (I) can be obtained by transformation of a compound of formula (XV), wherein W and $R^5$ are as defined for formula (I), with a compound of formula (IX), wherein $R^4$ is as defined for formula (I) and $R^{10}$ is halogen, preferably chloro or bromo, or a sulfonate, preferably a mesylate, and with a base such as sodium hydride or potassium carbonate. This is shown in Scheme 10 below.

Scheme 10

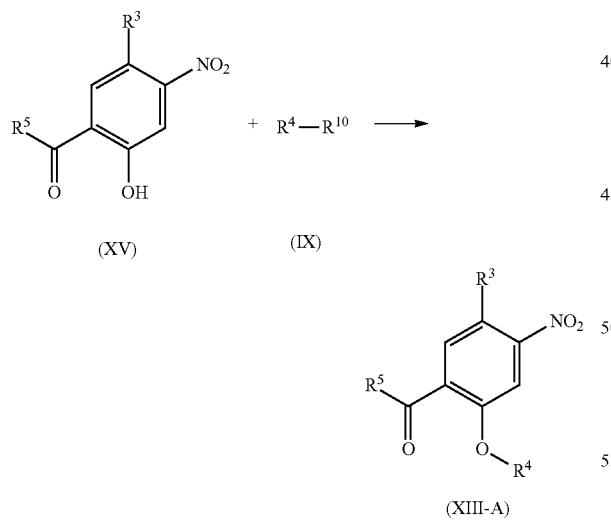

The compounds of formula (XV), wherein $R^3$ and $R^5$ are as defined for formula (I) can be obtained by transformation of a compound of formula (XVI), wherein $R^3$ is as defined for formula (I), with a compound of formula (XVII), wherein $R^5$ is as defined for formula (I) and $R^{12}$ is hydroxyl or halogen, preferably chloro, and a Lewis acid, such as iron(III) chloride or aluminium(III) chloride. This is shown in Scheme 11 below.

Scheme 11

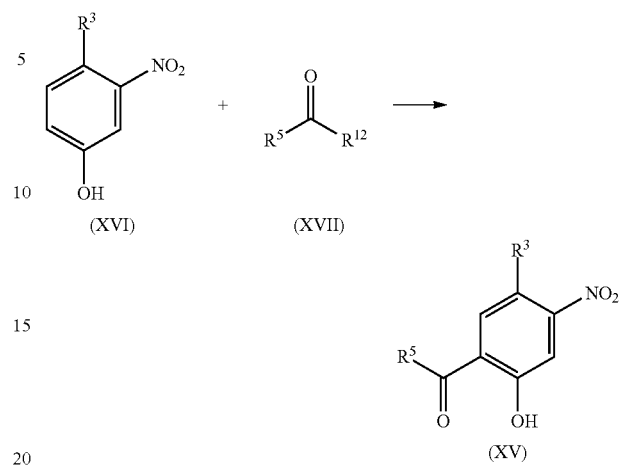

The compounds of formula (XVIII), wherein $R^3$, $R^4$ and X are as defined for formula (I) can be obtained by transformation of a compound of formula (VI), wherein $R^3$, $R^4$ and X are as defined for formula (I), with a compound of formula (XIX) under acidic conditions, e.g. with the aid of p-toluenesulfonic acid. This is shown in Scheme 12 below.

Scheme 12

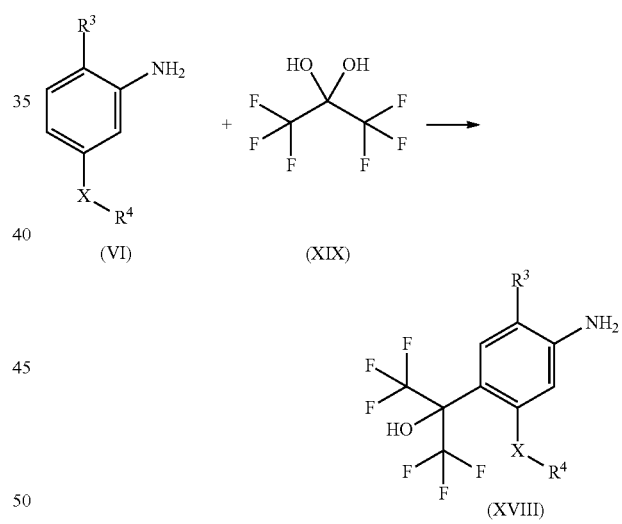

Certain intermediates described in the above schemes are novel and as such form a further aspect of the invention.

The compounds of formula (I) can be used in the agricultural sector and related fields of use e.g. as active ingredients for controlling plant pests or on non-living materials for control of spoilage microorganisms or organisms potentially harmful to man. The novel compounds are distinguished by excellent activity at low rates of application, by being well tolerated by plants and by being environmentally safe. They have very useful curative, preventive and systemic properties and may be used for protecting numerous cultivated plants. The compounds of formula (I) can be used to inhibit or destroy the pests that occur on plants or parts of plants (fruit, blossoms, leaves, stems, tubers, roots) of different crops of useful plants, while at the same time protecting also those parts of the plants that grow later e.g. from phytopathogenic microorganisms.

It is also possible to use compounds of formula (I) as fungicide. The term "fungicide" as used herein means a compound that controls, modifies, or prevents the growth of fungi. The term "fungicidally effective amount" means the quantity of such a compound or combination of such compounds that is capable of producing an effect on the growth of fungi. Controlling or modifying effects include all deviation from natural development, such as killing, retardation and the like, and prevention includes barrier or other defensive formation in or on a plant to prevent fungal infection.

It is also possible to use compounds of formula (I) as dressing agents for the treatment of plant propagation material, e.g., seed, such as fruits, tubers or grains, or plant cuttings (for example rice), for the protection against fungal infections as well as against phytopathogenic fungi occurring in the soil. The propagation material can be treated with a composition comprising a compound of formula (I) before planting: seed, for example, can be dressed before being sown. The compounds of formula (I) can also be applied to grains (coating), either by impregnating the seeds in a liquid formulation or by coating them with a solid formulation. The composition can also be applied to the planting site when the propagation material is being planted, for example, to the seed furrow during sowing. The invention relates also to such methods of treating plant propagation material and to the plant propagation material so treated.

Furthermore the compounds according to present invention can be used for controlling fungi in related areas, for example in the protection of technical materials, including wood and wood related technical products, in food storage, in hygiene management.

In addition, the invention could be used to protect non-living materials from fungal attack, e.g. lumber, wall boards and paint.

Compounds of formula (I) and fungicidal compositions containing them may be used to control plant diseases caused by a broad spectrum of fungal plant pathogens. They are effective in controlling a broad spectrum of plant diseases, such as foliar pathogens of ornamental, turf, vegetable, field, cereal, and fruit crops.

These fungi and fungal vectors of disease, as well as phytopathogenic bacteria and viruses, which may be controlled are for example:

*Absidia corymbifera, Alternaria* spp, *Aphanomyces* spp, *Ascochyta* spp, *Aspergillus* spp. including *A. flavus, A. fumigatus, A. nidulans, A. niger, A. terrus, Aureobasidium* spp. including *A. pullulans, Blastomyces dermatitidis, Blumeria graminis, Bremia lactucae, Botryosphaeria* spp. including *B. dothidea, B. obtusa, Botrytis* spp. including *B. cinerea, Candida* spp. including *C. albicans, C. glabrata, C. krusei, C. lusitaniae, C. parapsilosis, C. tropicalis, Cephaloascus fragrans, Ceratocystis* spp, *Cercospora* spp. including *C. arachidicola, Cercosporidium personatum, Cladosporium* spp, *Claviceps purpurea,*

*Coccidioides immitis, Cochliobolus* spp, *Colletotrichum* spp. including *C. musae,*

*Cryptococcus neoformans, Diaporthe* spp, *Didymella* spp, *Drechslera* spp, *Elsinoe* spp,

*Epidermophyton* spp, *Erwinia amylovora, Erysiphe* spp. including *E. cichoracearum,*

*Eutypa lata, Fusarium* spp. including *F. culmorum, F. graminearum, F. langsethiae, F. moniliforme, F. oxysporum, F. proliferatum, F. subglutinans, F. solani, Gaeumannomyces graminis, Gibberella fujikuroi, Gloeodes pomigena, Gloeosporium musarum, Glomerella cingulate, Guignardia bidwellii, Gymnosporangium juniperi-virginianae, Helminthosporium* spp, *Hemileia* spp, *Histoplasma* spp. including *H. capsulatum, Laetisaria fuciformis, Leptographium lindbergi, Leveillula taurica, Lophodermium seditiosum, Microdochium nivale, Microsporum* spp, *Monilinia* spp, *Mucor* spp, *Mycosphaerella* spp. including *M. graminicola, M. pomi, Oncobasidium theobromaeon, Ophiostoma piceae, Paracoccidioides* spp, *Penicillium* spp. including *P. digitatum, P. italicum, Petriellidium* spp, *Peronosclerospora* spp. Including *P. maydis, P. philippinensis* and *P. sorghi, Peronospora* spp, *Phaeosphaeria nodorum, Phakopsora pachyrhizi, Phellinus igniarus, Phialophora* spp, *Phoma* spp, *Phomopsis viticola, Phytophthora* spp. including *P. infestans, Plasmopara* spp. including *P. halstedii, P. viticola, Pleospora* spp., *Podosphaera* spp. including *P. leucotricha, Polymyxa graminis, Polymyxa betae, Pseudocercosporella herpotrichoides, Pseudomonas* spp, *Pseudoperonospora* spp. including *P. cubensis, P. humuli, Pseudopeziza tracheiphila, Puccinia* Spp. including *P. hordei, P. recondita, P. striiformis, P. triticina, Pyrenopeziza* spp, *Pyrenophora* spp, *Pyricularia* spp. including *P. oryzae, Pythium* spp. including *P. ultimum, Ramularia* spp, *Rhizoctonia* spp, *Rhizomucor pusillus, Rhizopus arrhizus, Rhynchosporium* spp, *Scedosporium* spp. including *S. apiospermum* and *S. prolificans, Schizothyrium pomi,*

*Sclerotinia* spp, *Sclerotium* spp, *Septoria* spp, including *S. nodorum, S. tritici, Sphaerotheca macularis, Sphaerotheca fusca (Sphaerotheca fuliginea), Sporothorix* spp, *Stagonospora nodorum, Stemphylium* spp, *Stereum hirsutum, Thanatephorus cucumeris, Thielaviopsis basicola, Tilletia* spp, *Trichoderma* spp. including *T. harzianum, T. pseudokoningii, T. viride,*

*Trichophyton* spp, *Typhula* spp, *Uncinula necator, Urocystis* spp, *Ustilago* spp, *Venturia* spp. including *V. inaequalis, Verticillium* spp, and *Xanthomonas* spp.

In particular, compounds of formula (I) and fungicidal compositions containing them may be used to control plant diseases caused by a broad spectrum of fungal plant pathogens in the Basidiomycete, Ascomycete, Oomycete and/or Deuteromycete, Blasocladiomycete, Chrytidiomycete, Glomeromycete and/or Mucoromycete classes.

These pathogens may include:

Oomycetes, including *Phytophthora* diseases such as those caused by *Phytophthora capsici, Phytophthora infestans, Phytophthora sojae, Phytophthora fragariae, Phytophthora nicotianae, Phytophthora cinnamomi, Phytophthora citricola, Phytophthora citrophthora* and *Phytophthora erythroseptica; Pythium* diseases such as those caused by *Pythium aphanidermatum, Pythium arrhenomanes, Pythium graminicola, Pythium irregulare* and *Pythium ultimum*; diseases caused by Peronosporales such as *Peronospora destructor, Peronospora parasitica, Plasmopara viticola, Plasmopara halstedii, Pseudoperonospora cubensis, Albugo candida, Sclerophthora macrospora* and *Bremia lactucae*; and others such as *Aphanomyces cochlioides, Labyrinthula zosterae, Peronosclerospora sorghi* and *Sclerospora graminicola.*

Ascomycetes, including blotch, spot, blast or blight diseases and/or rots for example those caused by Pleosporales such as *Stemphylium solani, Stagonospora tainanensis, Spilocaea oleaginea, Setosphaeria turcica, Pyrenochaeta lycoperisici, Pleospora herbarum, Phoma destructiva, Phaeosphaeria herpotrichoides, Phaeocryptocus gaeumannii, Ophiosphaerella graminicola, Ophiobolus graminis, Leptosphaeria maculans, Hendersonia creberrima, Helminthosporium triticirepentis, Setosphaeria turcica, Drechslera glycines, Didymella bryoniae, Cycloconium oleagineum,*

*Corynespora cassiicola, Cochliobolus sativus, Bipolaris cactivora, Venturia inaequalis, Pyrenophora teres, Pyrenophora tritici-repentis, Alternaria alternata, Alternaria brassicicola, Alternaria solani* and *Alternaria tomatophila*, Capnodiales such as *Septoria tritici, Septoria nodorum, Septoria glycines, Cercospora arachidicola, Cercospora sojina, Cercospora zeae-maydis, Cercosporella capsellae* and *Cercosporella herpotrichoides, Cladosporium carpophilum, Cladosporium effusum, Passalora fulva, Cladosporium oxysporum, Dothistroma septosporum, Isariopsis clavispora, Mycosphaerella fijiensis, Mycosphaerella graminicola, Mycovellosiella koepkeii, Phaeoisariopsis bataticola, Pseudocercospora vitis, Pseudocercosporella herpotrichoides, Ramularia beticola, Ramularia collocygni*, Magnaporthales such as *Gaeumannomyces graminis, Magnaporthe grisea, Pyricularia oryzae, Diaporthales* such as *Anisogramma anomala, Apiognomonia errabunda, Cytospora platani, Diaporthe phaseolorum, Discula destructiva, Gnomonia fructicola, Greeneria uvicola, Melanconium juglandinum, Phomopsis viticola, Sirococcus clavigignenti-juglandacearum, Tubakia dryina, Dicarpella* spp., *Valsa ceratosperma*, and others such as *Actinothyrium graminis, Ascochyta pisi, Aspergillus flavus, Aspergillus fumigatus, Aspergillus nidulans, Asperisporium caricae, Blumeriella jaapii, Candida* spp., *Capnodium ramosum, Cephaloascus* spp., *Cephalosporium gramineum, Ceratocystis paradoxa, Chaetomium* spp., *Hymenoscyphus pseudoalbidus, Coccidioides* spp., *Cylindrosporium padi, Diplocarpon malae, Drepanopeziza campestris, Elsinoe ampelina, Epicoccum nigrum, Epidermophyton* spp., *Eutypa lata, Geotrichum candidum, Gibeffina cerealis, Gloeocercospora sorghi, Gloeodes pomigena, Gloeosporium perennans; Gloeotinia temulenta, Griphospaeria corticola, Kabatiella lini, Leptographium microsporum, Leptosphaerulinia crassiasca, Lophodermium seditiosum, Marssonina graminicola, Microdochium nivale, Monilinia fructicola, Monographella albescens, Monosporascus cannonballus, Naemacyclus* spp., *Ophiostoma novo-ulmi, Paracoccidioides brasiliensis, Penicillium expansum, Pestalotia rhododendri, Petrieffidium* spp., *Pezicula* spp., *Phialophora gregata, Phyllachora pomigena, Phymatotrichum omnivora, Physalospora abdita, Plectosporium tabacinum, Polyscytalum pustulans, Pseudopeziza medicaginis, Pyrenopeziza brassicae, Ramulispora sorghi, Rhabdocline pseudotsugae, Rhynchosporium secalis, Sacrocladium oryzae, Scedosporium* spp., *Schizothyrium pomi, Sclerotinia sclerotiorum, Sclerotinia minor, Sclerotium* spp., *Typhula ishikariensis, Seimatosporium mariae, Lepteutypa cupressi, Septocyta ruborum, Sphaceloma perseae, Sporonema phacidioides, Stigmina palmivora, Tapesia yallundae, Taphrina bullata, Thielviopsis basicola, Trichoseptoria fructigena, Zygophiala jamaicensis*; powdery mildew diseases for example those caused by Erysiphales such as *Blumeria graminis, Erysiphe polygoni, Uncinula necator, Sphaerotheca fuligena, Podosphaera leucotricha, Podospaera macularis Golovinomyces cichoracearum, Leveillula taurica, Microsphaera diffusa, Oidiopsis gossypii, Phyllactinia guttata* and *Oidium arachidis*; molds for example those caused by Botryosphaeriales such as *Dothiorella aromatica, Diplodia seriata, Guignardia bidwellii, Botrytis cinerea, Botryotinia allii, Botryotinia fabae, Fusicoccum amygdali, Lasiodiplodia theobromae, Macrophoma theicola, Macrophomina phaseolina, Phyllosticta cucurbitacearum*; anthracnoses for example those caused by Glommerelales such as *Colletotrichum gloeosporioides, Colletotrichum lagenarium, Colletotrichum gossypii, Glomerella cingulata*, and *Colletotrichum graminicola*; and wilts or blights for example those caused by Hypocreales such as *Acremonium strictum, Claviceps purpurea, Fusarium culmorum, Fusarium graminearum, Fusarium virguliforme, Fusarium oxysporum, Fusarium subglutinans, Fusarium oxysporum f. sp. cubense, Gerlachia nivale, Gibberella fujikuroi, Gibberella zeae, Gliocladium* spp., *Myrothecium verrucaria, Nectria ramulariae, Trichoderma viride, Trichothecium roseum*, and *Verticillium theobromae*.

Basidiomycetes, including smuts for example those caused by Ustilaginales such as *Ustilaginoidea virens, Ustilago nuda, Ustilago tritici, Ustilago zeae*, rusts for example those caused by Pucciniales such as *Cerotelium fici, Chrysomyxa arctostaphyli, Coleosporium ipomoeae, Hemileia vastatrix, Puccinia arachidis, Puccinia cacabata, Puccinia graminis, Puccinia recondita, Puccinia sorghi, Puccinia hordei, Puccinia striiformis f. sp. Hordei, Puccinia striiformis f. sp. Secalis, Pucciniastrum cotyli*, or Uredinales such as *Cronartium ribicola, Gymnosporangium juniperi-vigininae, Melampsora medusae, Phakopsora pachyrhizi, Phragmidium mucronatum, Physopella ampelosidis, Tranzschelia discolor* and *Uromyces viciae-fabae*; and other rots and diseases such as those caused by *Cryptococcus* spp., *Exobasidium vexans, Marasmiellus inoderma, Mycena* spp., *Sphacelotheca reiliana, Typhula ishikariensis, Urocystis agropyri, Itersonilia perplexans, Corticium invisum, Laetisaria fuciformis, Waitea circinata, Rhizoctonia solani, Thanetephorus cucurmeris, Entyloma dahliae, Entylomella microspora, Neovossia moliniae* and *Tilletia caries*.

Blastocladiomycetes, such as *Physoderma maydis*.

Mucoromycetes, such as *Choanephora cucurbitarum; Mucor* spp.; *Rhizopus arrhizus*, As well as diseases caused by other species and genera closely related to those listed above.

In addition to their fungicidal activity, the compounds and compositions comprising them may also have activity against bacteria such as *Erwinia amylovora, Erwinia caratovora, Xanthomonas campestris, Pseudomonas syringae, Strptomyces scabies* and other related species as well as certain protozoa.

Within the scope of present invention, target crops and/or useful plants to be protected typically comprise perennial and annual crops, such as berry plants for example blackberries, blueberries, cranberries, raspberries and strawberries; cereals for example barley, maize (corn), millet, oats, rice, rye, sorghum triticale and wheat; fibre plants for example cotton, flax, hemp, jute and sisal; field crops for example sugar and fodder beet, coffee, hops, mustard, oilseed rape (canola), poppy, sugar cane, sunflower, tea and tobacco; fruit trees for example apple, apricot, avocado, banana, cherry, citrus, nectarine, peach, pear and plum; grasses for example Bermuda grass, bluegrass, bentgrass, centipede grass, fescue, ryegrass, St. Augustine grass and Zoysia grass; herbs such as basil, borage, chives, coriander, lavender, lovage, mint, oregano, parsley, rosemary, sage and thyme; legumes for example beans, lentils, peas and soya beans; nuts for example almond, cashew, ground nut, hazelnut, peanut, pecan, pistachio and walnut; palms for example oil palm; ornamentals for example flowers, shrubs and trees; other trees, for example cacao, coconut, olive and rubber; vegetables for example asparagus, aubergine, broccoli, cabbage, carrot, cucumber, garlic, lettuce, marrow, melon, okra, onion, pepper, potato, pumpkin, rhubarb, spinach and tomato; and vines for example grapes.

The useful plants and/or target crops in accordance with the invention include conventional as well as genetically enhanced or engineered varieties such as, for example, insect resistant (e.g. Bt. and VIP varieties) as well as disease resistant, herbicide tolerant (e.g. glyphosate- and glufosinate-resistant maize varieties commercially available under the trade names RoundupReady® and LibertyLink®) and nematode tolerant varieties. By way of example, suitable genetically enhanced or engineered crop varieties include the Stoneville 5599BR cotton and Stoneville 4892BR cotton varieties.

The term "useful plants" and/or "target crops" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" and/or "target crops" is to be understood as including those which naturally are or have been rendered resistant to harmful insects. This includes plants transformed by the use of recombinant DNA techniques, for example, to be capable of synthesising one or more selectively acting toxins, such as are known, for example, from toxin-producing bacteria. Examples of toxins which can be expressed include δ-endotoxins, vegetative insecticidal proteins (Vip), insecticidal proteins of bacteria colonising nematodes, and toxins produced by scorpions, arachnids, wasps and fungi. An example of a crop that has been modified to express the Bacillus thuringiensis toxin is the Bt maize KnockOut® (Syngenta Seeds). An example of a crop comprising more than one gene that codes for insecticidal resistance and thus expresses more than one toxin is VipCot® (Syngenta Seeds). Crops or seed material thereof can also be resistant to multiple types of pests (so-called stacked transgenic events when created by genetic modification). For example, a plant can have the ability to express an insecticidal protein while at the same time being herbicide tolerant, for example Herculex I® (Dow AgroSciences, Pioneer Hi-Bred International).

The term "useful plants" and/or "target crops" is to be understood as including also useful plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

Toxins that can be expressed by transgenic plants include, for example, insecticidal proteins from Bacillus cereus or Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

Further, in the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO03/018810).

More examples of such toxins or transgenic plants capable of synthesising such toxins are disclosed, for example, in EP-A-0 374 753, WO93/07278, WO95/34656, EP-A-0 20 427 529, EP-A-451 878 and WO03/052073.

The processes for the preparation of such transgenic plants are generally known to the person skilled in the art and are described, for example, in the publications mentioned above. Cryl-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603×MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

The term "locus" as used herein means fields in or on which plants are growing, or where seeds of cultivated plants are sown, or where seed will be placed into the soil. It includes soil, seeds, and seedlings, as well as established vegetation.

The term "plants" refers to all physical parts of a plant, including seeds, seedlings, saplings, roots, tubers, stems, stalks, foliage, and fruits.

The term "plant propagation material" is understood to denote generative parts of the plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

Pesticidal agents referred to herein using their common name are known, for example, from "The Pesticide Manual", 15th Ed., British Crop Protection Council 2009.

The compounds of formula (I) may be used in unmodified form or, preferably, together with the adjuvants conventionally employed in the art of formulation. To this end they may be conveniently formulated in known manner to emulsifiable concentrates, coatable pastes, directly sprayable or dilutable solutions or suspensions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants, e.g. for agricultural use, can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

Suspension concentrates are aqueous formulations in which finely divided solid particles of the active compound are suspended. Such formulations include anti-settling agents and dispersing agents and may further include a wetting agent to enhance activity as well an anti-foam and a crystal growth inhibitor. In use, these concentrates are diluted in water and normally applied as a spray to the area to be treated. The amount of active ingredient may range from 0.5% to 95% of the concentrate.

Wettable powders are in the form of finely divided particles which disperse readily in water or other liquid carriers. The particles contain the active ingredient retained in a solid matrix. Typical solid matrices include fuller's earth, kaolin clays, silicas and other readily wet organic or inorganic solids. Wettable powders normally contain from 5% to 95% of the active ingredient plus a small amount of wetting, dispersing or emulsifying agent.

Emulsifiable concentrates are homogeneous liquid compositions dispersible in water or other liquid and may consist entirely of the active compound with a liquid or solid emulsifying agent, or may also contain a liquid carrier, such as xylene, heavy aromatic naphthas, isophorone and other non-volatile organic solvents. In use, these concentrates are dispersed in water or other liquid and normally applied as a spray to the area to be treated. The amount of active ingredient may range from 0.5% to 95% of the concentrate.

Granular formulations include both extrudates and relatively coarse particles and are usually applied without dilution to the area in which treatment is required. Typical carriers for granular formulations include sand, fuller's earth, attapulgite clay, bentonite clays, montmorillonite clay, vermiculite, perlite, calcium carbonate, brick, pumice, pyrophyllite, kaolin, dolomite, plaster, wood flour, ground corn cobs, ground peanut hulls, sugars, sodium chloride, sodium sulphate, sodium silicate, sodium borate, magnesia, mica, iron oxide, zinc oxide, titanium oxide, antimony oxide, cryolite, gypsum, diatomaceous earth, calcium sulphate and other organic or inorganic materials which absorb or which can be coated with the active compound. Granular formulations normally contain 5% to 25% of active ingredients which may include surface-active agents such as heavy aromatic naphthas, kerosene and other petroleum fractions, or vegetable oils; and/or stickers such as dextrins, glue or synthetic resins.

Dusts are free-flowing admixtures of the active ingredient with finely divided solids such as talc, clays, flours and other organic and inorganic solids which act as dispersants and carriers.

Microcapsules are typically droplets or granules of the active ingredient enclosed in an inert porous shell which allows escape of the enclosed material to the surroundings at controlled rates. Encapsulated droplets are typically 1 to 50 microns in diameter. The enclosed liquid typically constitutes 50 to 95% of the weight of the capsule and may include solvent in addition to the active compound. Encapsulated granules are generally porous granules with porous membranes sealing the granule pore openings, retaining the active species in liquid form inside the granule pores. Granules typically range from 1 millimetre to 1 centimetre and preferably 1 to 2 millimetres in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for agrochemical applications include simple solutions of the active ingredient in a solvent in which it is completely soluble at the desired concentration, such as acetone, alkylated naphthalenes, xylene and other organic solvents. Pressurised sprayers, wherein the active ingredient is dispersed in finely-divided form as a result of vaporisation of a low boiling dispersant solvent carrier, may also be used.

Suitable agricultural adjuvants and carriers that are useful in formulating the compositions of the invention in the formulation types described above are well known to those skilled in the art.

Liquid carriers that can be employed include, for example, water, toluene, xylene, petroleum naphtha, crop oil, acetone, methyl ethyl ketone, cyclohexanone, acetic anhydride, acetonitrile, acetophenone, amyl acetate, 2-butanone, chlorobenzene, cyclohexane, cyclohexanol, alkyl acetates, diacetonalcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethyl formamide, dimethyl sulfoxide, 1,4-dioxane, dipropylene glycol, dipropylene glycol methyl ether, dipropylene glycol dibenzoate, diproxitol, alkyl pyrrolidinone, ethyl acetate, 2-ethyl hexanol, ethylene carbonate, 1,1,1-trichloroethane, 2-heptanone, alpha pinene, d-limonene, ethylene glycol, ethylene glycol butyl ether, ethylene glycol methyl ether, gamma-butyrolactone, glycerol, glycerol diacetate, glycerol monoacetate, glycerol triacetate, hexadecane, hexylene glycol, isoamyl acetate, isobornyl acetate, isooctane, isophorone, isopropyl benzene, isopropyl myristate, lactic acid, laurylamine, mesityl oxide, methoxy-propanol, methyl isoamyl ketone, methyl isobutyl ketone, methyl laurate, methyl octanoate, methyl oleate, methylene chloride, m-xylene, n-hexane, n-octylamine, octadecanoic acid, octyl amine acetate, oleic acid, oleylamine, o-xylene, phenol, polyethylene glycol (PEG400), propionic acid, propylene glycol, propylene glycol monomethyl ether, p-xylene, toluene, triethyl phosphate, triethylene glycol, xylene sulfonic acid, paraffin, mineral oil, trichloroethylene, perchloroethylene, ethyl acetate, amyl acetate, butyl acetate, methanol, ethanol, isopropanol, and higher molecular weight alcohols such as amyl alcohol, tetrahydrofurfuryl alcohol, hexanol, octanol, etc., ethylene glycol, propylene glycol, glycerine and N-methyl-2-pyrrolidinone. Water is generally the carrier of choice for the dilution of concentrates.

Suitable solid carriers include, for example, talc, titanium dioxide, pyrophyllite clay, silica, attapulgite clay, kieselguhr, chalk, diatomaxeous earth, lime, calcium carbonate, bentonite clay, fuller's earth, cotton seed hulls, wheat flour, soybean flour, pumice, wood flour, walnut shell flour and lignin.

A broad range of surface-active agents are advantageously employed in both said liquid and solid compositions, especially those designed to be diluted with carrier before application. These agents, when used, normally comprise from 0.1% to 15% by weight of the formulation. They can be anionic, cationic, non-ionic or polymeric in character and can be employed as emulsifying agents, wetting agents, suspending agents or for other purposes. Typical surface active agents include salts of alkyl sulfates, such as diethanolammonium lauryl sulphate; alkylarylsulfonate salts, such as calcium dodecylbenzenesulfonate; alkylphenol-alkylene oxide addition products, such as nonylphenol-C.sub. 18 ethoxylate; alcohol-alkylene oxide addition products, such as tridecyl alcohol-C.sub. 16 ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly utilized in agricultural compositions include crystallisation inhibitors, viscosity modifiers, suspending agents, spray droplet modifiers, pigments, antioxidants, foaming agents, anti-foaming agents, light-blocking agents, compatibilizing agents, antifoam agents, sequestering agents, neutralising agents and buffers, corrosion inhibitors, dyes, odorants, spreading agents, penetration aids, micronutrients, emollients, lubricants and sticking agents.

The invention also provides for the use of provides a composition comprising a compound of formula (I) according to the present invention together with one or more pesticides, plant nutrients or plant fertilizers. The combination may also encompass specific plant traits incorporated into the plant using any means, for example conventional breeding or genetic modification.

Suitable examples of plant nutrients or plant fertilizers are calcium sulfate ($CaSO_4$), calcium nitrate ($Ca(NO_3)_2.4H_2O$), calcium carbonate ($CaCO_3$), potassium nitrate ($KNO_3$), magnesium sulfate ($MgSO_4$), potassium hydrogen phosphate ($KH_2PO_4$), manganese sulfate ($MnSO_4$), copper sulfate ($CuSO_4$), zinc sulfate ($ZnSO_4$), nickel chloride ($NiCl_2$), cobalt sulfate ($CoSO_4$), potassium hydroxide (KOH), sodium chloride (NaCl), boric acid ($H_3BO_3$) and metal salts thereof ($Na_2MoO_4$). The nutrients may be present in an amount of 5% to 50% by weight each. Preferred additional nutrients are urea (($NH_2)_2CO$), melamine ($C_3H_6N_6$), potassium oxide ($K_2O$), and inorganic nitrates. The most preferred additional plant nutrient is potassium oxide. Where the preferred additional nutrient is urea, it is present in an amount of generally 1% to 20% by weight, preferably 2% to 10% by weight or of 3% to 7% by weight.

Suitable examples of pesticides are acycloamino acid fungicides, aliphatic nitrogen fungicides, amide fungicides, anilide fungicides, antibiotic fungicides, aromatic fungicides, arsenical fungicides, aryl phenyl ketone fungicides, benzamide fungicides, benzanilide fungicides, benzimidazole fungicides, benzothiazole fungicides, botanical fungicides, bridged diphenyl fungicides, carbamate fungicides, carbanilate fungicides, conazole fungicides, copper fungicides, dicarboximide fungicides, dinitrophenol fungicides, dithiocarbamate fungicides, dithiolane fungicides, furamide fungicides, furanilide fungicides, hydrazide fungicides, imidazole fungicides, mercury fungicides, morpholine fungicides, organophosphorous fungicides, organotin fungicides, oxathiin fungicides, oxazole fungicides, phenylsulfamide fungicides, polysulfide fungicides, pyrazole fungicides, pyridine fungicides, pyrimidine fungicides, pyrrole fungicides, quaternary ammonium fungicides, quinoline fungicides, quinone fungicides, quinoxaline fungicides, strobilurin fungicides, sulfonanilide fungicides, thiadiazole fungicides, thiazole fungicides, thiazolidine fungicides, thiocarbamate fungicides, thiophene fungicides, triazine fungicides, triazole fungicides, triazolopyrimidine fungicides, urea fungicides, valinamide fungicides, zinc fungicides, Benzoylureas, carbamates, chloronicotinyls, diacylhydrazines, diamides, fiproles, macrolides, nitroimines, nitromethylenes, organochlorines, organophosphates, organosilicons, organotins, phenylpyrazoles, phosphoric esters, pyrethroids, spinosyns, tetramic acid derivatives, tetronic acid derivatives, Antibiotic nematicides, avermectin nematicides, botanical nematicides, carbamate nematicides, oxime carbamate nematicides, organophosphorus nematicides, nematophagous fungi or bacteria, amide herbicides, anilide herbicides, arsenical herbicides, arylalanine herbicides, aryloxyphenoxypropionic herbicides, benzofuranyl herbicides, benzoic acid herbicides, benzothiazole herbicides, benzoylcyclohexanedione herbicides, carbamate herbicides, carbanilate herbicides, chloroacetanilide herbicides, chlorotriazine herbicides, cyclohexene oxmie herbicides, cyclopropylisoxazole herbicides, dicarboximide herbicides, dinitroaniline herbicides, dinitrophenol herbicides, diphenyl ether herbicides, dithiocarbamate herbicides, fluoroalkyltriazine herbicides, halogenated aliphatic herbicides, imidazolinone herbicides, inorganic herbicides, methoxytriazine herbicides, methylthiotriazine herbicides, nitrile herbicides, nitrophenyl ether herbicides, organophosphorous herbicides, oxadiazolone herbicides, oxazole herbicides, phenoxy herbicides, phenoxyacetic herbicides, phenoxybutyric herbicides, phenoxypropionic herbicides, phenylenediamine herbicides, phenylurea herbicides, phthalic acid herbicides, picolinic acid herbicides, pyrazole herbicides, pyridazine herbicides, pyridazinone herbicides, pyridine herbicides, pyrimidinediamine herbicides, pyrimidinyloxybenzylamine herbicides, pyrimidinylsulfonylurea herbicides, quaternary ammonium herbicides, quinolinecarboxylic acid herbicides, sulfonamide herbicides, sulfonanilide herbicides, sulfonylurea herbicides, thiadiazolylurea herbicides, thioamide herbicides, thiocarbamate herbicides, thiocarbonate herbicides, thiourea herbicides, triazine herbicides, triazinone herbicides, triazinylsulfonylurea herbicides, triazole herbicides, triazolone herbicides, triazolopyrimidine herbicides, uracil herbicides, urea herbicides, microbials, plant extracts, pheromones, macrobials and other biologicals.

A further aspect of invention is related to a method of controlling or preventing an infestation of plants, e.g. useful plants such as crop plants, propagation material thereof, e.g. seeds, harvested crops, e.g. harvested food crops, or of non-living materials by insects or by phytopathogenic or spoilage microorganisms or organisms potentially harmful to man, especially fungal organisms, which comprises the application of a compound of formula (I) or of a preferred individual compound as above-defined as active ingredient to the plants, to parts of the plants or to the locus thereof, to the propagation material thereof, or to any part of the non-living materials.

Controlling or preventing means reducing infestation by insects or by phytopathogenic or spoilage microorganisms or organisms potentially harmful to man, especially fungal organisms, to such a level that an improvement is demonstrated.

A preferred method of controlling or preventing an infestation of crop plants by phytopathogenic microorganisms, especially fungal organisms, or insects which comprises the application of a compound of formula (I), or an agrochemical composition which contains at least one of said compounds, is foliar application. The frequency of application and the rate of application will depend on the risk of infestation by the corresponding pathogen or insect. However, the compounds of formula (I) can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula (I) may also be applied to seeds (coating) by impregnating the seeds or tubers either with a liquid formulation of the fungicide or coating them with a solid formulation.

A formulation, e.g. a composition containing the compound of formula (I), and, if desired, a solid or liquid adjuvant or monomers for encapsulating the compound of formula (I), may be prepared in a known manner, typically by intimately mixing and/or grinding the compound with extenders, for example solvents, solid carriers and, optionally, surface active compounds (surfactants).

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is preferably 1 g to 2000 g of active ingredient per hectare, more preferably 10 to 1000 g/ha, most preferably 10 to 600 g/ha. When used as seed drenching agent, convenient dosages are from 10 mg to 1 g of active substance per kg of seeds.

When the compositions are used for treating seed, rates of 0.001 to 50 g of a compound of formula (I) per kg of seed, preferably from 0.01 to 10 g per kg of seed are generally sufficient.

Suitably, a composition comprising a compound of formula (I) according to the present invention is applied either preventative, meaning prior to disease development or curative, meaning after disease development.

The compositions of the invention may be employed in any conventional form, for example in the form of a twin pack, a powder for dry seed treatment (DS), an emulsion for seed treatment (ES), a flowable concentrate for seed treatment (FS), a solution for seed treatment (LS), a water dispersible powder for seed treatment (WS), a capsule suspension for seed treatment (CF), a gel for seed treatment (GF), an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP) or any technically feasible formulation in combination with agriculturally acceptable adjuvants.

Such compositions may be produced in conventional manner, e.g. by mixing the active ingredients with appropriate formulation inerts (diluents, solvents, fillers and optionally other formulating ingredients such as surfactants, biocides, anti-freeze, stickers, thickeners and compounds that provide adjuvancy effects). Also conventional slow release formulations may be employed where long lasting efficacy is intended. Particularly formulations to be applied in spraying forms, such as water dispersible concentrates (e.g. EC, SC, DC, OD, SE, EW, EO and the like), wettable powders and granules, may contain surfactants such as wetting and dispersing agents and other compounds that provide adjuvancy effects, e.g. the ondensation product of formaldehyde with naphthalene sulphonate, an alkylarylsulphonate, a lignin sulphonate, a fatty alkyl sulphate, and ethoxylated alkylphenol and an ethoxylated fatty alcohol.

A seed dressing formulation is applied in a manner known per se to the seeds employing the combination of the invention and a diluent in suitable seed dressing formulation form, e.g. as an aqueous suspension or in a dry powder form having good adherence to the seeds. Such seed dressing formulations are known in the art. Seed dressing formulations may contain the single active ingredients or the combination of active ingredients in encapsulated form, e.g. as slow release capsules or microcapsules.

In general, the formulations include from 0.01 to 90% by weight of active agent, from 0 to 20% agriculturally acceptable surfactant and 10 to 99.99% solid or liquid formulation inerts and adjuvant(s), the active agent consisting of at least the compound of formula (I) together with component (B) and (C), and optionally other active agents, particularly microbiocides or conservatives or the like. Concentrated forms of compositions generally contain in between about 2 and 80%, preferably between about 5 and 70% by weight of active agent. Application forms of formulation may for example contain from 0.01 to 20% by weight, preferably from 0.01 to 5% by weight of active agent. Whereas commercial products will preferably be formulated as concentrates, the end user will normally employ diluted formulations.

Whereas it is preferred to formulate commercial products as concentrates, the end user will normally use dilute formulations.

EXAMPLES

The Examples which follow serve to illustrate the invention. Certain compounds of the invention can be distinguished from known compounds by virtue of greater efficacy at low application rates, which can be verified by the person skilled in the art using the experimental procedures outlined in the Examples, using lower application rates if necessary, for example 50 ppm, 12.5 ppm, 6 ppm, 3 ppm, 1.5 ppm, 0.8 ppm or 0.2 ppm.

Throughout this description, temperatures are given in degrees Celsius and "m.p." means melting point. LC/MS means Liquid Chromatography Mass Spectroscopy and the description of the apparatus and the methods are:

FORMULATION EXAMPLES

| Wettable powders | a) | b) | c) |
|---|---|---|---|
| active ingredient [compound of formula (I)] | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The active ingredient is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredient [compound of formula (I)] | 25% | 50% | 75% |
| light mineral oil | 5% | 5% | 5% |
| highly dispersed silicic acid | 5% | 5% | — |
| Kaolin | 65% | 40% | — |
| Talcum | — | — | 20 |

The active ingredient is thoroughly mixed with the adjuvants and the mixture is thoroughly ground in a suitable mill, affording powders that can be used directly for seed treatment.

| Emulsifiable concentrate | |
|---|---|
| active ingredient [compound of formula (I)] | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredient [compound of formula (I)] | 5% | 6% | 4% |
| talcum | 95% | — | — |
| Kaolin | — | 94% | — |
| mineral filler | — | — | 96% |

Ready-for-use dusts are obtained by mixing the active ingredient with the carrier and grinding the mixture in a suitable mill. Such powders can also be used for dry dressings for seed.

| Extruder granules | |
|---|---|
| Active ingredient [compound of formula (I)] | 15% |
| sodium lignosulfonate | 2% |
| carboxymethylcellulose | 1% |
| Kaolin | 82% |

The active ingredient is mixed and ground with the adjuvants, and the mixture is moistened with water. The mixture is extruded and then dried in a stream of air.

| Coated granules | |
|---|---|
| Active ingredient [compound of formula (I)] | 8% |
| polyethylene glycol (mol. wt. 200) | 3% |
| Kaolin | 89% |

The finely ground active ingredient is uniformly applied, in a mixer, to the kaolin moistened with polyethylene glycol. Non-dusty coated granules are obtained in this manner.

| Suspension concentrate | |
|---|---|
| active ingredient [compound of formula (I)] | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

| Flowable concentrate for seed treatment | |
|---|---|
| active ingredient [compound of formula (I)] | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of a combination of the compound of formula (I) are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed.

The obtained capsule suspension is stabilized by adding 0.25 parts of a thickener and 3 parts of a dispersing agent. The capsule suspension formulation contains 28% of the active ingredients. The medium capsule diameter is 8-15 microns.

The resulting formulation is applied to seeds as an aqueous suspension in an apparatus suitable for that purpose.

PREPARATION EXAMPLES

Using techniques described above and below, and also in WO 08/101682 (pp. 22-33) and WO 12/146125 (pp. 370-378), together with further techniques generally known to the person skilled in the art, compounds of formula (I) may be prepared.

Example 1

This example illustrate the preparation N-ethyl-N'-[4-(1-hydroxy-1-phenyl-ethyl)-5-methoxy-2-methyl-phenyl]-N-methyl-formamidine

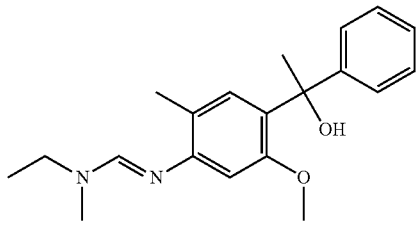 [SMILES: CCN(C)/C=N/c1cc(OC)c(C(C)(O)c2ccccc2)cc1C]

a) Preparation of 4-bromo-5-methoxy-2-methyl-aniline

N-bromosuccinimide (1.28 g, 7.29 mmol) was added portion wise to an ice-cold (0-5° C.) solution of 5-methoxy-2-methyl-aniline (1.0 g, 7.29 mmol) in $CHCl_3$ (15 mL). The resulting solution was stirred for 60 minutes at 0° C., warmed to room temperature and diluted with $CH_2Cl_2$. The mixture was washed with aqueous $NaHCO_3$ (+2 mL $Na_2S_2O_3$ solution), brine and dried over $MgSO_4$. Solids were removed by filtration and volatiles were removed in vacuo. The residue was purified by flash chromatography on silica gel to afford the title compound as off white solid.

$^1$H NMR (400 MHz, $CDCl_3$): δ 7.17 (s, 1H), 6.27 (s, 1H), 3.82 (s, 3H), 3.53-3.73 (br. s., 2H), 2.08 (s, 3H).

b) Preparation of N'-(4-bromo-5-methoxy-2-methyl-phenyl)-N-ethyl-N-methyl-formamidine To a suspension of 4-bromo-5-methoxy-2-methyl-aniline (1.4 g, 6.48 mmol) and p-toluene sulfonic acid (0.05 g, 0.32 mmol) in toluene (13 mL) was added N-(dimethoxymethyl)-N-methyl-ethanamine (1.3 g, 9.7 mmol) at room temperature. The resulting clear solution was warmed to 50° C. and stirred for 24 h at this temperature. After cooling to room temperature, the reaction mixture was diluted with ethyl acetate, washed with aqueous $NaHCO_3$, brine and dried over $MgSO_4$. Solids were removed by filtration and volatiles were removed in vacuo. The residue was purified by flash chromatography on silica gel to afford the title compound as light yellow liquid.

$^1$H NMR (400 MHz, $CDCl_3$): δ 7.40 (br. s., 1H), 7.26 (s, 1H), 6.33 (s, 1H), 3.85 (s, 3H), 3.34 (br. s., 2H), 3.00 (s, 3H), 2.16 (s, 3H), 1.22 (t, 3H).

c) Preparation of N-ethyl-N'-[4-(1-hydroxy-1-phenyl-ethyl)-5-methoxy-2-methyl-phenyl]-N-methyl-formamidine A solution of N'-(4-bromo-5-methoxy-2-methyl-phenyl)-N-ethyl-N-methyl-formamidine (0.10 g, 0.35 mmol) in dry tetrahydrofuran (3.5 mL) under $N_2$-atmosphere was cooled to −78° C. and tert-butyl lithium (1.5 M in pentanes, 0.49 mL, 0.74 mmol) was added slowly. The reaction was aged for 5 min at −78° C. and then 1-phenylethanone (0.044 g, 0.37 mmol) was added drop wise. The cooling bath was removed, the reaction was allowed to warm to room temperature and stirred for an additional 10 min. Aqueous $NaHCO_3$ was added and the mixture was extracted with EtOAc. The organic layer was washed with brine, dried over $MgSO_4$, filtrated and concentrated in vacuo. The residue was purified by flash chromatography on silica gel to afford the title compound as white solid.

$^1$H NMR (400 MHz, $CDCl_3$): δ 7.41 (br. s., 1H), 7.28-7.34 (m, 2H), 7.12-7.25 (m, 4H), 6.32 (s, 1H), 4.64 (s, 1H), 3.51 (s, 3H), 3.20-3.47 (br. s, 2H), 3.00 (s, 3H), 2.24 (s, 3H), 1.80 (s, 3H), 1.21 (t, 3H).

Example 2

This example illustrate the preparation of N-ethyl-N'-[4-[1-hydroxy-2-methyl-1-(trifluoromethyl)propyl]-5-methoxy-2-methyl-phenyl]-N-methyl-formamidine

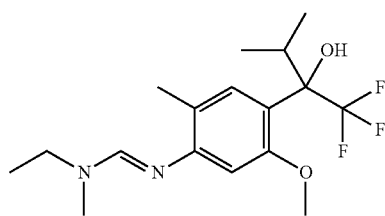 [SMILES: CCN(C)/C=N/c1cc(OC)c(C(O)(C(C)C)C(F)(F)F)cc1C]

a) Preparation of N-ethyl-N'-[5-methoxy-2-methyl-4-(2-methylpropanoyl)phenyl]-N-methyl-formamidine A solution of N'-(4-bromo-5-methoxy-2-methyl-phenyl)-N-ethyl-N-methyl-formamidine (2.0 g, 7.01 mmol) in dry tetrahydrofuran (3.5 mL) under $N_2$-atmosphere was added drop wise to a suspension of LiCl (0.33 g, 7.71 mmol) and Mg-turnings (0.26 g, 7.02 mmol) in dry tetrahydrofuran (3.5 mL) at a temperature between 20° C. to 40° C. (temperature controlled by addition rate). Upon completed addition, the reaction was aged for 1 h at 40° C. and then the mixture was then cooled to 0° C. N-methoxy-N,2-dimethyl-propanamide (1.01 g, 7.33 mmol) was added drop wise and the reaction was mixture was gradually warmed to RT over 1 h. Aqueous $NH_4Cl$ solution was added and the mixture was extracted with EtOAc. The organic layer was washed with water, brine, dried over $MgSO_4$, filtrated and concentrated in vacuo. The residue was purified by flash chromatography on silica gel to afford the title compound as light yellow oil.

$^1$H NMR (400 MHz, $CDCl_3$) δ 7.47 (br. s, 2H), 6.30 (s, 1H), 3.85 (s, 3H), 3.25-3.60 (m, 3H), 3.02 (s, 3H), 2.18 (s, 3H), 1.59 (s, 1H), 1.23 (t, 3H), 1.13 (d, 6H).

b) Preparation of N-ethyl-N'-[4-[1-hydroxy-2-methyl-1-(trifluoromethyl)propyl]-5-methoxy-2-methyl-phenyl]-N-methyl-formamidine Trimethyl(trifluoromethyl)silane (0.26 g, 1.81 mmol) was added drop wise to a solution of N-ethyl-N'-[5-methoxy-2-methyl-4-(2-methylpropanoyl)phenyl]-N-methyl-formamidine (0.50 g, 1.81 mmol) and CsF (0.03 g, 0.18 mmol) in toluene (9 mL) at 40° C. The resulting mixture was aged for 3 h at 40° C., a second portion of trimethyl(trifluoromethyl)silane (0.13 g, 0.91 mmol) was then added and the reaction was stirred for additional 30 min before being concentrated in vacuo to a brown oil.

This residue was taken up in methanol (7 mL), treated with potassium carbonate (0.37 g, 2.71 mmol) and aq. sodium hydroxide (2 M, 3 drops), warmed to 40° C. and stirred for 24 h at this temperature. Aqueous $NaHCO_3$ solution was then added and the emulsion was extracted with EtOAc. The organic layer was washed with water, brine, dried over $MgSO_4$, filtrated and concentrated in vacuo. The residue was purified by flash chromatography on silica gel to afford the title compound as light brown solid (m.p. 57-59° C.).

$^1$H NMR (400 MHz, $CDCl_3$) δ 7.47 (br s, 1H), 7.07 (s, 1H), 6.56 (br s, 1H), 6.40 (s, 1H), 3.90 (s, 3H), 3.22-3.66 (m, 2H), 3.03 (s, 3H), 2.46-2.66 (m, 1H), 2.22 (s, 3H), 1.25 (t, 3H), 1.16 (d, 3H), 0.87 (d, 3H).

TABLE E

Physical data of compounds of formula (I)
The compounds of formula (I) in Table E were prepared using techniques analogous to those described above and/or common synthetic techniques generally known to the person skilled in the art, as well as those described in WO 12/146125 (pp.370-378) and WO 08/101682 (pp.22-33).

| Entry | STRUCTURE | RT (min) | [M + H] (measured) | Method | MP ° C. |
|---|---|---|---|---|---|
| E1.001 | 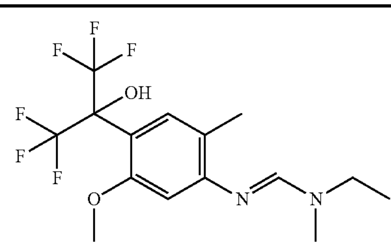 | 0.79 | 373 | A | 126-128 |

TABLE E-continued

Physical data of compounds of formula (I)
The compounds of formula (I) in Table E were prepared using techniques analogous
to those described above and/or common synthetic techniques generally known to the
person skilled in the art, as well as those described in WO 12/146125 (pp.370-378) and WO
08/101682 (pp.22-33).

| Entry | STRUCTURE | RT (min) | [M + H] (measured) | Method | MP ° C. |
|---|---|---|---|---|---|
| E1.002 | 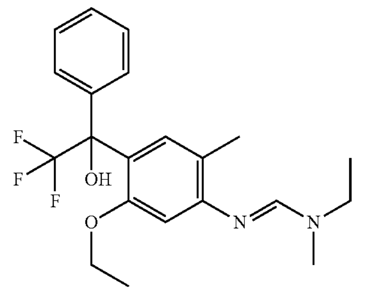 [SMILES: CCOc1cc(/N=C/N(C)CC)c(C)cc1C(O)(c1ccccc1)C(F)(F)F] | 0.80 | 395 | A | 148-151 |
| E1.003 | 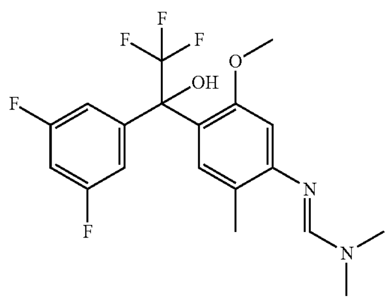 [SMILES: COc1cc(/N=C/N(C)C)c(C)cc1C(O)(c1cc(F)cc(F)c1)C(F)(F)F] | 0.83 | 417 | A | 107-108 |
| E1.004 | 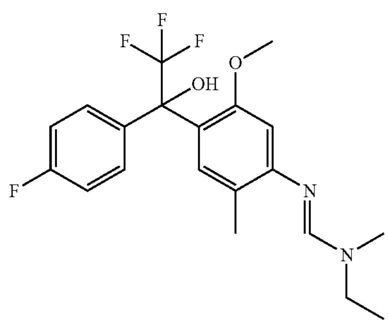 [SMILES: CCN(C)/C=N/c1cc(OC)c(C(O)(c2ccc(F)cc2)C(F)(F)F)cc1C] | 0.81 | 399 | A | 102-104 |
| E1.005 | 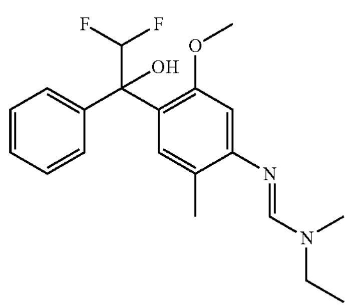 [SMILES: CCN(C)/C=N/c1cc(OC)c(C(O)(c2ccccc2)C(F)F)cc1C] | 0.71 | 363 | A | |
| E1.006 | 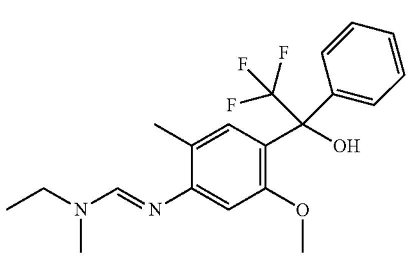 [SMILES: CCN(C)/C=N/c1cc(OC)c(C(O)(c2ccccc2)C(F)(F)F)cc1C] | 0.79 | 381 | A | 160-162 |

TABLE E-continued

*Physical data of compounds of formula (I)*
The compounds of formula (I) in Table E were prepared using techniques analogous
to those described above and/or common synthetic techniques generally known to the
person skilled in the art, as well as those described in WO 12/146125 (pp.370-378) and WO
08/101682 (pp.22-33).

| Entry | STRUCTURE | RT (min) | [M + H] (measured) | Method | MP ° C. |
|---|---|---|---|---|---|
| E1.007 | 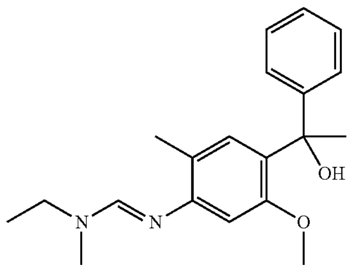 [SMILES: CCN(C)/C=N/c1cc(OC)c(C(C)(O)c2ccccc2)cc1C] | 0.74 | 327 | A | |
| E1.008 | 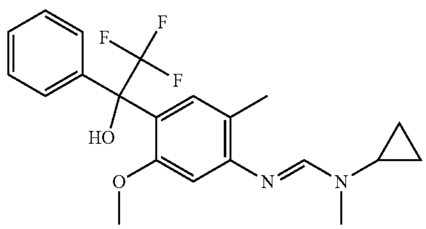 [SMILES: COc1cc(/N=C/N(C)C2CC2)c(C)cc1C(O)(c1ccccc1)C(F)(F)F] | 0.80 | 393 | A | |
| E1.009 | 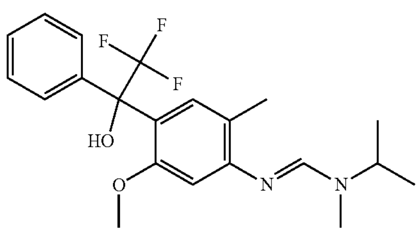 [SMILES: COc1cc(/N=C/N(C)C(C)C)c(C)cc1C(O)(c1ccccc1)C(F)(F)F] | 0.81 | 395 | A | 110-111 |
| E1.010 | 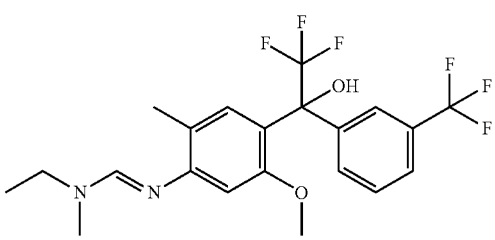 [SMILES: CCN(C)/C=N/c1cc(OC)c(C(O)(c2cccc(C(F)(F)F)c2)C(F)(F)F)cc1C] | | | | 121-123 |
| E1.011 | 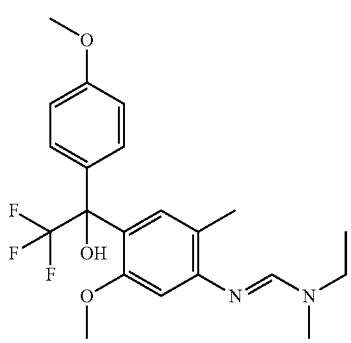 [SMILES: CCN(C)/C=N/c1cc(OC)c(C(O)(c2ccc(OC)cc2)C(F)(F)F)cc1C] | 0.90 | 411 | A | 67-71 |

TABLE E-continued

*Physical data of compounds of formula (I)*
*The compounds of formula (I) in Table E were prepared using techniques analogous to those described above and/or common synthetic techniques generally known to the person skilled in the art, as well as those described in WO 12/146125 (pp.370-378) and WO 08/101682 (pp.22-33).*

| Entry | STRUCTURE | RT (min) | [M + H] (measured) | Method | MP ° C. |
|---|---|---|---|---|---|
| E1.012 | 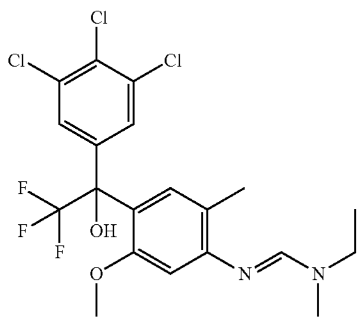 [SMILES: CCN(C)/C=N/c1cc(OC)c(C(O)(c2cc(Cl)c(Cl)c(Cl)c2)C(F)(F)F)cc1C] | 1.26 | 483 | A | |
| E1.013 | 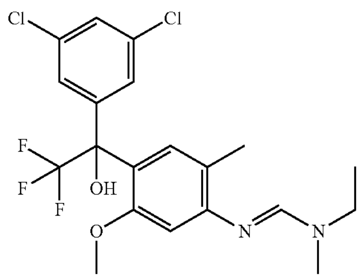 [SMILES: CCN(C)/C=N/c1cc(OC)c(C(O)(c2cc(Cl)cc(Cl)c2)C(F)(F)F)cc1C] | 1.24 | 449 | A | |
| E1.014 | 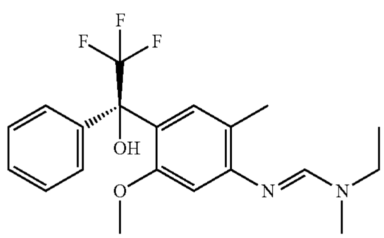 [SMILES: CCN(C)/C=N/c1cc(OC)c([C@](O)(c2ccccc2)C(F)(F)F)cc1C] | 0.79 | 381 | A | |
| E1.015 | 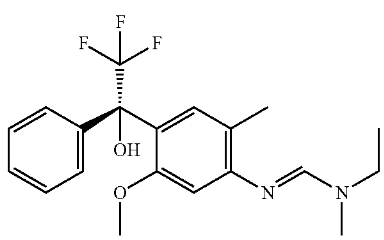 [SMILES: CCN(C)/C=N/c1cc(OC)c([C@@](O)(c2ccccc2)C(F)(F)F)cc1C] | 0.79 | 381 | A | |
| E1.016 | 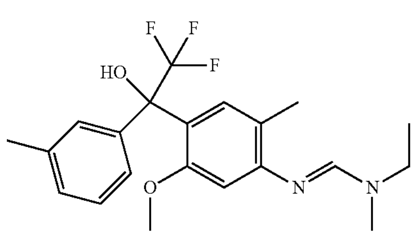 [SMILES: CCN(C)/C=N/c1cc(OC)c(C(O)(c2cccc(C)c2)C(F)(F)F)cc1C] | 0.89 | 395 | A | 125-127 |

TABLE E-continued

Physical data of compounds of formula (I)
The compounds of formula (I) in Table E were prepared using techniques analogous
to those described above and/or common synthetic techniques generally known to the
person skilled in the art, as well as those described in WO 12/146125 (pp.370-378) and WO
08/101682 (pp.22-33).

| Entry | STRUCTURE | RT (min) | [M + H] (measured) | Method | MP ° C. |
|---|---|---|---|---|---|
| E1.017 | 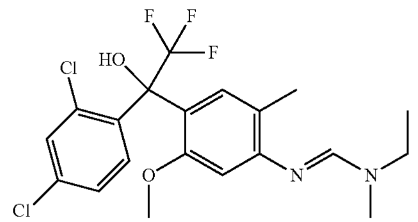 [SMILES: CCN(C)/C=N/c1cc(OC)c(C(O)(c2ccc(Cl)cc2Cl)C(F)(F)F)cc1C] | 0.92 | 449 | A | 119-121 |
| E1.018 | 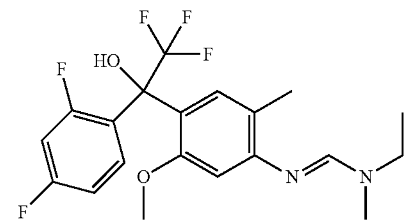 [SMILES: CCN(C)/C=N/c1cc(OC)c(C(O)(c2ccc(F)cc2F)C(F)(F)F)cc1C] | | | | 113-114 |
| E1.019 | 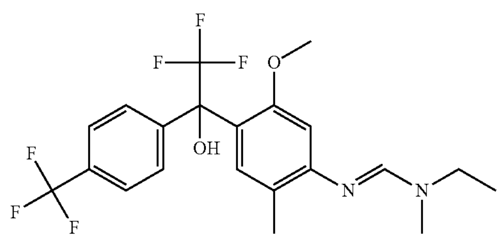 [SMILES: CCN(C)/C=N/c1cc(OC)c(C(O)(c2ccc(C(F)(F)F)cc2)C(F)(F)F)cc1C] | 0.94 | 449 | A | 124-126 |
| E1.020 | 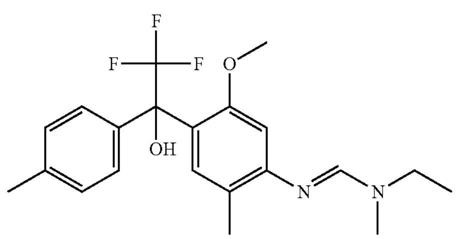 [SMILES: CCN(C)/C=N/c1cc(OC)c(C(O)(c2ccc(C)cc2)C(F)(F)F)cc1C] | 0.90 | 395 | A | 112-114 |
| E1.021 | 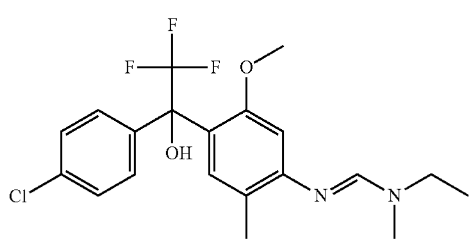 [SMILES: CCN(C)/C=N/c1cc(OC)c(C(O)(c2ccc(Cl)cc2)C(F)(F)F)cc1C] | 0.90 | 415 | A | 134-135 |
| E1.022 | 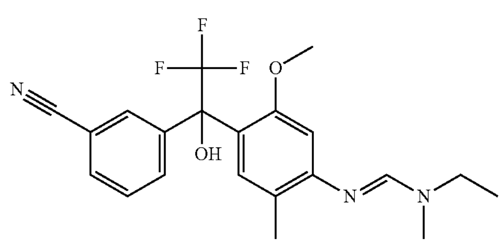 [SMILES: CCN(C)/C=N/c1cc(OC)c(C(O)(c2cccc(C#N)c2)C(F)(F)F)cc1C] | 0.79 | 406 | A | 38-40 |

TABLE E-continued

*Physical data of compounds of formula (I)*

*The compounds of formula (I) in Table E were prepared using techniques analogous to those described above and/or common synthetic techniques generally known to the person skilled in the art, as well as those described in WO 12/146125 (pp.370-378) and WO 08/101682 (pp.22-33).*

| Entry | STRUCTURE | RT (min) | [M + H] (measured) | Method | MP ° C. |
|---|---|---|---|---|---|
| E1.023 | 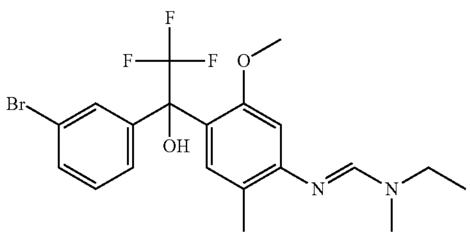 [SMILES: CCN(C)/C=N/c1cc(OC)c(C(O)(c2cccc(Br)c2)C(F)(F)F)cc1C] | 0.91 | 459 | A | 98-100 |
| E1.024 | 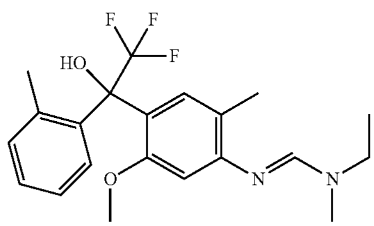 [SMILES: CCN(C)/C=N/c1cc(OC)c(C(O)(c2ccccc2C)C(F)(F)F)cc1C] | 0.79 | 395 | A | 115-117 |
| E1.025 | 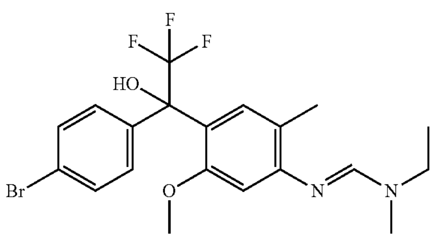 [SMILES: CCN(C)/C=N/c1cc(OC)c(C(O)(c2ccc(Br)cc2)C(F)(F)F)cc1C] | 0.91 | 459 | A | 127-129 |
| E1.026 | 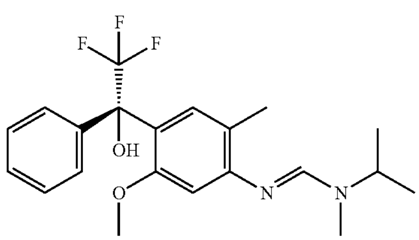 [SMILES: COc1cc(/N=C/N(C)C(C)C)c(C)cc1[C@@](O)(c1ccccc1)C(F)(F)F] | 0.79 | 395 | A | 110.5-111.7 |
| E1.027 | 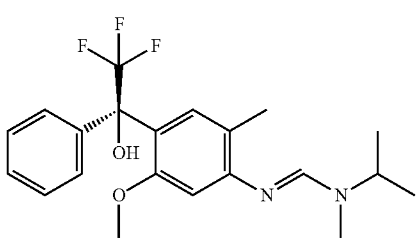 [SMILES: COc1cc(/N=C/N(C)C(C)C)c(C)cc1[C@](O)(c1ccccc1)C(F)(F)F] | 0.79 | 395 | A | 110.5-111.7 |

TABLE E-continued

*Physical data of compounds of formula (I)*
The compounds of formula (I) in Table E were prepared using techniques analogous to those described above and/or common synthetic techniques generally known to the person skilled in the art, as well as those described in WO 12/146125 (pp.370-378) and WO 08/101682 (pp.22-33).

| Entry | STRUCTURE | RT (min) | [M + H] (measured) | Method | MP ° C. |
|---|---|---|---|---|---|
| E1.028 | 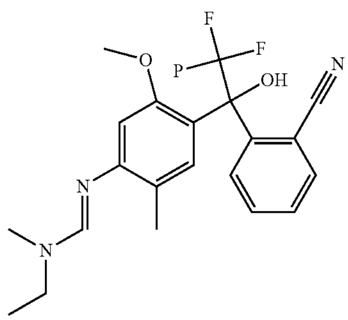 | 0.69 | 406 | A | 55-58° C. |
| E1.029 | 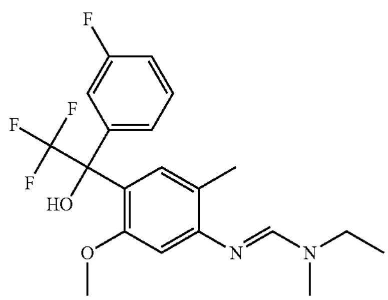 [SMILES: CCN(C)/C=N/c1cc(OC)c(C(O)(c2cccc(F)c2)C(F)(F)F)cc1C] | 0.81 | 399 | A | 130-132 |
| E1.030 | 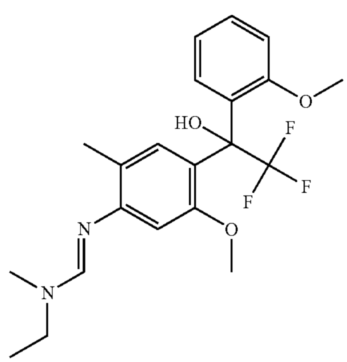 | 0.77 | 411 | A | |
| E1.031 | 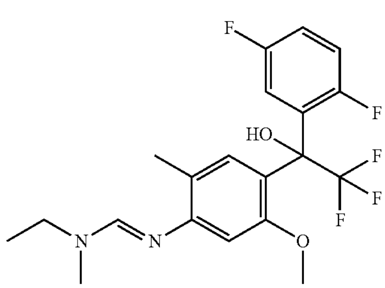 [SMILES: CCN(C)/C=N/c1cc(OC)c(C(O)(c2cc(F)ccc2F)C(F)(F)F)cc1C] | | | | 137-140 |

TABLE E-continued
Physical data of compounds of formula (I)
The compounds of formula (I) in Table E were prepared using techniques analogous
to those described above and/or common synthetic techniques generally known to the
person skilled in the art, as well as those described in WO 12/146125 (pp.370-378) and WO
08/101682 (pp.22-33).
| Entry | STRUCTURE | RT (min) | [M + H] (measured) | Method | MP ° C. |
|---|---|---|---|---|---|
| E1.032 | 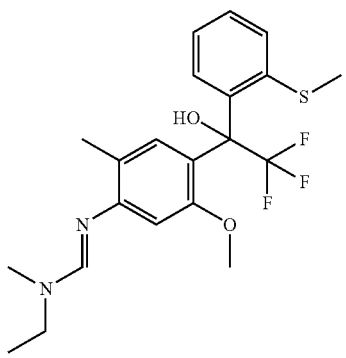 | 0.77 | 427 | A | 104-106 |
| E1.033 | 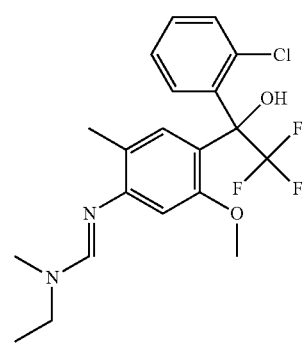 | 0.79 | 415 | A | 97-100 |
| E1.034 | 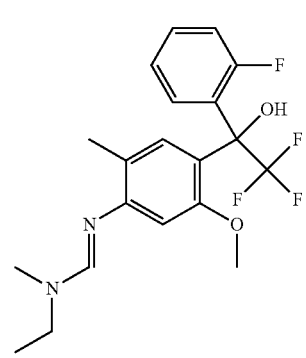 [SMILES: CCN(C)/C=N/c1cc(OC)c(C(O)(c2ccccc2F)C(F)(F)F)cc1C] | 0.78 | 399 | A | 96-98 |
| E1.035 | 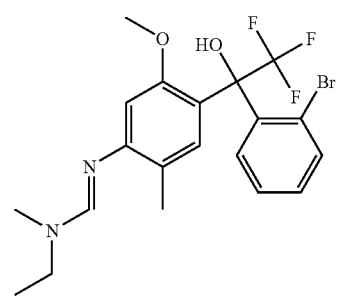 [SMILES: CCN(C)/C=N/c1cc(OC)c(C(O)(c2ccccc2Br)C(F)(F)F)cc1C] | 0.79 | 459 | A | 114-116 |

TABLE E-continued

*Physical data of compounds of formula (I)*
The compounds of formula (I) in Table E were prepared using techniques analogous to those described above and/or common synthetic techniques generally known to the person skilled in the art, as well as those described in WO 12/146125 (pp.370-378) and WO 08/101682 (pp.22-33).

| Entry | STRUCTURE | RT (min) | [M + H] (measured) | Method | MP ° C. |
|---|---|---|---|---|---|
| E1.036 | 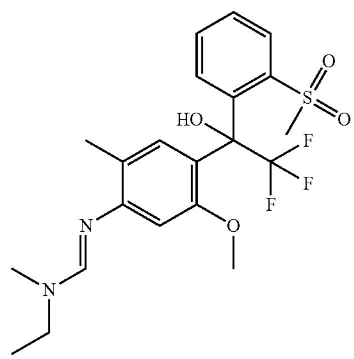 [SMILES: CCN(C)/C=N/c1cc(OC)c(C(O)(c2ccccc2S(C)(=O)=O)C(F)(F)F)cc1C] | 0.74 | 459 | A | 177-180 |
| E1.037 | 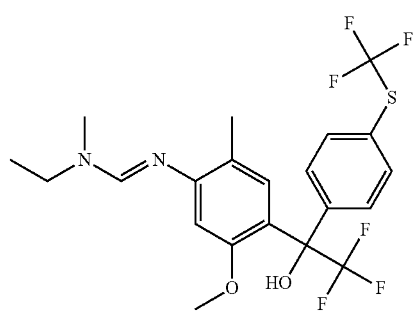 [SMILES: CCN(C)/C=N/c1cc(OC)c(C(O)(c2ccc(SC(F)(F)F)cc2)C(F)(F)F)cc1C] | 0.90 | 481 | A | 64-66 |
| E1.038 | 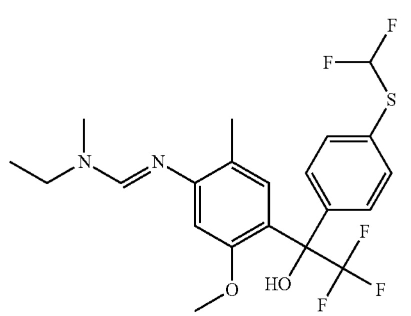 [SMILES: CCN(C)/C=N/c1cc(OC)c(C(O)(c2ccc(SC(F)F)cc2)C(F)(F)F)cc1C] | 0.84 | 463 | A | |
| E1.039 | 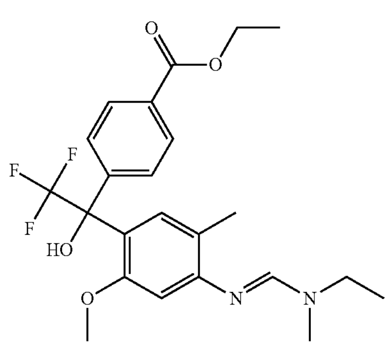 [SMILES: CCOC(=O)c1ccc(C(O)(c2cc(C)c(/N=C/N(C)CC)cc2OC)C(F)(F)F)cc1] | 0.82 | 453 | A | 118-120 |

TABLE E-continued

*Physical data of compounds of formula (I)*

The compounds of formula (I) in Table E were prepared using techniques analogous to those described above and/or common synthetic techniques generally known to the person skilled in the art, as well as those described in WO 12/146125 (pp.370-378) and WO 08/101682 (pp.22-33).

| Entry | STRUCTURE | RT (min) | [M + H] (measured) | Method | MP ° C. |
|---|---|---|---|---|---|
| E1.040 | 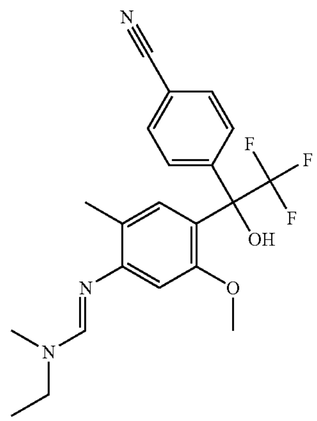 [SMILES: CCN(C)/C=N/c1cc(OC)c(C(O)(c2ccc(C#N)cc2)C(F)(F)F)cc1C] | 0.75 | 406 | A | 167-169 |
| E1.041 | 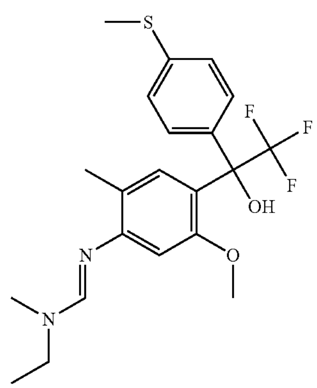 [SMILES: CCN(C)/C=N/c1cc(OC)c(C(O)(c2ccc(SC)cc2)C(F)(F)F)cc1C] | 0.81 | 427 | A | 89-91 |
| E1.042 | 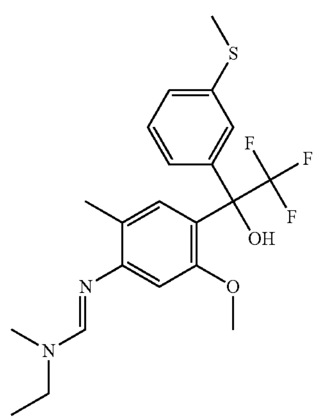 [SMILES: CCN(C)/C=N/c1cc(OC)c(C(O)(c2cccc(SC)c2)C(F)(F)F)cc1C] | 0.81 | 427 | A | |

TABLE E-continued

*Physical data of compounds of formula (I)*
*The compounds of formula (I) in Table E were prepared using techniques analogous to those described above and/or common synthetic techniques generally known to the person skilled in the art, as well as those described in WO 12/146125 (pp.370-378) and WO 08/101682 (pp.22-33).*

| Entry | STRUCTURE | RT (min) | [M + H] (measured) | Method | MP ° C. |
|---|---|---|---|---|---|
| E1.043 | 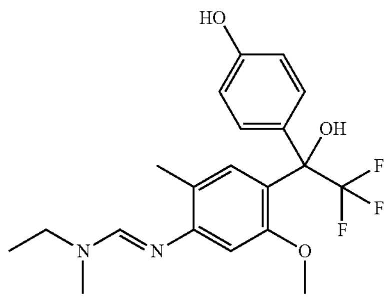 [SMILES: CCN(C)/C=N/c1cc(OC)c(C(O)(c2ccc(O)cc2)C(F)(F)F)cc1C] | 0.67 | 397 | A | 240-242 |
| E1.044 | 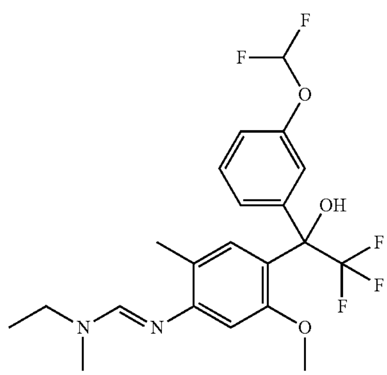 [SMILES: CCN(C)/C=N/c1cc(OC)c(C(O)(c2cccc(OC(F)F)c2)C(F)(F)F)cc1C] | 0.81 | 447 | A | 119-121 |
| E1.045 | 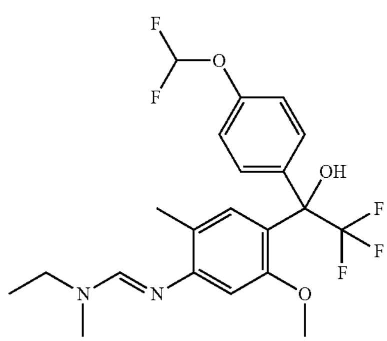 [SMILES: CCN(C)/C=N/c1cc(OC)c(C(O)(c2ccc(OC(F)F)cc2)C(F)(F)F)cc1C] | 0.80 | 447 | A | 85-87 |
| E1.046 | 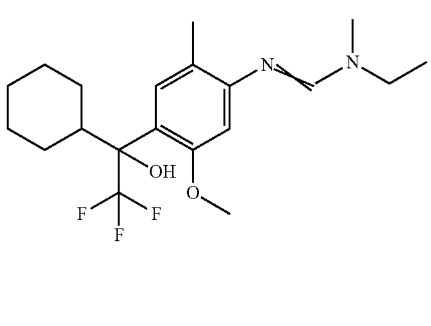 | 1.24 | 387 | A | |

TABLE E-continued

Physical data of compounds of formula (I)
The compounds of formula (I) in Table E were prepared using techniques analogous
to those described above and/or common synthetic techniques generally known to the
person skilled in the art, as well as those described in WO 12/146125 (pp.370-378) and WO
08/101682 (pp.22-33).

| Entry | STRUCTURE | RT (min) | [M + H] (measured) | Method | MP ° C. |
|---|---|---|---|---|---|
| E1.047 | 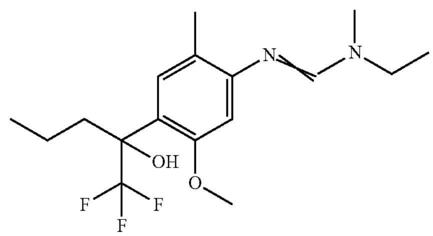 | 1.15 | 347 | A | |
| E1.048 | 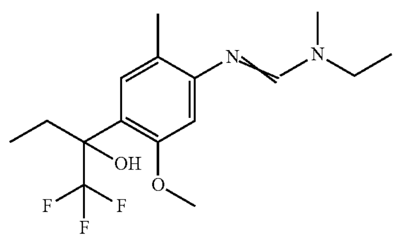 | 0.67 | 333 | A | 69-73 |
| E1.049 | 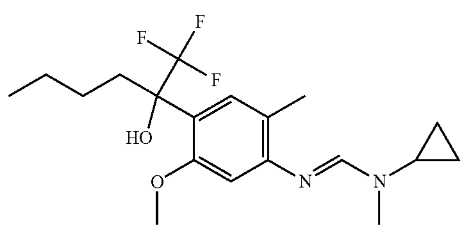 [SMILES: CCCCC(O)(c1cc(C)c(/N=C/N(C)C2CC2)cc1OC)C(F)(F)F] | 0.80 | 373 | A | |
| E1.050 | 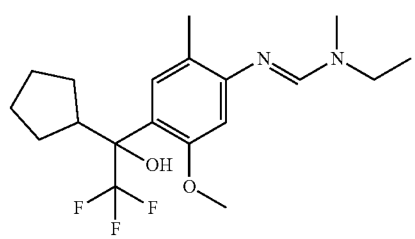 [SMILES: CCN(C)/C=N/c1cc(OC)c(C(O)(C2CCCC2)C(F)(F)F)cc1C] | 1.23 | 373 | A | |
| E1.051 | 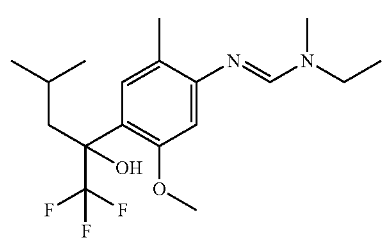 [SMILES: CCN(C)/C=N/c1cc(OC)c(C(O)(CC(C)C)C(F)(F)F)cc1C] | 1.16 | 361 | A | |
| E1.052 | 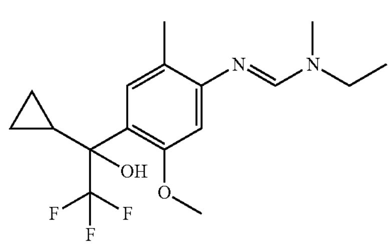 [SMILES: CCN(C)/C=N/c1cc(OC)c(C(O)(C2CC2)C(F)(F)F)cc1C] | 1.15 | 345 | A | 64-72 |

TABLE E-continued

Physical data of compounds of formula (I)
The compounds of formula (I) in Table E were prepared using techniques analogous
to those described above and/or common synthetic techniques generally known to the
person skilled in the art, as well as those described in WO 12/146125 (pp.370-378) and WO
08/101682 (pp.22-33).

| Entry | STRUCTURE | RT (min) | [M + H] (measured) | Method | MP ° C. |
|---|---|---|---|---|---|
| E1.053 | 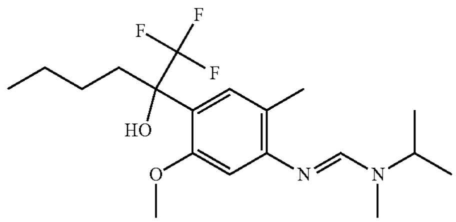 [SMILES: CCCCC(O)(c1cc(C)c(/N=C/N(C)C(C)C)cc1OC)C(F)(F)F] | 0.82 | 375 | A | |
| E1.054 | 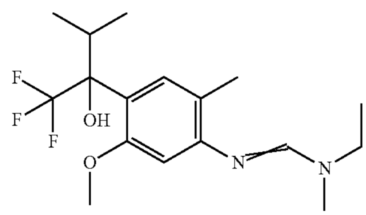 | 1.13 | 347 | A | 57-59 |
| E1.055 | 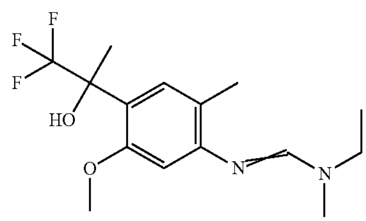 | 0.66 | 319 | A | 114-118 |
| E1.056 | 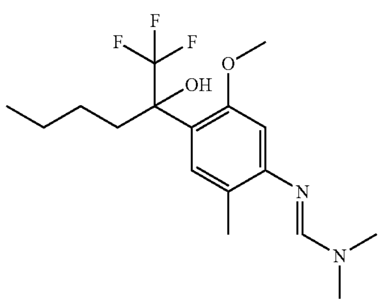 [SMILES: CCCCC(O)(c1cc(C)c(/N=C/N(C)C)cc1OC)C(F)(F)F] | 0.78 | 361 | A | |
| E1.057 | 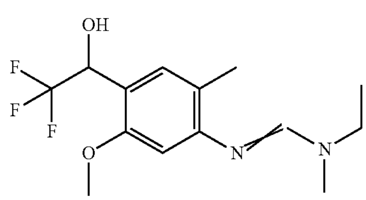 | | | | 128-132 |
| E1.058 | 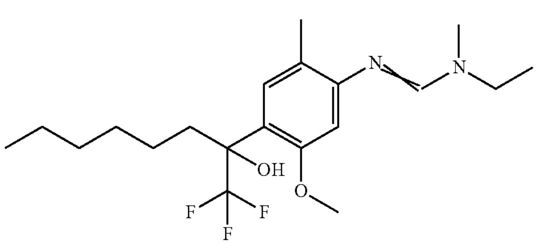 | 1.31 | 389 | A | |

TABLE E-continued

Physical data of compounds of formula (I)
The compounds of formula (I) in Table E were prepared using techniques analogous
to those described above and/or common synthetic techniques generally known to the
person skilled in the art, as well as those described in WO 12/146125 (pp.370-378) and WO
08/101682 (pp.22-33).

| Entry | STRUCTURE | RT (min) | [M + H] (measured) | Method | MP ° C. |
|---|---|---|---|---|---|
| E1.059 | 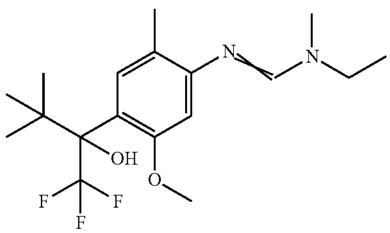 | 1.24 | 361 | A | 112-116 |
| E1.060 | 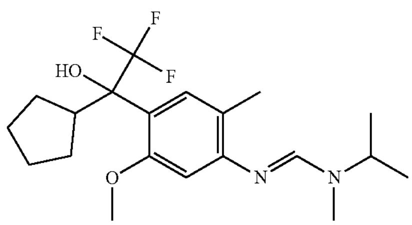 [SMILES: COc1cc(/N=C/N(C)C(C)C)c(C)cc1C(O)(C1CCCC1)C(F)(F)F] | 0.87 | 387 | A | |
| E1.061 | 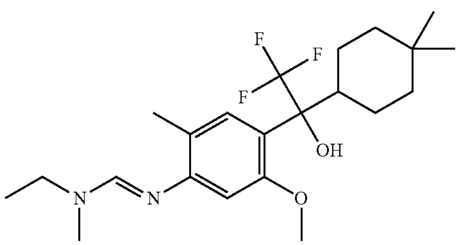 [SMILES: CCN(C)/C=N/c1cc(OC)c(C(O)(C2CCC(C)(C)CC2)C(F)(F)F)cc1C] | 0.95 | 416 | A | |
| E1.062 | 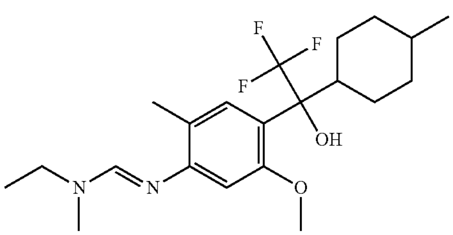 [SMILES: CCN(C)/C=N/c1cc(OC)c(C(O)(C2CCC(C)CC2)C(F)(F)F)cc1C] | 0.92 | 401 | A | |
| E1.063 | 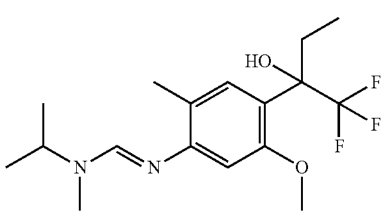 [SMILES: CCC(O)(c1cc(C)c(/N=C/N(C)C(C)C)cc1OC)C(F)(F)F] | | | | 73-76 |
| E1.064 | 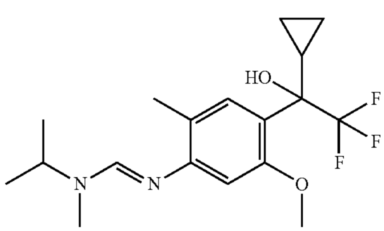 [SMILES: COc1cc(/N=C/N(C)C(C)C)c(C)cc1C(O)(C1CC1)C(F)(F)F] | | | | 90-93 |

TABLE E-continued

Physical data of compounds of formula (I)
The compounds of formula (I) in Table E were prepared using techniques analogous
to those described above and/or common synthetic techniques generally known to the
person skilled in the art, as well as those described in WO 12/146125 (pp.370-378) and WO
08/101682 (pp.22-33).

| Entry | STRUCTURE | RT (min) | [M + H] (measured) | Method | MP ° C. |
|---|---|---|---|---|---|
| E1.065 | 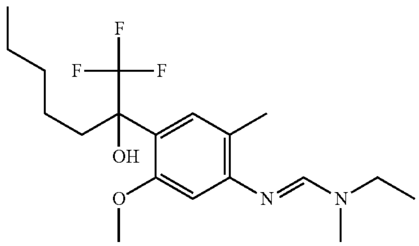 [SMILES: CCCCCC(O)(c1cc(C)c(/N=C/N(C)CC)cc1OC)C(F)(F)F] | 0.85 | 375 | A | |
| E1.066 | 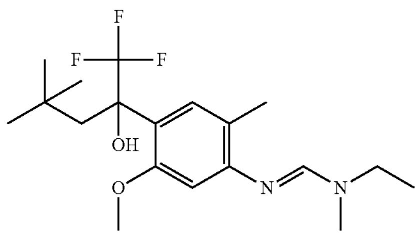 [SMILES: CCN(C)/C=N/c1cc(OC)c(C(O)(CC(C)(C)C)C(F)(F)F)cc1C] | 0.78 | 375 | A | |
| E1.067 | 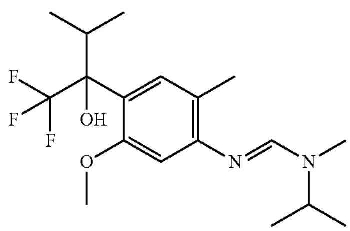 [SMILES: COc1cc(/N=C/N(C)C(C)C)c(C)cc1C(O)(C(C)C)C(F)(F)F] | 0.82 | 361 | A | 78-79 |
| E1.068 | 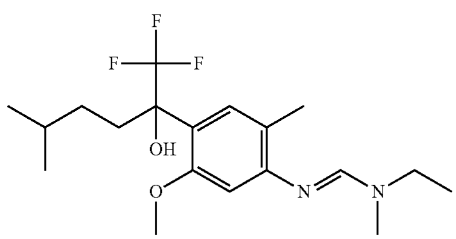 [SMILES: CCN(C)/C=N/c1cc(OC)c(C(O)(CCC(C)C)C(F)(F)F)cc1C] | 0.85 | 375 | A | |
| E1.069 | 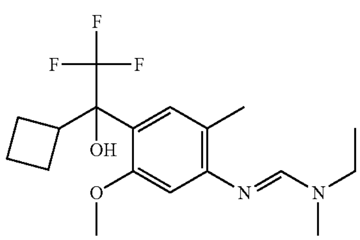 [SMILES: CCN(C)/C=N/c1cc(OC)c(C(O)(C2CCC2)C(F)(F)F)cc1C] | 0.83 | 359 | A | |
| E1.070 | 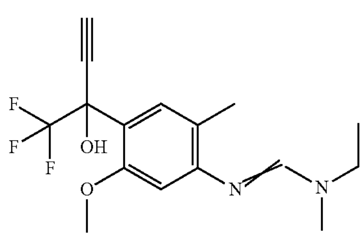 | 0.65 | 329 | A | |

TABLE E-continued

Physical data of compounds of formula (I)
The compounds of formula (I) in Table E were prepared using techniques analogous
to those described above and/or common synthetic techniques generally known to the
person skilled in the art, as well as those described in WO 12/146125 (pp.370-378) and WO
08/101682 (pp.22-33).

| Entry | STRUCTURE | RT (min) | [M + H] (measured) | Method | MP ° C. |
|---|---|---|---|---|---|
| E1.071 | 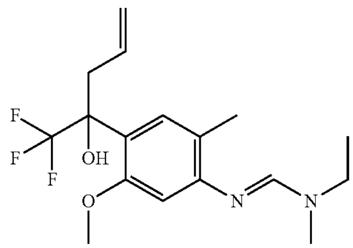 [SMILES: C=CCC(O)(c1cc(C)c(/N=C/N(C)CC)cc1OC)C(F)(F)F] | 1.18 | 345 | A | 123-127 |
| E1.072 | 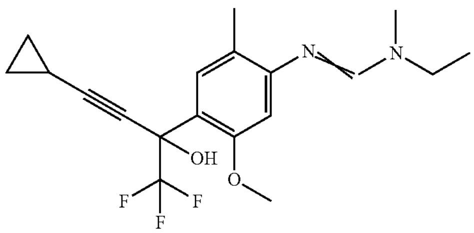 | 1.20 | 369 | A | 76-78 |
| E1.073 | 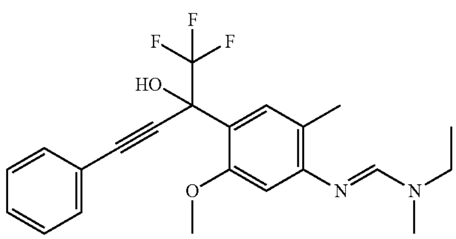 [SMILES: CCN(C)/C=N/c1cc(OC)c(C(O)(C#Cc2ccccc2)C(F)(F)F)cc1C] | 0.90 | 405 | A | 88-90 |
| E1.074 | 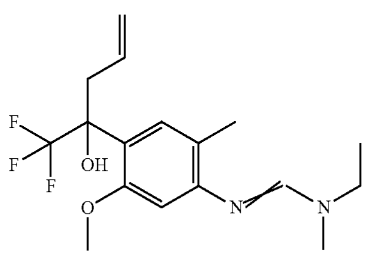 | 0.73 | 345 | A | |
| E1.075 | 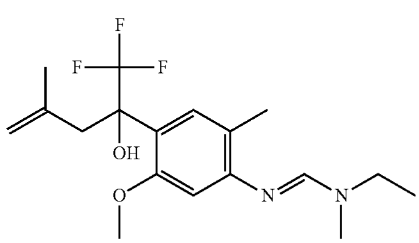 [SMILES: C=C(C)CC(O)(c1cc(C)c(/N=C/N(C)CC)cc1OC)C(F)(F)F] | 0.75 | 359 | A | |
| E1.076 | 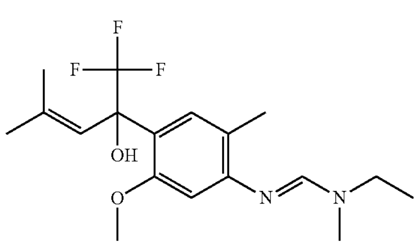 [SMILES: CCN(C)/C=N/c1cc(OC)c(C(O)(C=C(C)C)C(F)(F)F)cc1C] | 0.74 | 359 | A | |

TABLE E-continued

*Physical data of compounds of formula (I)*
*The compounds of formula (I) in Table E were prepared using techniques analogous*
*to those described above and/or common synthetic techniques generally known to the*
*person skilled in the art, as well as those described in WO 12/146125 (pp.370-378) and WO*
*08/101682 (pp.22-33).*

| Entry | STRUCTURE | RT (min) | [M + H] (measured) | Method | MP ° C. |
|---|---|---|---|---|---|
| E1.077 | 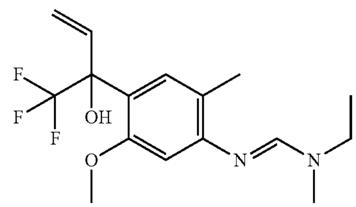 [SMILES: C=CC(O)(c1cc(C)c(/N=C/N(C)CC)cc1OC)C(F)(F)F] | 0.63 | 331 | A | |
| E1.078 | 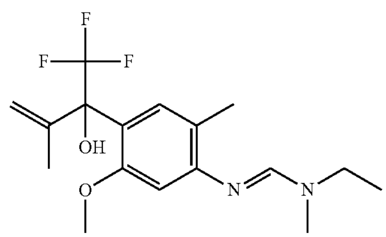 [SMILES: C=C(C)C(O)(c1cc(C)c(/N=C/N(C)CC)cc1OC)C(F)(F)F] | 0.73 | 345 | A | |
| E1.079 | 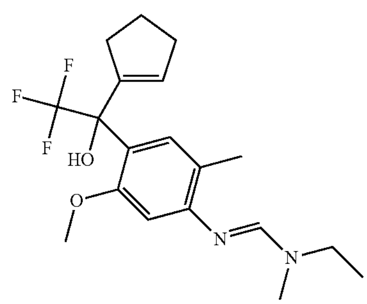 [SMILES: CCN(C)/C=N/c1cc(OC)c(C(O)(C2=CCCC2)C(F)(F)F)cc1C] | 0.81 | 371 | A | |
| E1.080 | 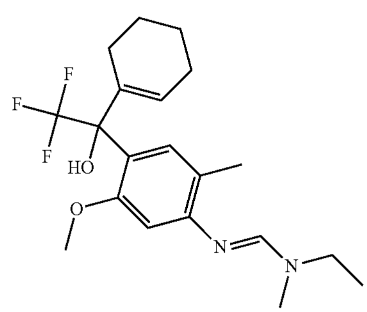 [SMILES: CCN(C)/C=N/c1cc(OC)c(C(O)(C2=CCCCC2)C(F)(F)F)cc1C] | 0.84 | 385 | A | |
| E1.081 | 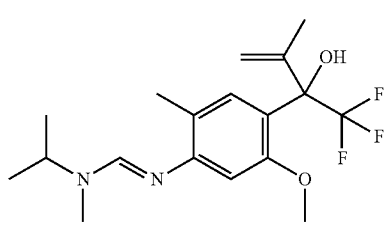 [SMILES: C=C(C)C(O)(c1cc(C)c(/N=C/N(C)C(C)C)cc1OC)C(F)(F)F] | | | | 110-113 |

TABLE E-continued

Physical data of compounds of formula (I)
The compounds of formula (I) in Table E were prepared using techniques analogous
to those described above and/or common synthetic techniques generally known to the
person skilled in the art, as well as those described in WO 12/146125 (pp.370-378) and WO
08/101682 (pp.22-33).

| Entry | STRUCTURE | RT (min) | [M + H] (measured) | Method | MP ° C. |
|---|---|---|---|---|---|
| E1.082 | 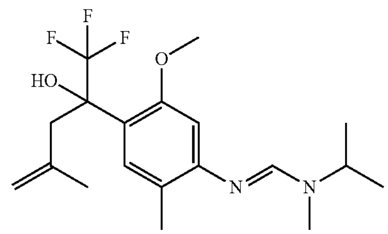 [SMILES: C=C(C)CC(O)(c1cc(C)c(/N=C/N(C)C(C)C)cc1OC)C(F)(F)F] | | | | 90-95 |
| E1.083 | 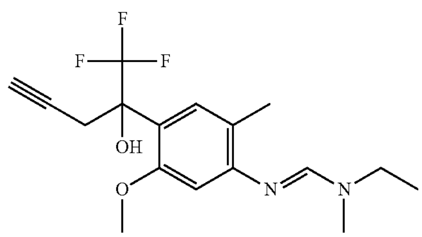 [SMILES: C#CCC(O)(c1cc(C)c(/N=C/N(C)CC)cc1OC)C(F)(F)F] | 0.82 | 343 | A | |
| E1.084 | 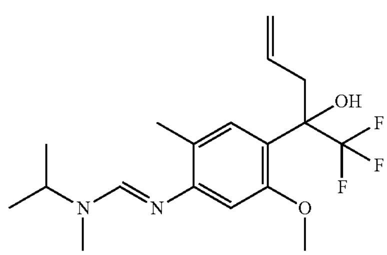 [SMILES: C=CCC(O)(c1cc(C)c(/N=C/N(C)C(C)C)cc1OC)C(F)(F)F] | | | | 45-50 |
| E1.085 | 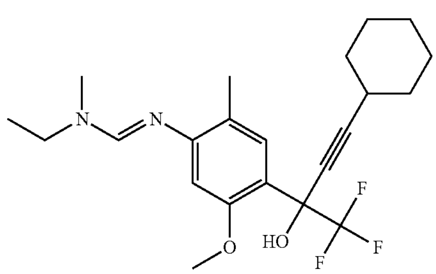 [SMILES: CCN(C)/C=N/c1cc(OC)c(C(O)(C#CC2CCCCC2)C(F)(F)F)cc1C] | 0.87 | 411 | A | 62-64 |
| E1.086 | 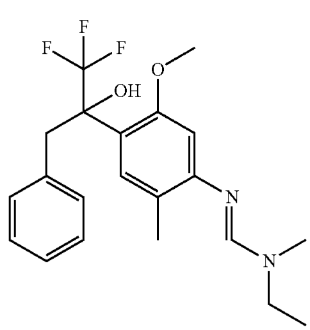 [SMILES: CCN(C)/C=N/c1cc(OC)c(C(O)(Cc2ccccc2)C(F)(F)F)cc1C] | 0.82 | 395 | A | |

TABLE E-continued

*Physical data of compounds of formula (I)*
*The compounds of formula (I) in Table E were prepared using techniques analogous*
*to those described above and/or common synthetic techniques generally known to the*
*person skilled in the art, as well as those described in WO 12/146125 (pp.370-378) and WO*
*08/101682 (pp.22-33).*

| Entry | STRUCTURE | RT (min) | [M + H] (measured) | Method | MP ° C. |
|---|---|---|---|---|---|
| E1.087 | 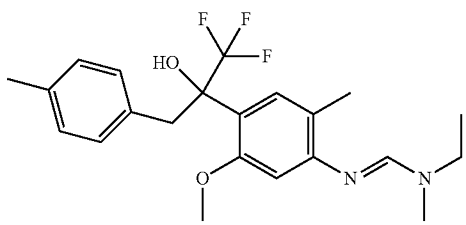 [SMILES: CCN(C)/C=N/c1cc(OC)c(C(O)(Cc2ccc(C)cc2)C(F)(F)F)cc1C] | 0.86 | 409 | A | |
| E1.088 | 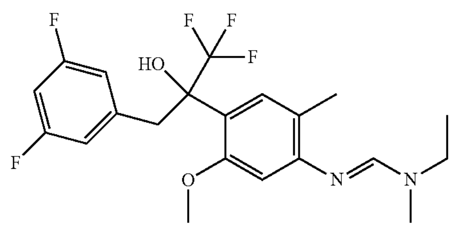 [SMILES: CCN(C)/C=N/c1cc(OC)c(C(O)(Cc2cc(F)cc(F)c2)C(F)(F)F)cc1C] | 0.84 | 331 | A | |
| E1.089 | 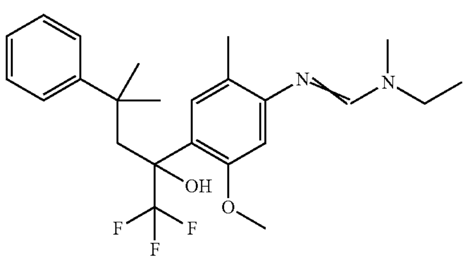 | 1.32 | 437 | A | |
| E1.090 | 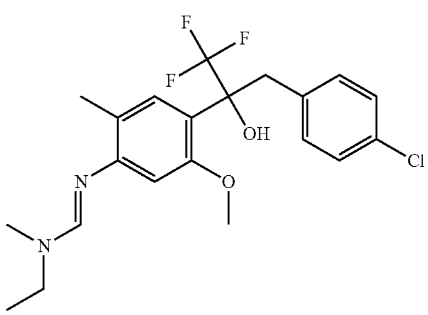 [SMILES: CCN(C)/C=N/c1cc(OC)c(C(O)(Cc2ccc(Cl)cc2)C(F)(F)F)cc1C] | 0.84 | 429 | A | 63-65 |
| E1.091 | 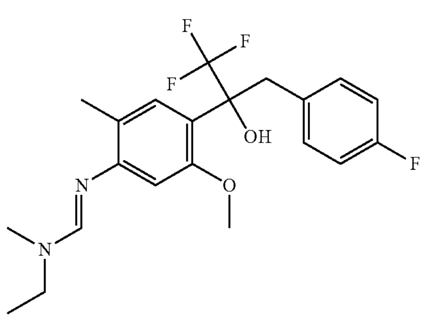 [SMILES: CCN(C)/C=N/c1cc(OC)c(C(O)(Cc2ccc(F)cc2)C(F)(F)F)cc1C] | 0.79 | 413 | A | |

TABLE E-continued

*Physical data of compounds of formula (I)*

The compounds of formula (I) in Table E were prepared using techniques analogous to those described above and/or common synthetic techniques generally known to the person skilled in the art, as well as those described in WO 12/146125 (pp.370-378) and WO 08/101682 (pp.22-33).

| Entry | STRUCTURE | RT (min) | [M + H] (measured) | Method | MP ° C. |
|-------|-----------|----------|--------------------|--------|---------|
| E1.092 | 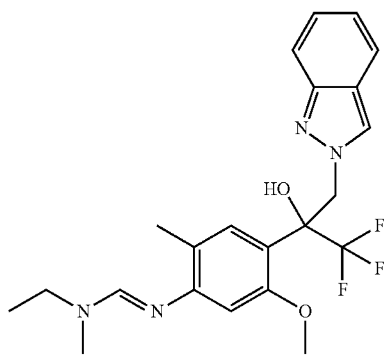 [SMILES: CCN(C)/C=N/c1cc(OC)c(C(O)(Cn2cc3ccccc3n2)C(F)(F)F)cc1C] | 0.80 | 435 | A | |
| E1.093 | 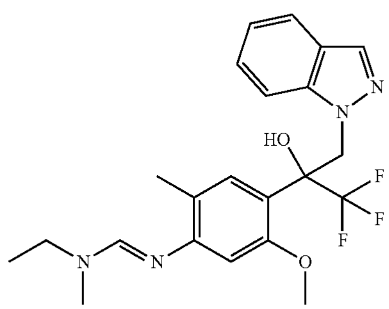 [SMILES: CCN(C)/C=N/c1cc(OC)c(C(O)(Cn2ncc3ccccc32)C(F)(F)F)cc1C] | 0.80 | 435 | A | |
| E1.094 | 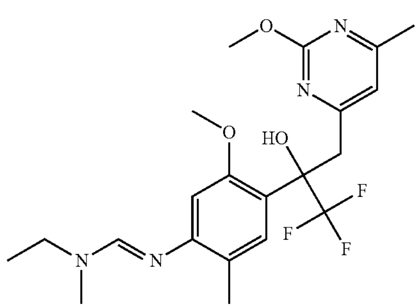 [SMILES: CCN(C)/C=N/c1cc(OC)c(C(O)(Cc2cc(C)nc(OC)n2)C(F)(F)F)cc1C] | 0.78 | 441 | A | 117-119 |
| E1.095 | 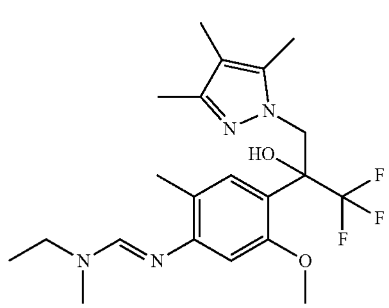 [SMILES: CCN(C)/C=N/c1cc(OC)c(C(O)(Cn2nc(C)c(C)c2C)C(F)(F)F)cc1C] | 0.89 | 427 | A | |

TABLE E-continued

*Physical data of compounds of formula (I)*

*The compounds of formula (I) in Table E were prepared using techniques analogous to those described above and/or common synthetic techniques generally known to the person skilled in the art, as well as those described in WO 12/146125 (pp.370-378) and WO 08/101682 (pp.22-33).*

| Entry | STRUCTURE | RT (min) | [M + H] (measured) | Method | MP ° C. |
|---|---|---|---|---|---|
| E1.096 | 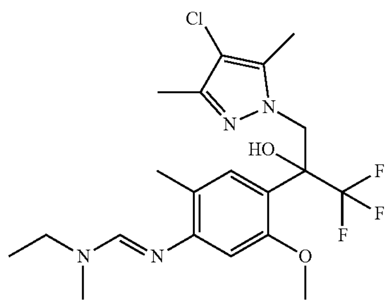 [SMILES: CCN(C)/C=N/c1cc(OC)c(C(O)(Cn2nc(C)c(Cl)c2C)C(F)(F)F)cc1C] | 0.80 | 447 | A | |
| E1.097 | 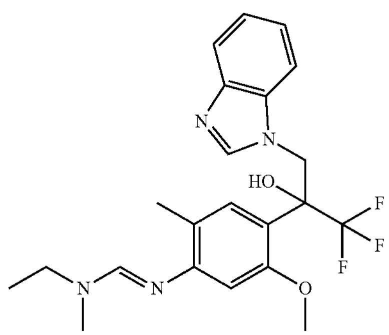 [SMILES: CCN(C)/C=N/c1cc(OC)c(C(O)(Cn2cnc3ccccc32)C(F)(F)F)cc1C] | 0.63 | 435 | A | |
| E1.098 | 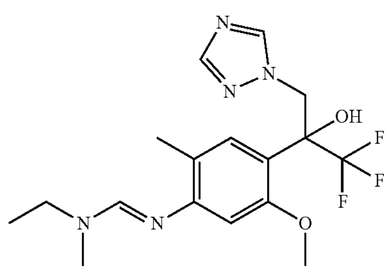 [SMILES: CCN(C)/C=N/c1cc(OC)c(C(O)(Cn2cncn2)C(F)(F)F)cc1C] | 0.61 | 386 | A | |
| E1.099 | 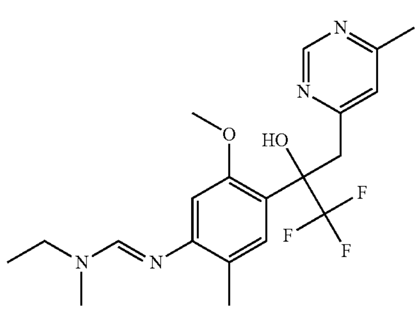 [SMILES: CCN(C)/C=N/c1cc(OC)c(C(O)(Cc2cc(C)ncn2)C(F)(F)F)cc1C] | 0.70 | 411 | A | 82-85 |

TABLE E-continued

Physical data of compounds of formula (I)
The compounds of formula (I) in Table E were prepared using techniques analogous
to those described above and/or common synthetic techniques generally known to the
person skilled in the art, as well as those described in WO 12/146125 (pp.370-378) and WO
08/101682 (pp.22-33).

| Entry | STRUCTURE | RT (min) | [M + H] (measured) | Method | MP ° C. |
|---|---|---|---|---|---|
| E1.100 | 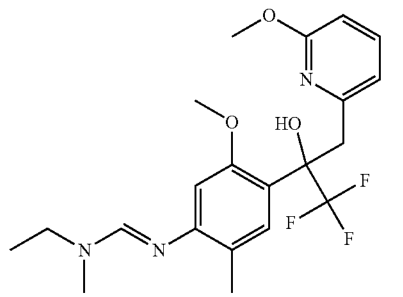 [SMILES: CCN(C)/C=N/c1cc(OC)c(C(O)(Cc2cccc(OC)n2)C(F)(F)F)cc1C] | 0.83 | 426 | A | 92-95 |
| E1.101 | 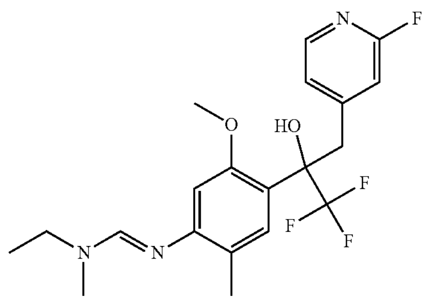 [SMILES: CCN(C)/C=N/c1cc(OC)c(C(O)(Cc2ccnc(F)c2)C(F)(F)F)cc1C] | 0.71 | 414 | A | |
| E1.102 | 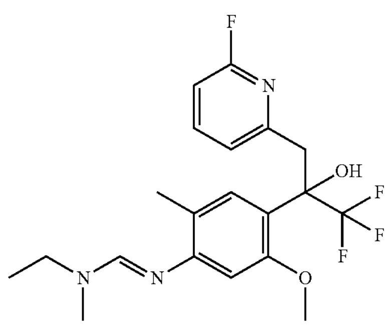 [SMILES: CCN(C)/C=N/c1cc(OC)c(C(O)(Cc2cccc(F)n2)C(F)(F)F)cc1C] | 0.77 | 414 | A | |
| E1.103 | 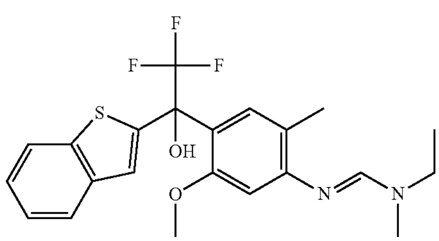 [SMILES: CCN(C)/C=N/c1cc(OC)c(C(O)(c2cc3ccccc3s2)C(F)(F)F)cc1C] | 0.85 | 437 | A | |
| E1.104 | 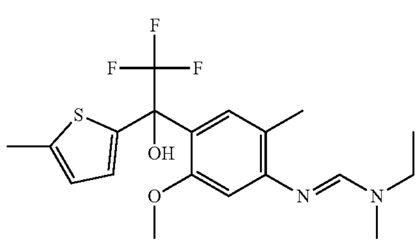 [SMILES: CCN(C)/C=N/c1cc(OC)c(C(O)(c2ccc(C)s2)C(F)(F)F)cc1C] | 0.74 | 401 | A | |

TABLE E-continued

*Physical data of compounds of formula (I)*

The compounds of formula (I) in Table E were prepared using techniques analogous to those described above and/or common synthetic techniques generally known to the person skilled in the art, as well as those described in WO 12/146125 (pp.370-378) and WO 08/101682 (pp.22-33).

| Entry | STRUCTURE | RT (min) | [M + H] (measured) | Method | MP ° C. |
|---|---|---|---|---|---|
| E1.105 | 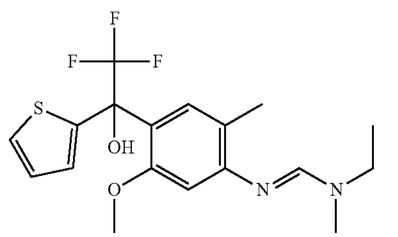 [SMILES: CCN(C)/C=N/c1cc(OC)c(C(O)(c2cccs2)C(F)(F)F)cc1C] | 0.83 | 387 | A | |
| E1.106 | 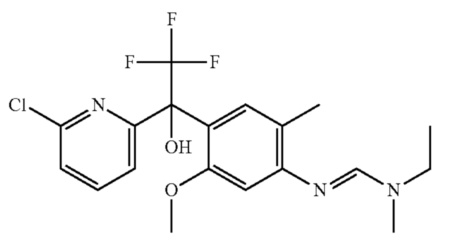 [SMILES: CCN(C)/C=N/c1cc(OC)c(C(O)(c2cccc(Cl)n2)C(F)(F)F)cc1C] | 0.76 | 416 | A | |
| E1.107 | 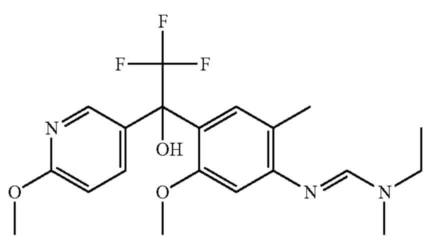 [SMILES: CCN(C)/C=N/c1cc(OC)c(C(O)(c2ccc(OC)nc2)C(F)(F)F)cc1C] | 0.73 | 412 | A | 100-102 |
| E1.108 | 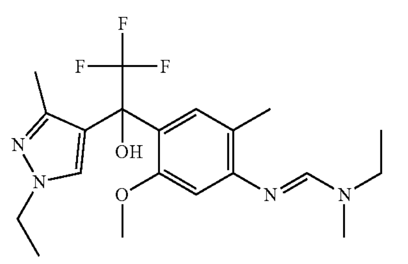 [SMILES: CCN(C)/C=N/c1cc(OC)c(C(O)(c2cn(CC)nc2C)C(F)(F)F)cc1C] | 0.70 | 427 | A | |
| E1.109 | 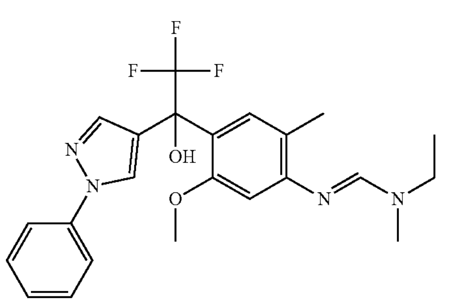 [SMILES: CCN(C)/C=N/c1cc(OC)c(C(O)(c2cnn(-c3ccccc3)c2)C(F)(F)F)cc1C] | 0.79 | 447 | A | |

TABLE E-continued

Physical data of compounds of formula (I)

The compounds of formula (I) in Table E were prepared using techniques analogous to those described above and/or common synthetic techniques generally known to the person skilled in the art, as well as those described in WO 12/146125 (pp.370-378) and WO 08/101682 (pp.22-33).

| Entry | STRUCTURE | RT (min) | [M + H] (measured) | Method | MP ° C. |
|---|---|---|---|---|---|
| E1.110 | 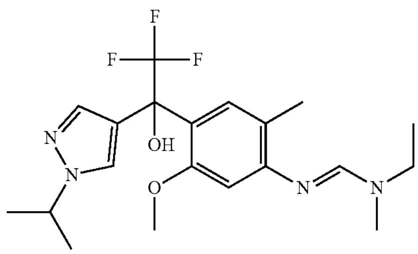 [SMILES: CCN(C)/C=N/c1cc(OC)c(C(O)(c2cnn(C(C)C)c2)C(F)(F)F)cc1C] | 0.67 | 413 | A | |
| E1.111 | 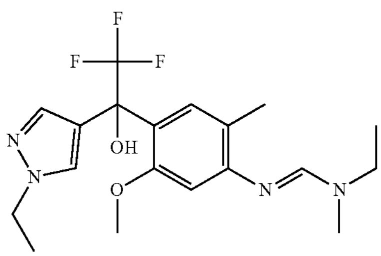 [SMILES: CCN(C)/C=N/c1cc(OC)c(C(O)(c2cnn(CC)c2)C(F)(F)F)cc1C] | 0.64 | 399 | A | |
| E1.112 | 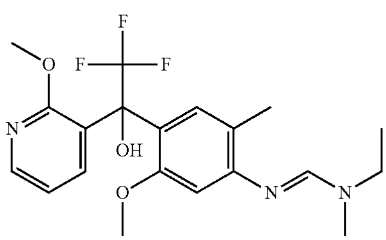 [SMILES: CCN(C)/C=N/c1cc(OC)c(C(O)(c2cccnc2OC)C(F)(F)F)cc1C] | 0.73 | 412 | A | |
| E1.113 | 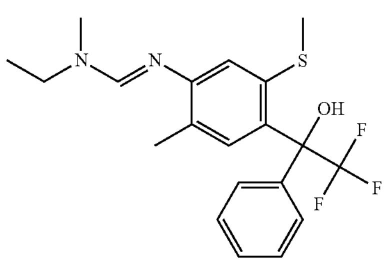 [SMILES: CCN(C)/C=N/c1cc(SC)c(C(O)(c2ccccc2)C(F)(F)F)cc1C] | 0.77 | 397 | A | 160-165 |
| E1.114 | 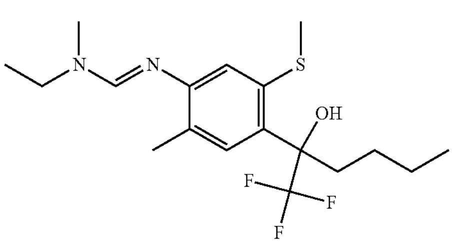 [SMILES: CCCCC(O)(c1cc(C)c(/N=C/N(C)CC)cc1SC)C(F)(F)F] | | | | |

TABLE E-continued

Physical data of compounds of formula (I)
The compounds of formula (I) in Table E were prepared using techniques analogous
to those described above and/or common synthetic techniques generally known to the
person skilled in the art, as well as those described in WO 12/146125 (pp.370-378) and WO
08/101682 (pp.22-33).

| Entry | STRUCTURE | RT (min) | [M + H] (measured) | Method | MP ° C. |
|---|---|---|---|---|---|
| E1.115 | 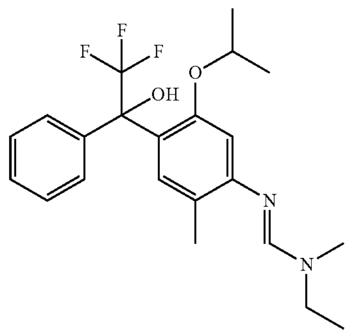 [SMILES: CCN(C)/C=N/c1cc(OC(C)C)c(C(O)(c2ccccc2)C(F)(F)F)cc1C] | 0.88 | 409 | A | 119-120 |
| E1.116 | 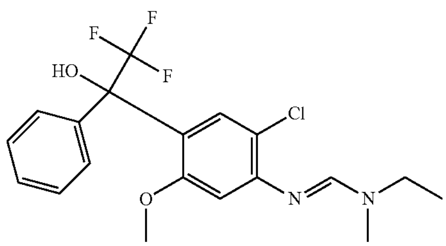 [SMILES: CCN(C)/C=N/c1cc(OC)c(CC(O)(c2ccccc2)C(F)(F)F)cc1Cl] | 0.81 | 401 | A | |
| E1.117 | 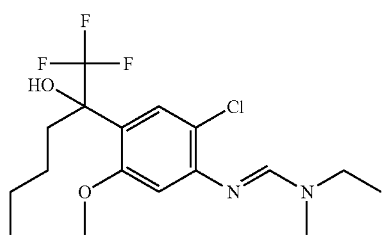 [SMILES: CCCCC(O)(c1cc(Cl)c(/N=C/N(C)CC)cc1OC)C(F)(F)F] | 0.82 | 381 | A | |
| E1.118 | 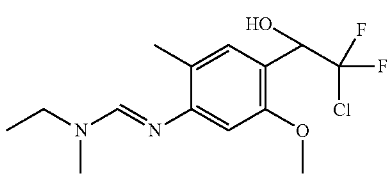 [SMILES: CCN(C)/C=N/c1cc(OC)c(C(O)C(F)(F)Cl)cc1C] | 0.64 | 321 | A | |
| E1.119 | 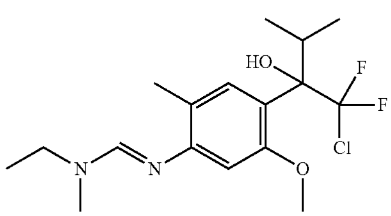 [SMILES: CCN(C)/C=N/c1cc(OC)c(C(O)(C(C)C)C(F)(F)Cl)cc1C] | 0.80 | 363 | A | |
| E1.120 | 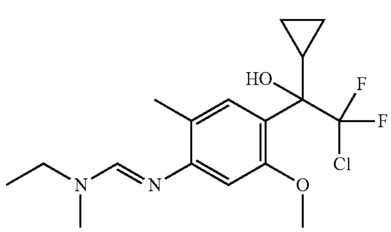 [SMILES: CCN(C)/C=N/c1cc(OC)c(C(O)(C2CC2)C(F)(F)Cl)cc1C] | 0.79 | 361 | A | |

TABLE E-continued

Physical data of compounds of formula (I)
The compounds of formula (I) in Table E were prepared using techniques analogous
to those described above and/or common synthetic techniques generally known to the
person skilled in the art, as well as those described in WO 12/146125 (pp.370-378) and WO
08/101682 (pp.22-33).

| Entry | STRUCTURE | RT (min) | [M + H] (measured) | Method | MP ° C. |
|---|---|---|---|---|---|
| E1.121 | 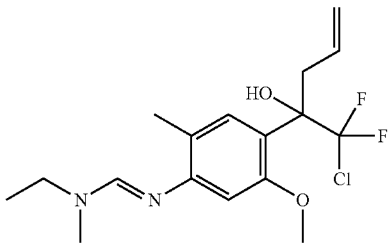 [SMILES: C=CCC(O)(c1cc(C)c(/N=C/N(C)CC)cc1OC)C(F)(F)Cl] | 0.75 | 361 | A | |
| E1.122 | 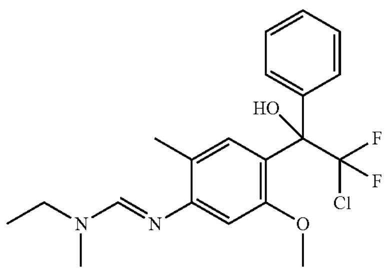 [SMILES: CCN(C)/C=N/c1cc(OC)c(C(O)(c2ccccc2)C(F)(F)Cl)cc1C] | 0.78 | 397 | A | |
| E1.123 | 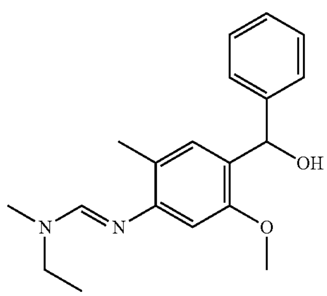 [SMILES: CCN(C)/C=N/c1cc(OC)c(C(O)c2ccccc2)cc1C] | 0.71 | 313 | A | |
| E1.124 | 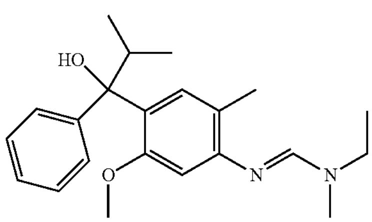 [SMILES: CCN(C)/C=N/c1cc(OC)c(C(O)(c2ccccc2)C(C)C)cc1C] | 0.89 | 355 | A | 82-84 |
| E1.125 | 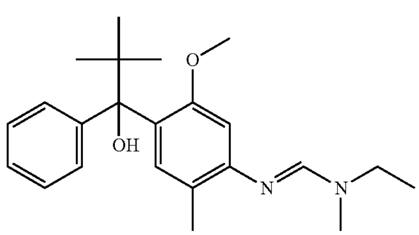 [SMILES: CCN(C)/C=N/c1cc(OC)c(C(O)(c2ccccc2)C(C)(C)C)cc1C] | 1.00 | 369 | A | 90-92 |
| E1.126 | 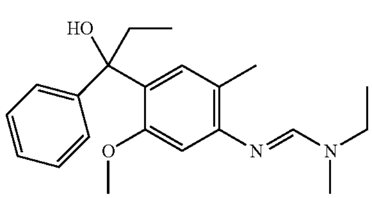 [SMILES: CCN(C)/C=N/c1cc(OC)c(C(O)(CC)c2ccccc2)cc1C] | 0.82 | 341 | A | 87-89 |

TABLE E-continued

Physical data of compounds of formula (I)
The compounds of formula (I) in Table E were prepared using techniques analogous to those described above and/or common synthetic techniques generally known to the person skilled in the art, as well as those described in WO 12/146125 (pp.370-378) and WO 08/101682 (pp.22-33).

| Entry | STRUCTURE | RT (min) | [M + H] (measured) | Method | MP ° C. |
|---|---|---|---|---|---|
| E1.127 | 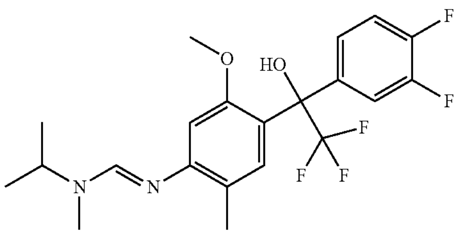 [SMILES: COc1cc(/N=C/N(C)C(C)C)c(C)cc1C(O)(c1ccc(F)c(F)c1)C(F)(F)F] | 0.85 | 431 | A | 116-118 |
| E1.128 | 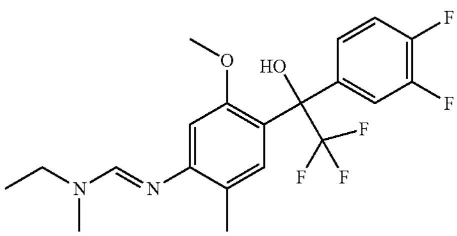 [SMILES: CCN(C)/C=N/c1cc(OC)c(C(O)(c2ccc(F)c(F)c2)C(F)(F)F)cc1C] | 0.80 | 417 | A | 108-110 |
| E1.129 | 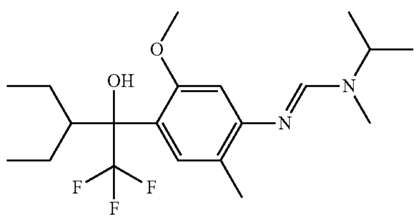 [SMILES: CCC(CC)C(O)(c1cc(C)c(/N=C/N(C)C(C)C)cc1OC)C(F)(F)F] | 0.91 | 389 | A | |
| E1.130 | 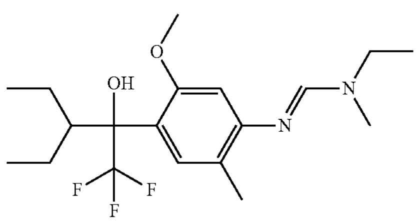 | 0.87 | 375 | A | |
| E1.131 | 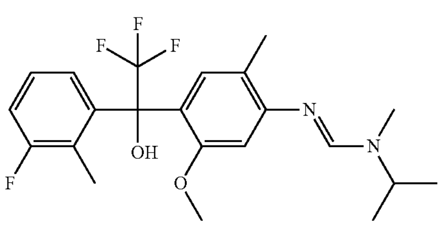 [SMILES: COc1cc(/N=C/N(C)C(C)C)c(C)cc1C(O)(c1cccc(F)c1C)C(F)(F)F] | 0.83 | 427 | A | 127-129 |
| E1.132 | 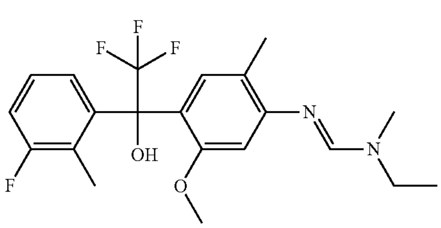 [SMILES: CCN(C)/C=N/c1cc(OC)c(C(O)(c2cccc(F)c2C)C(F)(F)F)cc1C] | 0.83 | 413 | A | 107-109 |

TABLE E-continued

Physical data of compounds of formula (I)
The compounds of formula (I) in Table E were prepared using techniques analogous
to those described above and/or common synthetic techniques generally known to the
person skilled in the art, as well as those described in WO 12/146125 (pp.370-378) and WO
08/101682 (pp.22-33).

| Entry | STRUCTURE | RT (min) | [M + H] (measured) | Method | MP ° C. |
|---|---|---|---|---|---|
| E1.133 | 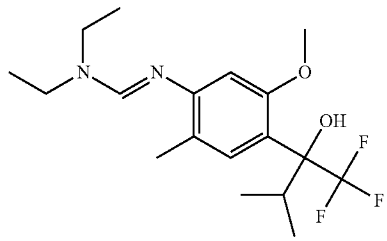 [SMILES: CCN(/C=N/c1cc(OC)c(C(O)(C(C)C)C(F)(F)F)cc1C)CC] | 0.82 | 361 | A | 60-62 |
| E1.134 | 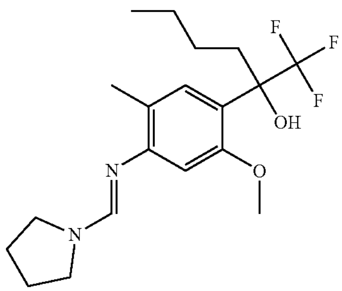 [SMILES: CCCCC(O)(c1cc(C)c(/N=C/N2CCCC2)cc1OC)C(F)(F)F] | 0.80 | 373 | A | 103-105 |
| E1.135 | | 0.80 | 393 | A | 157-159 |
| E1.135 | | 0.83 | 359 | A | 102-104 |
| E1.135 | | 0.87 | 431 | A | 112-115 |
| E1.136 | 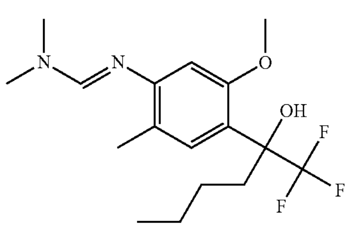 [SMILES: CCCCC(O)(c1cc(C)c(/N=C/N(C)C)cc1OC)C(F)(F)F] | 0.77 | 347 | A | |

TABLE E-continued

Physical data of compounds of formula (I)
The compounds of formula (I) in Table E were prepared using techniques analogous
to those described above and/or common synthetic techniques generally known to the
person skilled in the art, as well as those described in WO 12/146125 (pp.370-378) and WO
08/101682 (pp.22-33).

| Entry | STRUCTURE | RT (min) | [M + H] (measured) | Method | MP ° C. |
|---|---|---|---|---|---|
| E1.137 | 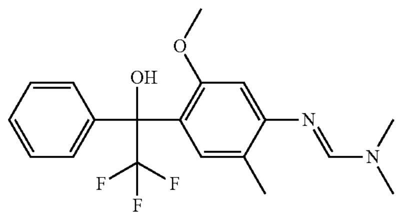 [SMILES: COc1cc(/N=C/N(C)C)c(C)cc1C(O)(c1ccccc1)C(F)(F)F] | 0.73 | 367 | A | 133-135 |
| E1.138 | 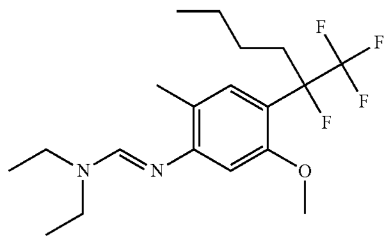 [SMILES: CCCCC(F)(c1cc(C)c(/N=C/N(CC)CC)cc1OC)C(F)(F)F] | 0.81 | 375 | A | 97-99 |
| E1.139 | 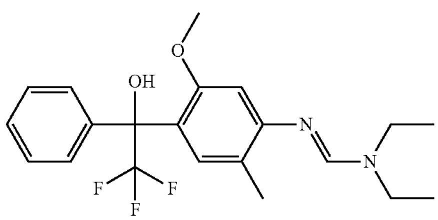 [SMILES: CCN(/C=N/c1cc(OC)c(C(O)(c2ccccc2)C(F)(F)F)cc1C)CC] | 0.80 | 395 | A | 102-104 |
| E1.140 | 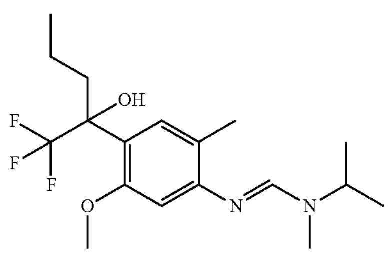 [SMILES: CCCC(O)(c1cc(C)c(/N=C/N(C)C(C)C)cc1OC)C(F)(F)F] | 0.79 | 332 | A | 110-112 |
| E1.141 | 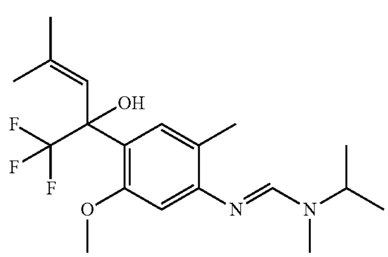 [SMILES: COc1cc(/N=C/N(C)C(C)C)c(C)cc1C(O)(C=C(C)C)C(F)(F)F] | 0.76 | 373 | A | 77-79 |
| E1.142 | 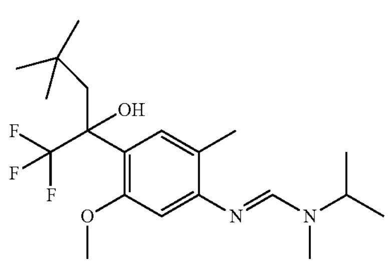 [SMILES: COc1cc(/N=C/N(C)C(C)C)c(C)cc1C(O)(CC(C)(C)C)C(F)(F)F] | 0.81 | 389 | A | |

TABLE E-continued

Physical data of compounds of formula (I)
The compounds of formula (I) in Table E were prepared using techniques analogous to those described above and/or common synthetic techniques generally known to the person skilled in the art, as well as those described in WO 12/146125 (pp.370-378) and WO 08/101682 (pp.22-33).

| Entry | STRUCTURE | RT (min) | [M + H] (measured) | Method | MP ° C. |
|---|---|---|---|---|---|
| E1.143 | 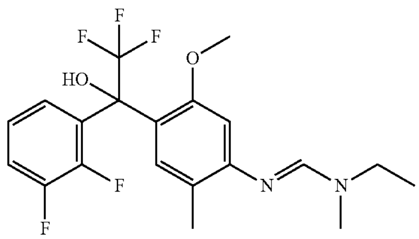 [SMILES: CCN(C)/C=N/c1cc(OC)c(C(O)(c2cccc(F)c2F)C(F)(F)F)cc1C] | 0.79 | 417 | A | 130-132 |
| E1.144 | 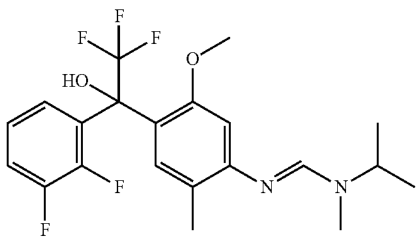 [SMILES: COc1cc(/N=C/N(C)C(C)C)c(C)cc1C(O)(c1cccc(F)c1F)C(F)(F)F] | 0.82 | 431 | A | 97-99 |
| E1.145 | 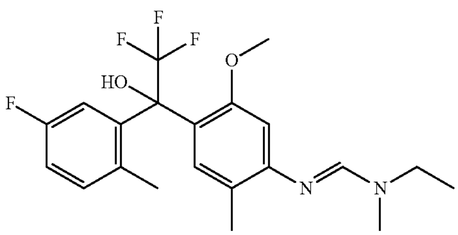 [SMILES: CCN(C)/C=N/c1cc(OC)c(C(O)(c2cc(F)ccc2C)C(F)(F)F)cc1C] | 0.82 | 413 | A | 95-97 |
| E1.146 | 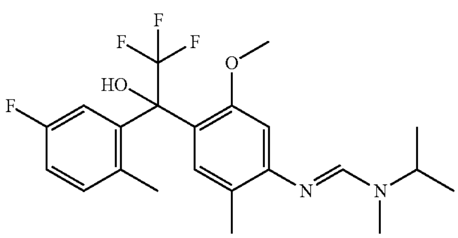 | 0.85 | 427 | A | 116-118 |
| E1.147 | 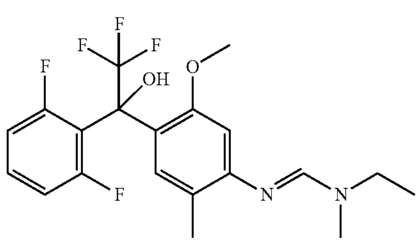 [SMILES: CCN(C)/C=N/c1cc(OC)c(C(O)(c2c(F)cccc2F)C(F)(F)F)cc1C] | 0.79 | 417 | A | 128-130 |
| E1.148 | 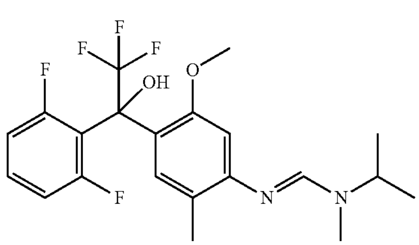 [SMILES: COc1cc(/N=C/N(C)C(C)C)c(C)cc1C(O)(c1c(F)cccc1F)C(F)(F)F] | 0.82 | 431 | A | 119-121 |

TABLE E-continued

*Physical data of compounds of formula (I)*
*The compounds of formula (I) in Table E were prepared using techniques analogous to those described above and/or common synthetic techniques generally known to the person skilled in the art, as well as those described in WO 12/146125 (pp.370-378) and WO 08/101682 (pp.22-33).*

| Entry | STRUCTURE | RT (min) | [M + H] (measured) | Method | MP ° C. |
|---|---|---|---|---|---|
| E1.148 | 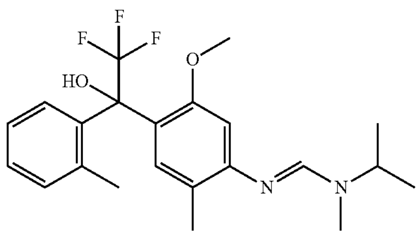 [SMILES: COc1cc(/N=C/N(C)C(C)C)c(C)cc1C(O)(c1ccccc1C)C(F)(F)F] | 0.86 | 409 | A | 138-140 |
| E1.149 | 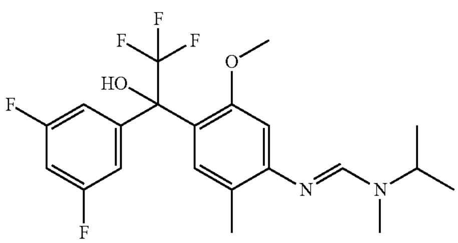 [SMILES: COc1cc(/N=C/N(C)C(C)C)c(C)cc1C(O)(c1cc(F)cc(F)c1)C(F)(F)F] | 0.83 | 431 | A | 110-112 |
| E1.150 | 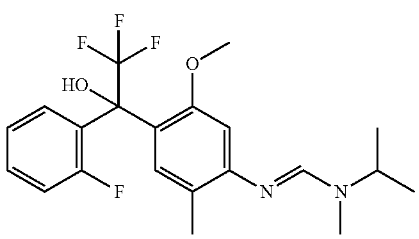 | 0.80 | 413 | A | 86-88 |
| E1.151 | 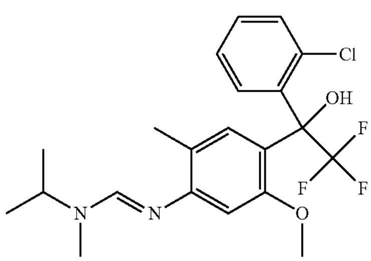 [SMILES: COc1cc(/N=C/N(C)C(C)C)c(C)cc1C(O)(c1ccccc1Cl)C(F)(F)F] | 0.86 | 429 | A | 67-69 |
| E1.152 | 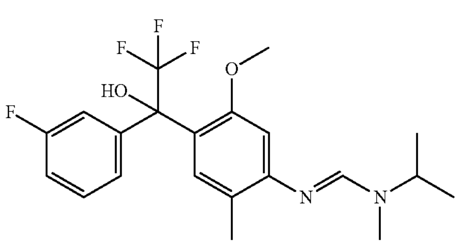 [SMILES: COc1cc(/N=C/N(C)C(C)C)c(C)cc1C(O)(c1cccc(F)c1)C(F)(F)F] | 0.82 | 413 | A | 92-94 |

TABLE E-continued

Physical data of compounds of formula (I)
The compounds of formula (I) in Table E were prepared using techniques analogous
to those described above and/or common synthetic techniques generally known to the
person skilled in the art, as well as those described in WO 12/146125 (pp.370-378) and WO
08/101682 (pp.22-33).

| Entry | STRUCTURE | RT (min) | [M + H] (measured) | Method | MP ° C. |
|---|---|---|---|---|---|
| E1.153 | 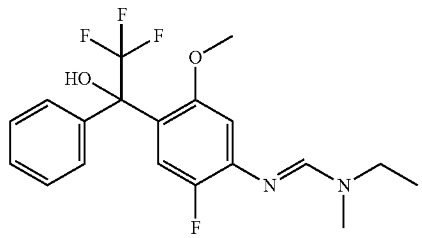 [SMILES: CCN(C)/C=N/c1cc(OC)c(C(O)(c2ccccc2)C(F)(F)F)cc1F] | 0.77 | 385 | A | 144-146 |
| E1.154 | 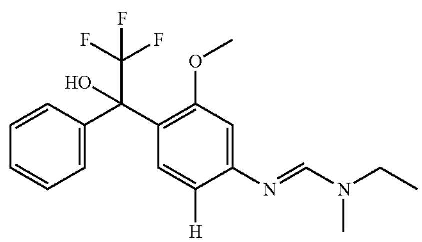 [SMILES: CCN(C)/C=N/c1ccc(C(O)(c2ccccc2)C(F)(F)F)c(OC)c1] | 0.76 | 367 | A | |
| E1.155 | 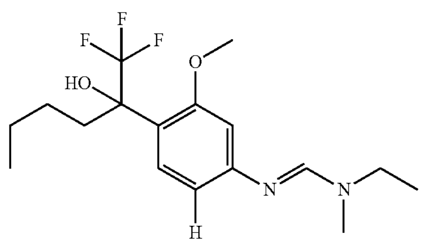 [SMILES: CCCCC(O)(c1cc(F)c(/N=C/N(C)CC)cc1OC)C(F)(F)F] | 0.80 | 347 | A | |
| E1.156 | 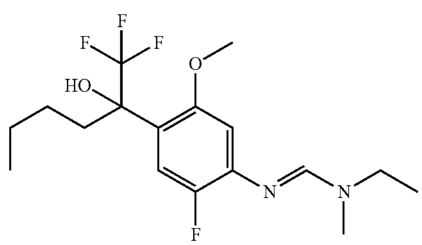 | 0.81 | 365 | A | |
| E1.157 | 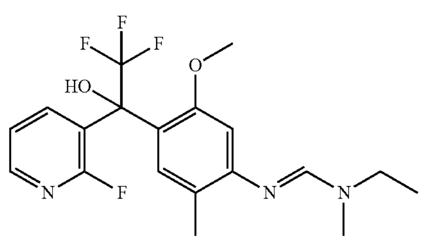 [SMILES: CCN(C)/C=N/c1cc(OC)c(C(O)(c2cccnc2F)C(F)(F)F)cc1C] | 0.72 | 400 | A | 113-115 |
| E1.158 | 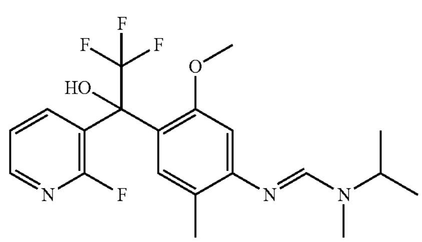 [SMILES: COc1cc(/N=C/N(C)C(C)C)c(C)cc1C(O)(c1cccnc1F)C(F)(F)F] | 0.75 | 414 | A | 120-122 |

HPLC Method Used

Method A:

Spectra were recorded on a Mass Spectrometer (ACQUITY UPLC) from Waters 10 (SQD, SQDII or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. 15 Solvent degasser, binary pump, heated column compartment and diode-array detector. Column: Waters UPLC HSS T3, 1.8 mm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH, gradient: 10-100% B in 1.2 min; Flow (ml/min) 0.85

BIOLOGICAL EXAMPLES

*Blumeria graminis f. sp. tritici* (*Erysiphe graminis f. sp. tritici*)/Wheat/Leaf Disc Preventative (Powdery Mildew on Wheat)

Wheat leaf segments cv. Kanzler were placed on agar in a multiwell plate (24-well format) and sprayed with the formulated test compound diluted in water. The leaf disks were inoculated by shaking powdery mildew infected plants above the test plates 1 day after application. The inoculated leaf disks were incubated at 20° C. and 60% rh under a light regime of 24 h darkness followed by 12 h light/12 h darkness in a climate chamber and the activity of a compound was assessed as percent disease control compared to untreated when an appropriate level of disease damage appears on untreated check leaf segments (6-8 days after application).

The following compounds gave at 200 ppm give at least 80% disease control in this test when compared to untreated control leaf disks under the same conditions, which show extensive disease development E1.001, E1.003, E1.004, E1.005, E1.006, E1.007, E1.010, E1.011, E1.013, E1.014, E1.015, E1.016, E1.017, E1.018, E1.019, E1.020, E1.021, E1.022, E1.023, E1.024, E1.025, E1.026, E1.027, E1.029, E1.030, E1.031, E1.032, E1.033, E1.034, E1.035, E1.037, E1.038, E1.039, E1.040, E1.041, E1.042, E1.043, E1.044, E1.045, E1.046, E1.047, E1.048, E1.049, E1.050, E1.051, E1.052, E1.053, E1.054, E1.055, E1.056, E1.057, E1.058, E1.059, E1.060, E1.061, E1.062, E1.063, E1.064, E1.065, E1.066, E1.067, E1.068, E1.069, E1.070, E1.071, E1.072, E1.074, E1.075, E1.076, E1.077, E1.078, E1.079, E1.080, E1.081, E1.082, E1.083, E1.084, E1.086, E1.087, E1.088, E1.089, E1.090, E1.091, E1.092, E1.093, E1.094, E1.095, E1.098, E1.099, E1.100, E1.101, E1.102, E1.103, E1.104, E1.105, E1.106, E1.107, E1.108, E1.109, E1.112, E1.113, E1.114, E1.117, E1.118, E1.119, E1.120, E1.121, E1.122, E1.123, E1.126.

*Phakopsora pachyrhizi*/Soybean/Leaf Disk Preventative (Soybean Rust)

Four-week old soybean plants are sprayed in a spray chamber with the formulated test compound diluted in water. Leaf disks are cut from treated plants and placed on agar into 24-well plates one day after application. Leaf disks are inoculated by spraying them with a spore suspension on their lower leaf surface. After an incubation period in a climate cabinet of 24-36 hours in darkness at 20° C. and 75% rh, the leaf disks are then kept at 20° C. with 12 h light/day and 75% rh. The percentage leaf disk area covered by disease is assessed when an appropriate level of disease appears on untreated check plants (12-14 days after application).

The following compounds gave at 200 ppm gave at least 80% disease control in this test when compared to untreated control leaf disks under the same conditions, which show extensive disease development E1.001, E1.002, E1.003, E1.004, E1.005, E1.006, E1.007, E1.010, E1.011, E1.014, E1.015, E1.016, E1.017, E1.018, E1.020, E1.022, E1.023, E1.024, E1.026, E1.027, E1.029, E1.030, E1.031, E1.033, E1.034, E1.035, E1.037, E1.044, E1.045, E1.046, E1.047, E1.048, E1.049, E1.050, E1.051, E1.052, E1.053, E1.054, E1.055, E1.056, E1.057, E1.058, E1.059, E1.061, E1.062, E1.063, E1.064, E1.065, E1.066, E1.067, E1.068, E1.069, E1.070, E1.071, E1.072, E1.074, E1.075, E1.076, E1.077, E1.078, E1.081, E1.082, E1.083, E1.084, E1.086, E1.087, E1.088, E1.089, E1.090, E1.091, E1.093, E1.095, E1.096, E1.099, E1.100, E1.101, E1.102, E1.103, E1.104, E1.105, E1.106, E1.111, E1.112, E1.114, E1.117, E1.118, E1.119, E1.120, E1.121, E1.122, E1.123, E1.124, E1.125, E1.126

*Puccinia recondita f. sp. tritici*/Wheat/Leaf Disc Preventative (Brown Rust)

Wheat leaf segments cv. Kanzler were placed on agar in multiwell plates (24-well format) and sprayed with the formulated test compound diluted in water. The leaf disks were inoculated with a spore suspension of the fungus 1 day after application. The inoculated leaf segments were incubated at 19° C. and 75% rh under a light regime of 12 h light/12 h darkness in a climate cabinet and the activity of a compound was assessed as percent disease control compared to untreated when an appropriate level of disease damage appears in untreated check leaf segments (7-9 days after application).

The following compounds gave at 200 ppm gave at least 80% disease control in this test when compared to untreated control leaf disks under the same conditions, which show extensive disease development:

E1.001, E1.002, E1.003, E1.004, E1.005, E1.006, E1.007, E1.008, E1.009, E1.010, E1.011, E1.013, E1.014, E1.015, E1.016, E1.017, E1.018, E1.019, E1.020, E1.021, E1.022, E1.023, E1.024, E1.025, E1.026, E1.027, E1.028, E1.029, E1.030, E1.031, E1.032, E1.033, E1.034, E1.035, E1.036, E1.046, E1.047, E1.048, E1.049, E1.050, E1.051, E1.052, E1.053, E1.054, E1.055, E1.056, E1.057, E1.058, E1.059, E1.060, E1.061, E1.062, E1.063, E1.064, E1.065, E1.066, E1.067, E1.068, E1.069, E1.070, E1.071, E1.072, E1.073, E1.074, E1.075, E1.076, E1.077, E1.078, E1.079, E1.080, E1.081, E1.082, E1.083, E1.084, E1.086, E1.087, E1.088, E1.089, E1.092, E1.093, E1.094, E1.095, E1.098, E1.099, E1.100, E1.101, E1.103, E1.104, E1.105, E1.106, E1.107, E1.108, E1.109, E1.110, E1.111, E1.112, E1.116, E1.117, E1.118, E1.119, E1.120, E1.121, E1.122, E1.123, E1.124, E1.125, E1.126

*Puccinia recondita f. sp. tritici*/Wheat/Leaf Disc Curative (Brown Rust)

Wheat leaf segments cv. Kanzler are placed on agar in multiwell plates (24-well format). The leaf segments are inoculated with a spore suspension of the fungus. Plates were stored in darkness at 19° C. and 75% rh. The formulated test compound diluted in water was applied 1 day after inoculation. The leaf segments were incubated at 19° C. and 75% rh under a light regime of 12 h light/12 h darkness in a climate cabinet and the activity of a compound was assessed as percent disease control compared to untreated when an appropriate level of disease damage appears in untreated check leaf segments (6-8 days after application).

The following compounds gave at 200 ppm gaive at least 80% disease control in this test when compared to untreated control leaf disks under the same conditions, which show extensive disease development:

E1.001, E1.002, E1.003, E1.004, E1.005, E1.006, E1.007, E1.008, E1.009, E1.010, E1.011, E1.013, E1.014, E1.015, E1.016, E1.017, E1.018, E1.019, E1.020, E1.021, E1.022, E1.023, E1.024, E1.025, E1.026, E1.027, E1.028, E1.029, E1.030, E1.031, E1.032, E1.033, E1.034, E1.035, E1.036, E1.037, E1.038, E1.039, E1.040, E1.041, E1.042, E1.043, E1.044, E1.045, E1.046, E1.047, E1.048, E1.049, E1.050, E1.051, E1.052, E1.053, E1.054, E1.055, E1.056, E1.057, E1.058, E1.059, E1.060, E1.061, E1.062, E1.063, E1.064, E1.065, E1.066, E1.067, E1.068, E1.069, E1.070, E1.071, E1.072, E1.074, E1.075, E1.076, E1.077, E1.078, E1.079, E1.080, E1.081, E1.082, E1.083, E1.084, E1.085, E1.086, E1.087, E1.088, E1.089, E1.090, E1.091, E1.092, E1.093, E1.094, E1.095, E1.098, E1.099, E1.100, E1.101, E1.102, E1.103, E1.104, E1.105, E1.106, E1.107, E1.108, E1.109, E1.110, E1.111, E1.112, E1.113, E1.114, E1.116, E1.117, E1.118, E1.119, E1.120, E1.121, E1.122, E1.123, E1.124, E1.125, E1.126

The invention claimed is:
1. A compound of formula (I):

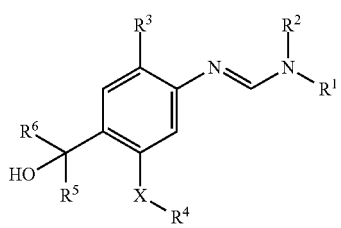

wherein,
$R^1$ and $R^2$ are each independently selected from $C_1$-$C_4$ alkyl and $C_3$-$C_8$ cycloalkyl; or
$R^1$ and $R^2$ together with the nitrogen atom to which they are attached form a three to six-membered saturated cyclic group which may optionally contain one oxygen or one sulphur atom;
$R^3$ is hydrogen, halogen or $C_1$-$C_4$ alkyl;
$R^4$ is $C_1$-$C_4$ alkyl or $C_1$-$C_4$ haloalkyl;
$R^5$ and $R^6$ are each independently selected from $C_1$-$C_6$ alkyl, $C_1$-$C_6$ haloalkyl, $C_3$-$C_8$ cycloalkyl, $C_2$-$C_6$ alkenyl, $C_2$-$C_6$ haloalkenyl, $C_2$-$C_6$ alkynyl, aryl optionally substituted with one to three $R^7$ groups, aryl($C_1$-$C_4$) alkyl wherein the aryl is optionally substituted with one to three $R^7$ groups, heteroaryl($C_1$-$C_4$)alkyl wherein the heteroaryl is optionally substituted with one to three $R^7$ groups and heteroaryl optionally substituted with one to three $R^7$ groups;
X is $NR^8$, O or S;
Each $R^7$ is independently selected from halogen, cyano, hydroxyl, amino, nitro, $C_1$-$C_4$alkyl, $C_1$-$C_4$haloalkyl, $C_3$-$C_6$cycloalkyl, $C_3$-$C_6$halocycloalkyl, $C_1$-$C_4$alkoxy, $C_1$-$C_4$haloalkoxy, $C_3$-$C_6$cycloalkoxy, $C_1$-$C_4$alkylthio, $C_1$-$C_4$haloalkylthio, $C_3$-$C_6$cycloalkylthio, $C_1$-$C_4$alkylsulfinyl, $C_1$-$C_4$haloalkylsulfinyl, $C_1$-$C_4$alkylsulfonyl, $C_1$-$C_4$haloalkylsulfonyl, $C_1$-$C_4$alkylcarbonyl, $C_2$-$C_6$alkenyl, $C_2$-$C_6$haloalkenyl, $C_2$-$C_6$alkenyloxy, $C_2$-$C_6$haloalkenyloxy, $C_2$-$C_6$alkynyl, $C_3$-$C_6$cycloalkyl$C_2$-$C_6$alkynyl, $C_2$-$C_6$alkynyloxy, aryl, aryl($C_1$-$C_4$)alkyl, aryloxy, heteroaryl, heteroaryl($C_1$-$C_4$)alkyl and heteroaryloxy; and
$R^8$ is selected from hydrogen, $C_1$-$C_4$ alkyl, $C_1$-$C_4$ alkoxy and $C_3$-$C_8$cycloalkyl; or a salt or an N-oxide thereof.

2. A compound according to claim 1, wherein $R^1$ and $R^2$ are each independently $C_1$-$C_4$ alkyl.

3. A compound according to claim 1, wherein $R^3$ is hydrogen, fluoro, chloro, or $C_1$-$C_4$ alkyl.

4. A compound according to claim 1, $R^4$ is $C_1$-$C_3$alkyl or $C_1$-$C_3$haloalkyl.

5. A compound according to claim 1, wherein $R^5$ and $R^6$ are each independently selected from $C_1$-$C_6$ alkyl, $C_1$-$C_6$ haloalkyl, $C_3$-$C_8$ cycloalkyl, $C_2$-$C_6$ alkenyl, phenyl optionally substituted with one to three $R^7$ groups, phenyl($C_1$-$C_4$) alkyl wherein the phenyl is optionally substituted with one to three $R^7$ groups, pyrazolyl($C_1$-$C_4$)alkyl wherein the pyrazole is optionally substituted with one to three $R^7$ groups and pyridyl optionally substituted with one to three $R^7$ groups, and wherein each $R^7$ is independently selected from halogen, cyano, $C_1$-$C_4$alkyl, $C_1$-$C_4$haloalkyl, $C_3$-$C_6$cycloalkyl, $C_1$-$C_4$alkoxy, $C_1$-$C_4$haloalkoxy, $C_3$-$C_6$cycloalkoxy, $C_1$-$C_4$alkylthio, $C_1$-$C_4$alkylsulfonyl, $C_1$-$C_4$haloalkylsulfonyl, $C_1$-$C_4$alkylcarbonyl, $C_2$-$C_6$alkenyl, $C_2$-$C_6$haloalkenyl, $C_2$-$C_6$alkynyl, phenyl, benzyl, phenoxy, pyridyl, pyridylmethyl and pyridyloxy.

6. A compound according to claim 1, wherein X is $NR^8$ or O, where $R^8$ is hydrogen, $C_1$-$C_4$ alkyl or $C_1$-$C_4$ alkoxy.

7. A compound according to claim 1, wherein $R^1$ and $R^2$ are each independently selected from methyl, ethyl, propyl and isopropyl.

8. A compound according to claim 1, wherein $R^3$ is hydrogen or $C_1$-$C_3$ alkyl.

9. A compound according to claim 1, wherein $R^5$ and $R^6$ are each independently selected from $C_1$-$C_6$ alkyl, $C_1$-$C_6$ haloalkyl, $C_3$-$C_5$ cycloalkyl, phenyl optionally substituted with one or two $R^7$ groups and pyridyl optionally substituted with one or two $R^7$ groups, and wherein each $R^7$ is independently selected from halogen, cyano, $C_1$-$C_4$alkyl, $C_1$-$C_4$haloalkyl, $C_3$-$C_6$cycloalkyl, $C_1$-$C_4$alkoxy, $C_1$-$C_4$haloalkoxy, $C_1$-$C_4$alkylthio, $C_1$-$C_4$alkylsulfonyl, $C_1$-$C_4$alkylcarbonyl, $C_2$-$C_6$alkynyl, phenyl, phenoxy and pyridyl.

10. A compound according to claim 1, wherein X is O.

11. A compound according to claim 1, wherein $R^1$ and $R^2$ are each independently selected from methyl, ethyl and isopropyl; $R^3$ is hydrogen or $C_1$-$C_2$ alkyl; $R^4$ is methyl or ethyl; $R^5$ and $R^6$ are each independently selected from $C_1$-$C_2$ haloalkyl, phenyl optionally substituted with one or two $R^7$ groups, ethyl, n-propyl, i-propyl, n-butyl, iso-butyl, neopentyl, cyclopropyl, cyclobutyl or cyclopentyl; X is N-methyl or O; and each $R^7$ is independently selected from halogen, cyano, $C_1$-$C_4$alkyl, $C_1$-$C_4$haloalkyl, $C_1$-$C_4$alkoxy, $C_1$-$C_4$haloalkoxy, $C_2$-$C_6$alkynyl and phenyl; or a salt or N-oxide thereof.

12. A compound according to claim 1, wherein
$R^1$ is methyl and $R^2$ is ethyl or isopropyl; or, alternatively, $R^1$ and $R^2$ are both ethyl;
$R^3$ is hydrogen or methyl;
$R^4$ is methyl;
$R^5$ is $CF_3$, $CClF_2$ or $CF_2CF_3$;
$R^6$ is phenyl optionally substituted by one methyl group and/or one or two halogen atoms, preferably fluoro or chloro, n-propyl, i-propyl, n-butyl, iso-butyl or neopentyl;
or, alternatively, $R^6$ is cyclopropyl; and
X is O; or a salt or N-oxide thereof.

13. A compound according to claim 12, wherein $R^3$ is methyl.

14. A compound according to claim 12, wherein $R^5$ is $CF_3$.

15. A composition comprising a fungicidally effective amount of a compound of formula (I) as defined in claim 1.

16. A composition according to claim 15, wherein the composition further comprises at least one additional active ingredient and/or a diluent.

17. A method of combating or controlling phytopathogenic diseases which comprises applying to a phytopathogen, to the locus of a phytopathogen, or to a plant susceptible to attack by a phytopathogen, or to propagation material thereof, a fungicidally effective amount of a compound of formula (I) as defined in claim 1 or a composition comprising a fungicidally effective amount of a compound of formula (I) as defined in claim 1.

* * * * *